(12) United States Patent
Oldfield et al.

(10) Patent No.: US 12,201,769 B2
(45) Date of Patent: Jan. 21, 2025

(54) METHODS AND APPARATUS FOR OXYGENATION AND/OR CO2 REMOVAL

(71) Applicant: Fisher & Paykel Healthcare Limited, Auckland (NZ)

(72) Inventors: Samantha Dale Oldfield, Auckland (NZ); Penelope Jane Maxwell, Auckland (NZ); Callum James Thomas Spence, Auckland (NZ); Thomas Heinrich Barnes, Auckland (NZ); Matthew Jon Payton, Auckland (NZ); Laith Adeeb Hermez, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 122 days.

(21) Appl. No.: 17/854,853

(22) Filed: Jun. 30, 2022

(65) Prior Publication Data

US 2023/0125297 A1    Apr. 27, 2023

Related U.S. Application Data

(62) Division of application No. 16/096,660, filed as application No. PCT/IB2017/052457 on Apr. 28, 2017, now Pat. No. 11,406,787.
(Continued)

(51) Int. Cl.
*A61M 16/00* (2006.01)
*A61B 5/00* (2006.01)
(Continued)

(52) U.S. Cl.
CPC ....... *A61M 16/0069* (2014.02); *A61B 5/0205* (2013.01); *A61B 5/4836* (2013.01);
(Continued)

(58) Field of Classification Search
CPC .............. A61M 16/00; A61M 16/0006; A61M 16/0057; A61M 16/0066; A61M 16/0069;
(Continued)

(56) References Cited

U.S. PATENT DOCUMENTS 3,410,264 A    11/1968    Frederik
4,155,356 A     5/1979    Venegas
(Continued)

FOREIGN PATENT DOCUMENTS

CA    2688537 A1    5/2008
CN    101448539     12/2012
(Continued)

OTHER PUBLICATIONS

Brighenti, C. et al., 'Effects of the Ventilator Patient Circuit on the Respiratory Parameter estimates: A Simulation Study', IFMBE Proceedings MEDICON, Modelling and Simulation of Physiological Systems, Jun. 12-15, 2001, Part II, pp. 915-918.
(Continued)

*Primary Examiner* — Joseph D. Boecker
(74) *Attorney, Agent, or Firm* — Knobbe Martens Olson & Bear LLP

(57) ABSTRACT

An apparatus for oxygenation and/or CO2 clearance of a patient. The apparatus comprising: a flow source or a connection for a flow source for providing a gas flow, a gas flow modulator, a controller to control the gas flow. The controller is operable to: receive input relating to heart activity and/or trachea gas flow of the patient, and control the gas flow modulator to provide a varying gas flow with at least two oscillating components. One oscillating component has a frequency based on the heart activity and/or trachea flow of the patient. One oscillating component has a frequency to: promote bulk gas flow movement, or promote mixing.

20 Claims, 39 Drawing Sheets

Related U.S. Application Data

(60) Provisional application No. 62/406,809, filed on Oct. 11, 2016, provisional application No. 62/329,474, filed on Apr. 29, 2016.

(51) Int. Cl.
*A61B 5/0205* (2006.01)
*A61M 16/06* (2006.01)
*A61M 16/08* (2006.01)
*A61M 16/10* (2006.01)
*A61M 16/16* (2006.01)
*A61M 16/20* (2006.01)

(52) U.S. Cl.
CPC .... *A61M 16/0006* (2014.02); *A61M 16/0066* (2013.01); *A61M 16/024* (2017.08); *A61M 16/0672* (2014.02); *A61M 16/16* (2013.01); *A61M 16/203* (2014.02); *A61M 16/204* (2014.02); *A61M 16/209* (2014.02); *A61M 2016/0027* (2013.01); *A61M 2016/0036* (2013.01); *A61M 16/0858* (2014.02); *A61M 16/104* (2013.01); *A61M 16/208* (2013.01); *A61M 2202/0208* (2013.01); *A61M 2230/04* (2013.01); *A61M 2230/42* (2013.01); *A61M 2230/46* (2013.01)

(58) Field of Classification Search
CPC .. A61M 16/022; A61M 16/024; A61M 16/04; A61M 16/06; A61M 16/0672; A61M 16/203; A61M 16/204; A61M 2230/04; A61M 2230/06; A61M 2230/42; A61M 2230/46; A61B 5/0205
See application file for complete search history.

(56) References Cited

U.S. PATENT DOCUMENTS

| | | | |
|---|---|---|---|
| 4,719,910 A * | 1/1988 | Jensen | A61M 16/042 128/204.21 |
| 4,805,612 A | 2/1989 | Jensen | |
| 4,821,709 A * | 4/1989 | Jensen | A61M 16/0006 128/204.21 |
| 5,165,398 A | 11/1992 | Bird | |
| 5,271,389 A | 12/1993 | Isaza et al. | |
| 6,029,664 A | 2/2000 | Zdrojkowski et al. | |
| 6,029,665 A | 2/2000 | Berthon-Jones | |
| 6,085,747 A | 7/2000 | Axe et al. | |
| 6,193,677 B1 | 2/2001 | Cady | |
| 6,390,092 B1 | 5/2002 | Leehoven | |
| 6,446,629 B1 | 9/2002 | Takaki et al. | |
| 6,557,554 B1 | 5/2003 | Sugiura | |
| 6,934,579 B2 | 8/2005 | Mantzaridis et al. | |
| 7,267,123 B2 | 9/2007 | Aylsworth et al. | |
| 7,861,716 B2 | 1/2011 | Borrello | |
| 8,631,799 B2 | 1/2014 | Davenport et al. | |
| 11,406,787 B2 | 8/2022 | Oldfield et al. | |
| 11,433,198 B2 | 9/2022 | White et al. | |
| 11,491,291 B2 | 11/2022 | Oldfield et al. | |
| 2001/0009152 A1 | 7/2001 | Bennarsten | |
| 2003/0010344 A1 * | 1/2003 | Bird | A61M 16/12 128/205.24 |
| 2004/0069304 A1 | 4/2004 | Jam | |
| 2005/0121033 A1 | 6/2005 | Starr et al. | |
| 2005/0178383 A1 | 8/2005 | Mackie | |
| 2005/0257788 A1 | 11/2005 | Aylsworth et al. | |
| 2006/0005842 A1 | 1/2006 | Rashad et al. | |
| 2006/0042638 A1 | 3/2006 | Niklewski et al. | |
| 2006/0084877 A1 | 4/2006 | Ujhazy et al. | |
| 2006/0162727 A1 | 7/2006 | Biondi et al. | |
| 2006/0174885 A1 | 8/2006 | Aylsworth et al. | |
| 2006/0174889 A1 | 8/2006 | Noble | |
| 2007/0113847 A1 | 5/2007 | Acker et al. | |
| 2007/0175473 A1 | 8/2007 | Lewis et al. | |
| 2007/0215154 A1 | 9/2007 | Borrello | |
| 2008/0142019 A1 | 6/2008 | Lewis et al. | |
| 2009/0007913 A1 * | 1/2009 | Lee | A61M 16/0072 128/205.24 |
| 2009/0126731 A1 * | 5/2009 | Dunsmore | A61M 16/0096 128/203.12 |
| 2009/0145428 A1 | 6/2009 | Sward et al. | |
| 2009/0156952 A1 | 6/2009 | Hunter et al. | |
| 2009/0253995 A1 | 10/2009 | Lewis et al. | |
| 2010/0078024 A1 | 4/2010 | Andreiux et al. | |
| 2010/0101583 A1 | 4/2010 | Chen et al. | |
| 2010/0252037 A1 | 10/2010 | Wondka | |
| 2010/0319691 A1 | 12/2010 | Lurie et al. | |
| 2011/0114098 A1 | 5/2011 | Mcauley et al. | |
| 2011/0125052 A1 | 5/2011 | Davenport et al. | |
| 2011/0214676 A1 | 9/2011 | Allum | |
| 2012/0017904 A1 | 1/2012 | Ratto | |
| 2012/0060840 A1 | 3/2012 | Refsland et al. | |
| 2012/0103337 A1 * | 5/2012 | Avni | A61M 21/02 128/204.23 |
| 2012/0266882 A1 | 10/2012 | Dellaca et al. | |
| 2013/0012828 A1 | 1/2013 | Aylsworth | |
| 2013/0133655 A1 | 5/2013 | Kimm et al. | |
| 2014/0150789 A1 | 6/2014 | Flanagan et al. | |
| 2014/0190481 A1 | 7/2014 | Jam | |
| 2014/0283834 A1 | 9/2014 | Ahmad et al. | |
| 2014/0350429 A1 | 11/2014 | Truschel et al. | |
| 2015/0027445 A1 | 1/2015 | Garde et al. | |
| 2015/0059751 A1 | 3/2015 | Cortez, Jr. et al. | |
| 2015/0119742 A1 | 4/2015 | Tse et al. | |
| 2015/0119743 A1 | 4/2015 | Maksym | |
| 2015/0128942 A1 | 5/2015 | Tatkov et al. | |
| 2015/0182713 A1 | 7/2015 | Phuah et al. | |
| 2015/0258291 A1 | 9/2015 | Richards-Kortum et al. | |
| 2015/0335851 A1 | 11/2015 | Cullen et al. | |
| 2015/0359982 A1 | 12/2015 | Garde et al. | |
| 2016/0193438 A1 | 7/2016 | White et al. | |
| 2016/0228661 A1 | 8/2016 | Larsson | |
| 2016/0339191 A1 * | 11/2016 | Kaczka | A61M 16/0006 |
| 2016/0367779 A1 | 12/2016 | Landis et al. | |
| 2017/0087316 A1 | 3/2017 | White et al. | |
| 2017/0151402 A1 * | 6/2017 | Belisario | A61M 16/0072 |
| 2017/0303821 A1 | 10/2017 | Hete | |
| 2018/0104426 A1 | 4/2018 | Oldfield et al. | |
| 2018/0126110 A1 | 5/2018 | Payton et al. | |
| 2021/0052844 A1 | 2/2021 | Oldfield et al. | |
| 2023/0012896 A1 | 1/2023 | White et al. | |
| 2023/0177882 A1 * | 6/2023 | Oldfield | A61B 5/087 382/103 |

FOREIGN PATENT DOCUMENTS

| | | |
|---|---|---|
| EP | 0127923 A2 | 12/1984 |
| EP | 3259001 | 10/2018 |
| GB | 2357037 | 6/2001 |
| GB | 2442875 A | 4/2008 |
| JP | 2001-500039 | 1/2001 |
| JP | 2007530079 | 11/2007 |
| JP | 2015-506802 | 3/2015 |
| WO | WO 98/10818 A1 | 3/1998 |
| WO | WO 03/066145 | 8/2003 |
| WO | WO 2005/006941 | 1/2005 |
| WO | WO 2005/011556 | 2/2005 |
| WO | WO 2006/088007 | 8/2006 |
| WO | WO 2008/030261 | 3/2008 |
| WO | WO 2008/039703 | 4/2008 |
| WO | WO 2009/094532 | 7/2009 |
| WO | WO 2010/076704 | 7/2010 |
| WO | WO 2011/007346 | 1/2011 |
| WO | WO 2013/042007 | 3/2013 |
| WO | WO 2013/137753 | 9/2013 |
| WO | WO 2013/137757 | 9/2013 |
| WO | WO 2013/148754 | 10/2013 |
| WO | WO 2013/148901 | 10/2013 |
| WO | WO 2013/172722 | 11/2013 |
| WO | WO 2013/179181 | 12/2013 |
| WO | WO 2014/007659 | 1/2014 |

(56) References Cited

FOREIGN PATENT DOCUMENTS

| WO | WO 2014/111828 | 7/2014 | | |
|----|----|----|----|----|
| WO | WO 2014/140278 | 9/2014 | | |
| WO | WO 2014/283834 | 9/2014 | | |
| WO | WO 2014/196875 | 12/2014 | | |
| WO | WO 2015/033288 | 3/2015 | | |
| WO | WO-2015033288 A1 * | 3/2015 | ........ | A61M 16/0003 |
| WO | WO 2015/174864 | 11/2015 | | |
| WO | WO 2016/063172 | 4/2016 | | |
| WO | WO 2016/079703 | 5/2016 | | |
| WO | WO 2016/157106 | 10/2016 | | |
| WO | WO 2017/187390 | 11/2017 | | |

OTHER PUBLICATIONS

Caring for Premature Baby (Accessed on Nov. 23, 2019) (Priority Date—Oct. 27, 2014) (Year: 2014).

De Luca et al., Effect of Amplitude and Inspiratory Time in a Bench Model; Pediatric Pulmonology (2012); Copyright 2012 Wiley Periodicals, Inc.; 7 pages.

De Luca et al., Noninvasive high frequency oscillatory ventilation; Intensive Care Med (2010); Published Sep. 21, 2010; 7 pages.

Diblasi et al., Noninvasive Respiratory Support Junenile Rabbits, vol. 67, No. 6, 2010, Pediatric Research; 6 pages.

Diblasi et al., Effective gas exchange paralysed juvenile rabbits, Apr. 7, 2010; Pediatric Research; 26 pages.

Georgia State University, Ohm's Law-Poiseuille's Law, Hyperphysics, http://hyperphysics.phy-astr-gsu-edu/hbase/electric/watcir2.html, Dec. 6, 2007.

Lim, M. W. et al., 'Relationship of inspiratory and expiratory times to upper airway resistance during pulsatile needle cricothyrotomy ventilation with generic delivery circuit', British Journal of Anaesthesia, 2010, V104(1), pp. 98-107.

Meraz, E. et al., 'Modeling Human Respiratory Impedance in Hispanic Asthmatic Children', Proceedings of the 29th Annual International Conference of the IEEE EMBS, Aug. 23-26, 2007, pp. 4251-4254.

Nguyen, T-U. et al., 'A Study of IOS Data Using the aRIC+IP Model of Respiratory Impedance', 31st Annual International Conference of the IEEE EMBS, Sep. 2-6, 2009, pp. 2875-2878.

Ohm's Law-Poiseuille's Law, Dec. 6, 2007 Hyperphysics, Georgia State University, http:hyperphysics.phy-astr.gsu.edu/hbase/electric/watcir2.html (Year: 2007).

International Search Report and Written Opinion for PCT/NZ2015/050062 mailed Aug. 7, 2015, in 18 pages.

International Search Report and Written Opinion for PCT/IB/2017/052457, dated Nov. 2, 2017 in 31 pages.

Summary of objections for European Application No. 14841727.2 dated Dec. 12, 2019 in 6 pages.

Summons to attend oral proceedings for European Application No. 14841727.2 dated Dec. 12, 2019 in 2 pages.

* cited by examiner

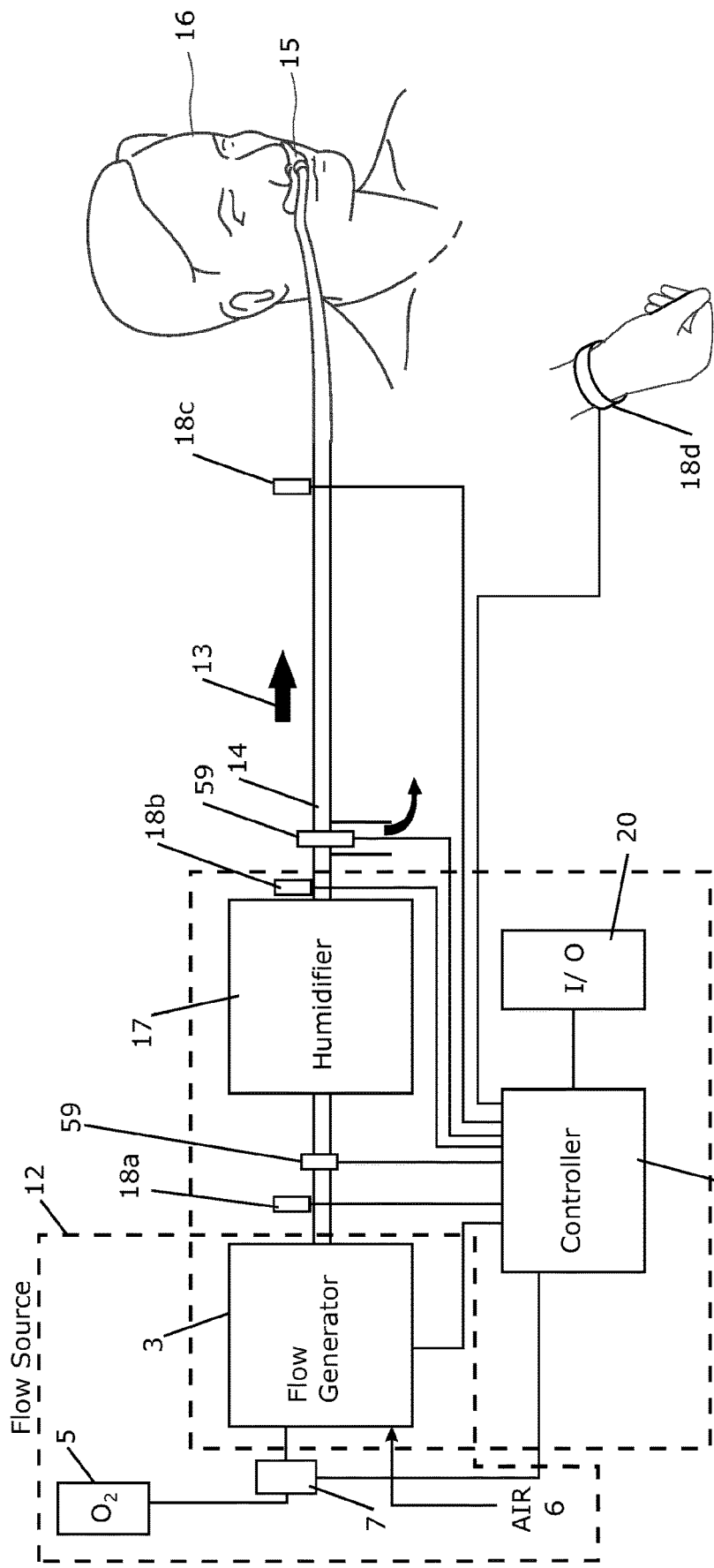
*FIGURE 1*
*FIGURE 1A*
*FIGURE 1B*

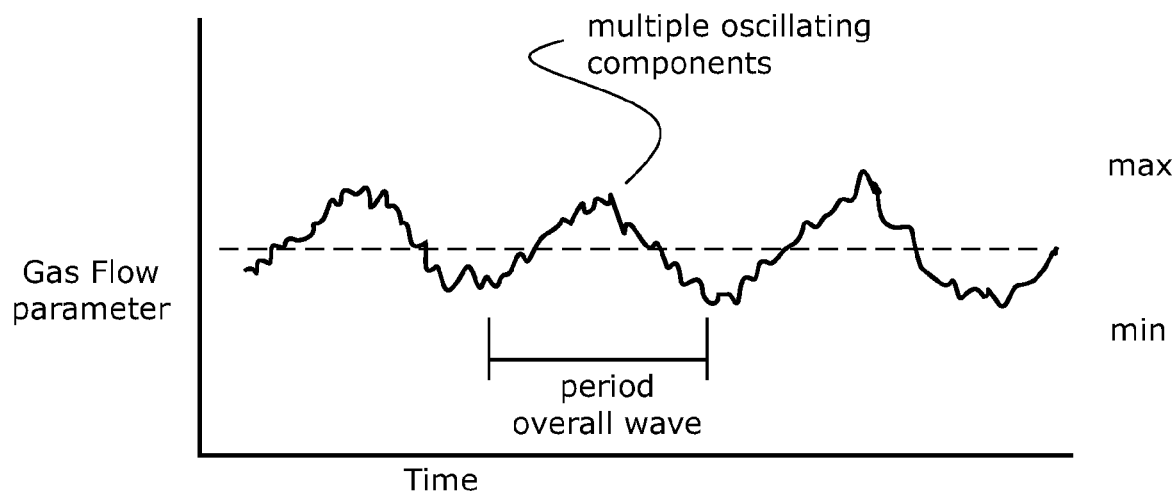
FIGURE 3E
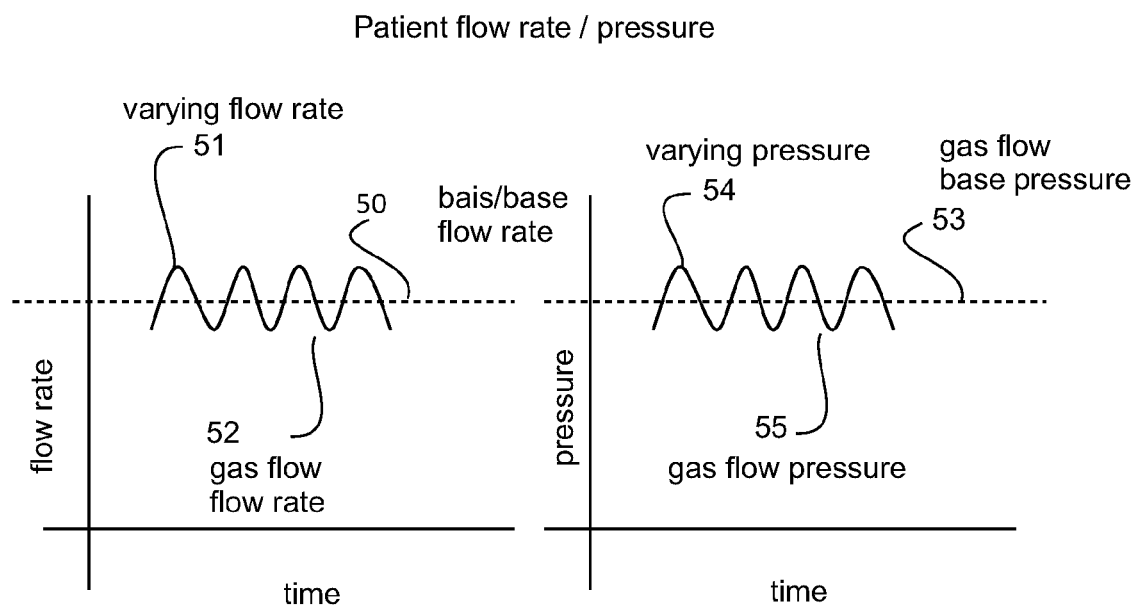
FIGURE 3F  FIGURE 3G

METHODS AND APPARATUS FOR OXYGENATION AND/OR CO2 REMOVAL

FIELD OF THE INVENTION

The present invention relates to methods and apparatus for oxygenation and/or CO2 removal for a patient, in relation to anaesthesia or more generally medical procedures where respiratory function might be compromised.

BACKGROUND TO THE INVENTION

Patients may lose respiratory function during anaesthesia, or sedation, or more generally during certain medical procedures. Prior to a medical procedure a patient may be pre-oxygenated by a medical professional to provide a reservoir of oxygen saturation, and this pre-oxygenation is generally carried out with a bag and a face mask. Once under general anaesthesia, patients must be intubated to ventilate the patient. In some cases, intubation is often completed in under 60 seconds, but in other cases, particularly if the patient's airway is difficult to traverse (for example, due to cancer, severe injury, obesity or spasm of the neck muscles), intubation will take significantly longer. While pre-oxygenation provides a buffer against declines in oxygen saturation, for long intubation procedures, it is necessary to interrupt the intubation process and reapply the face mask to increase the patient's oxygen saturation to adequate levels. The interruption of the intubation process may happen several times for difficult intubation processes, which is time consuming and can potentially put the patient at risk. After approximately three attempts at intubation the medical procedure will be abandoned.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

Disclosed is a method of oxygenation and/or CO2 clearance of a patient during a medical procedure with diminished or risk of diminished respiratory drive comprising operating a flow source to deliver an oscillating gas flow to the patient.

It is therefore an object of one or more of the disclosed embodiments to oxygenation and/or CO2 removal for a patient in relation to medical procedures (including anaesthesia) and/or to at least provide the public with a useful choice.

In the context of this specification "heart activity" is that which may be depicted as a waveform of its electrical impulses or the pulsatile arterial/venous pressure generated by the beating heart. Furthermore, in this specification, cardiogenic oscillations refer to the movement of gas caused by the activity of the heart, and it is understood that references to measuring heart activity include measurements of cardiogenic oscillations, for example by a flow sensor.

A gas flow modulator comprising: a gas inlet for inlet gas flow, a gas outlet for outlet oscillating gas flow, a control signal input for receiving a control signal with at least one oscillating component, a controllable valve or other device controlled by a control signal received on the control signal input for varying the inlet gas flow to provide the outlet oscillating gas flow, wherein the gas flow modulator is adapted for coupling to or within a breathing apparatus system to oscillate the gas flow produced by or within the breathing apparatus system.

Optionally the gas flow modulator further comprises a controller or an interface for a controller to receive control signals for controlling the valve.

Optionally the control signal comprising at least one oscillating component, and preferably a plurality of oscillating components.

Optionally the gas flow modulator further comprises a housing for housing the valve.

Optionally the gas flow modulator further comprises a pressure sensor for sensing a pressure of the outlet oscillating gas flow and/or for connecting to a port for sensing a pressure of one or more nostrils of a patient.

Optionally the gas flow modulator further comprises a flow sensor for sensing the outlet oscillating gas flow flow rate.

Optionally the gas flow modulator further comprises a pressure relief valve.

The pressure relief valve may be in fluid communication with the controllable valve.

Optionally the controllable valve is a proportional valve.

Optionally the gas flow modulator further comprises a user interface.

Optionally the gas flow modulator further comprises a muffler

In one aspect the present invention may comprise an apparatus for oxygenation and/or CO2 clearance of a patient, comprising: a flow source or a connection for a flow source for providing a gas flow, a gas flow modulator, a controller to control the gas flow, wherein the controller is operable to: receive input relating to heart activity and/or trachea gas flow of the patient, and control the gas flow modulator to provide a varying gas flow with at least two oscillating components, wherein one oscillating component has a frequency based on the heart activity and/or trachea flow of the patient, and one oscillating component has a frequency to: promote bulk gas flow movement, or promote mixing.

Optionally the controller is operable to control the gas flow modulator to provide a varying gas flow with a third oscillating component with a frequency to: promote bulk gas flow movement, or promote mixing.

Optionally the frequency to promote bulk gas flow movement is lower than the frequency based on heart activity and/or trachea flow of the patient.

Optionally the frequency to promote mixing is higher than the frequency based on heart activity and/or trachea flow of the patient.

Optionally the apparatus: comprises a heart activity sensor or has input for receiving input from a heart activity sensor, and/or comprises memory for storing heart activity information, wherein the controller receives input relating to heart activity from the sensor, input and/or memory, and/or comprises a flow sensor or has input for receiving input from a flow sensor.

Optionally the frequency to promote bulk gas movement is based on a body cavity resonance, and the controller is operable to receive input relating to a body cavity resonance.

Optionally the apparatus: comprises a body cavity sensor or has input for receiving input from a body cavity sensor, and/or comprises memory for storing body cavity information, wherein the controller receives input relating to a body cavity from the sensor, input and/or memory, and/or comprises a flow sensor or has input for receiving input from a flow sensor.

Optionally: the body cavity is a lung and the body cavity sensor is a lung cavity resonance sensor, and/or the body cavity is a chest cavity and the body cavity sensor is a chest cavity resonance sensor.

Optionally a first oscillating component with a frequency based on heart activity is about 0.1 Hz to about 3 Hz Optionally a second oscillating component with a frequency for bulk gas flow movement is about 0.05 Hz to about 5 Hz.

Optionally a third oscillating component with a frequency to promote mixing is about 3.5 Hz to about 150 Hz.

Optionally further comprising a base component.

Optionally the varying gas flow has an overall waveform comprising all the oscillating and/or base components with a period of about 0.3 seconds to about 15 seconds.

Optionally each component is a flow rate component.

Optionally the apparatus further comprising a base flow rate component, wherein the base flow rate is about 375 litres/min to 0 litres/min, or about 150 litres/min to about 0 litres/min, or is preferably about 120 litres/min to about 15 litres/min, or is more preferably about 90 litres/min to about 30 litres/min.

Optionally the apparatus is for use on persons greater than about 30 kg.

Optionally the gas flow modulator is a valve after the flow source, the controller being operable to control the valve to provide an oscillating gas flow.

Optionally the controller is operable to control the gas flow modulator to provide a varying gas flow with one or more oscillating components with a frequency and/or phase based on the heart activity.

Optionally the gas flow modulator is one or more of: an underwater pressure, release valve, oscillatable diaphragm, in-line linear actuator, flow chopper, aerodynamic or mechanical flutter valve, proportional valve (optionally including a proportional valve with a variable size orifice, variable based on an electrical signal).

Optionally the apparatus is adapted to provide gas flow to a patient via a patient interface, either non-sealing or sealing.

Optionally the apparatus is adapted to provide gas flow to a patient via a non-sealing cannula.

In another aspect the present invention may comprise a method for oxygenation and/or CO2 clearance of a patient, during a medical procedure, comprising: delivering a varying gas flow via a nasal interface to the patient by varying the gas flow at one or more frequencies during the procedure while the patient is apnoeic for at least a portion of the procedure and/or the patient is under anaesthesia causing diminished or risk of diminished respiratory function.

In another aspect the present invention may comprise a method for oxygenation and/or CO2 clearance of a patient, comprising: delivering a varying gas flow with at least two oscillating components, wherein: one oscillating component has a frequency based on heart activity and/or trachea flow of the patient, and one oscillating component has a frequency to: promote bulk gas flow movement, or promote mixing.

Optionally the method further comprising delivering a varying gas flow with a third oscillating component with a frequency to: promote bulk gas flow movement, or promote mixing.

Optionally there is a first oscillating component with a frequency based on heart activity is about 0.1 Hz to about 3 Hz Optionally a second oscillating component with a frequency for bulk gas flow movement is about 0.05 Hz to about 5 Hz Optionally a third oscillating component with a frequency to promote mixing is about 3.5 Hz to about 150 Hz.

In accordance with at least one of the embodiments disclosed herein there is a method of oxygenation and/or CO2 clearance of a patient during a medical procedure with diminished or risk of diminished respiratory drive comprising operating a flow source to deliver an oscillating gas flow to the patient.

In accordance with at least one of the embodiments disclosed herein the pressure and/or flow rate of the gas flow is oscillated.

The gas flow may: oscillates at a frequency between 2 to 200 HZ, has a flow rate amplitude of up to 200 L per min has a pressure amplitude of up to 50 cmH20, and/or has a waveform shape or one or more of: sinusoidal square triangular, and/or saw tooth.

The oscillation may be delivered and/or determined by patient respiratory phase.

The gas flow may be oscillated at a frequency(ies) based on or to match one or more of: patient's heart activity patient's lung's resonant frequency, random noise, patient's chest wall movement, patient's diaphragm muscle, contraction patient's neuron firing, respiratory activity CO2 level.

Also disclosed is a method of oxygenation and/or CO2 clearance of a patient during a medical procedure with diminished or risk of diminished respiratory drive comprising operating a flow source to deliver a constant, varying, oscillating, switching flow of gas flow to the patient.

Also disclosed is an apparatus for oxygenation and/or CO2 clearance of a patient during a medical procedure with diminished or risk of diminished respiratory drive, comprising: a flow source, a controller to control the flow source to provide: an oscillating gas flow to a patient during a medical procedure, and/or a constant, varying, oscillating, switching jet of gas flow to the patient during a medical procedure.

The pressure and/or flow rate of the gas flow may be oscillated.

The gas flow may: oscillates at a frequency between 2 to 200 HZ, has a flow rate amplitude of up to 200 L per min, has a pressure amplitude of up to 50 cmH20, and/or has a waveform shape or one or more of: sinusoidal, square, triangular, and/or saw tooth.

The oscillation may be delivered and/or determined by patient respiratory phase.

The gas flow is oscillated at a frequency(ies) based on or to match one or more of: patient's heart activity, patient's lung's resonant frequency, random noise, patient's chest wall movement, patient's diaphragm muscle contraction, patient's neuron firing.

The gas flow may be delivered by one or more of: a nasal cannula, Endotrachael tube, other anaesthetic equipment.

Further disclosed is a patient interface with nasal prongs with a diameter that is configurable.

The gas flow may be delivered by the patient interface of the configurations described herein, wherein the prongs are configured by the controller.

In accordance with at least one of the embodiments disclosed herein there is an apparatus according to the various embodiments of configurations described herein further comprising a connector for connecting the flow source interchangeably between a patient interface and a large bore needle.

In accordance with at least one of the embodiments disclosed herein there is a system for providing an oscillatory flow of gases that matches the heart beats, comprising: a flow source generator and a controller to influence the flow or parameters or characteristics of the flow such that, in-use, the gases supplied to a user are substantially matched to those of the user's heart beat.

In accordance with at least one of the embodiments disclosed herein there is a method of matching a flow of gases to a user's heart beat, comprising: measuring or determining the user's heart beat and adjusting or controlling the flow of gas from a source being supplied to the user.

In accordance with at least one of the embodiments disclosed herein there is an apparatus for oxygenation and/or $CO_2$ clearance of a patient, comprising: a flow source or a connection for a flow source for providing a gas flow, a gas flow modulator, a controller to control the gas flow, wherein the controller is operable to: receive input relating to heart activity and/or trachea flow of the patient, and control the gas flow modulator to provide a varying gas flow with one or more oscillating components with a frequency or frequencies based on the heart activity and/or trachea flow of the patient.

The apparatus may: comprise a heart activity sensor or has input for receiving input from a heart activity sensor, and/or comprises memory for storing heart activity information, wherein the controller receives input relating to heart activity from the sensor, input and/or memory, and/or comprises a flow sensor or has input for receiving input from a flow sensor.

The apparatus may be an apparatus for providing nasal high flow and/or the apparatus may comprises or be for use with a high flow nasal cannula.

The varying gas flow may have an oscillating flow rate and the controller controls the gas flow modulator to provide the varying gas flow with an oscillating flow rate of: about 375 litres/min to about 0 litres/min, or preferably of about 240 litres/min to about 7.5 litres/min, or more preferably of about 120 litres/min to about 15 litres/min.

The oscillating flow rate may comprise a base flow rate component, wherein the base flow rate is about 375 litres/min to 0 litres/min, or about 150 litres/min to about 0 litres/min, or is preferably about 120 litres/min to about 15 litres/min, or is more preferably about 90 litres/min to about 30 litres/min.

The apparatus may be for use on persons greater than about 30 kg.

The oscillating flow rate may comprise a base flow rate component, wherein the base flow rate is about 0.5 litres/min to about 25 litres/min.

The oscillating flow rate comprises a base flow rate component, wherein the base flow rate is in the range of 0.4 litres/min per patient kilogram to 0.8 litres/min per patient kilogram.

The apparatus may be for use on persons within about 0.3 to 30 kilograms.

The oscillating flow rate may comprise a base flow rate component, wherein the base flow rate is about 8 litres/min for person under about 2 kilograms.

The gas flow modulator may be a flow generator and the flow source comprises the flow generator, the controller being operable to control the flow generator to provide an oscillating gas flow.

The gas flow modulator may be a valve after the flow source, the controller being operable to control the valve to provide an oscillating gas flow.

The controller may be operable to control the gas flow modulator to provide a varying gas flow with one or more oscillating components with a frequency and/or phase based on the heart activity.

The relative phase may be either a) in phase with the heart activity, b) in anti-phase with the heart activity, or c) is an arbitrary phase.

The heart activity may have one or more frequencies, and the controller is operable to control the gas flow modulator to provide an oscillating gas flow with one or more oscillating components with a frequency or frequencies different to those of the heart activity.

The heart activity may have one or more frequencies, and the controller is operable to control the gas flow modulator to provide an oscillating gas flow with one or more oscillating component with a frequency or frequencies corresponding to those of the heart activity.

The varying gas flow may have an oscillating flow rate comprising at least two flow rate components with respective frequencies, wherein a first flow rate component provides bulk gas flow at a frequency corresponding to a breath rate of a patient, and a second flow rate component has a different frequency.

The gas flow modulator may be one or more of: an underwater pressure release valve, oscillatable diaphragm, in-line linear actuator, flow chopper, aerodynamic or mechanical flutter valve, proportional valve (optionally including a proportional valve with a variable size orifice, variable based on an electrical signal).

The gas flow modulator may be before, in or after the flow source.

The gas flow may have an oxygen fraction of 100%, or 30-40% or 40-50% or 60-70% or 80-90% or 90-100%.

The gas flow may have an oxygen fraction of at least about 21% and comprises one or more of nitrous oxide, nitric oxide and/or helium.

The gas flow may be air.

The apparatus may be adapted to provide gas flow to a patient via a patient interface, either non-sealing or sealing.

The apparatus may be adapted to provide gas flow to a patient via a non-sealing cannula.

The apparatus may comprise a humidifier to humidify the gas flow before or after it is oscillated.

The apparatus may additionally comprise one or more sensors for measuring one or more physiological parameters of a patient, and/or one or more inputs for receiving a signal from one or more sensors for measuring physiological parameters of a patient, wherein the one or more physiological parameters are one or more of: heart activity, oxygen saturation, partial pressure of oxygen in the blood, respiratory rate, partial pressure of $CO_2$ in the blood, exhaled $CO_2$.

The varying gas flow may an oscillating flow rate, and the varying gas flow and/or oscillating flow rate have one or more parameters, comprising one or more of: maximum flow rate, minimum flow rate, frequency period, and the varying gas flow and/or oscillating flow rate parameters are set by the controller based on user input and/or automatically from measurements of patient physiological functions and patient physiological parameters.

The controller may be adapted to receive input relating to exhaled $CO_2$ and utilise that to control the gas flow.

In accordance with at least one of the embodiments disclosed herein there is an apparatus for oxygenation and/or $CO_2$ clearance of a patient, during a medical procedure, comprising: a flow source or a connection for a flow source for providing a gas flow, a gas flow modulator, a controller to control the gas flow by controlling the gas flow modulator to provide an varying gas flow with one or more frequencies, wherein during the procedure the patient is apnoeic for at least a portion of the procedure and/or the patient is under anaesthesia causing diminished or risk of diminished respiratory function.

The varying gas flow may have an oscillating flow rate and the controller controls the gas flow modulator to provide the varying gas flow with an oscillating flow rate of: about 375 litres/min to about 0 litres/min, or preferably of about 240 litres/min to about 7.5 litres/min, or more preferably of about 120 litres/min to about 15 litres/min, and/or the oscillating flow rate has one or more frequencies of about 0.1 Hz to about 200 Hz, and preferably about 0.1 Hz to about 3 Hz, and more preferably about 0.5 Hz to about 3 Hz.

The oscillating flow rate may comprise a base flow rate component, wherein the base flow rate is about 375 litres/min to 0 litres/min, or 150 litres/min to about 0 litres/min, or is preferably about 120 litres/min to about 15 litres/min, or is more preferably about 90 litres/min to about 30 litres/min.

The oscillating flow rate may comprise a base flow rate component, wherein the base flow rate is about 0.2 litres/min per patient kilogram to about 2.5 litres/min per patient kilogram; and preferably is about 0.25 litres/min per patient kilogram to about 1.75 litres/min per patient kilogram; and more preferably is about 0.3 litres/min per patient kilogram to about 1.25 litres/min or about 1.5 litres/min per patient kilogram The apparatus may be for use on persons greater than about 30 kg.

In accordance with at least one of the embodiments disclosed herein there is a method for oxygenation and/or CO2 clearance of a patient, during a medical procedure, comprising: delivering a varying gas flow via a nasal interface to the patient by varying the gas flow at one or more frequencies during the procedure while the patient is apnoeic for at least a portion of the procedure and/or the patient is under anaesthesia causing diminished or risk of diminished respiratory function.

The varying gas flow may have an oscillating flow rate of: about 375 litres/min to about 0 litres/min, or preferably of about 240 litres/min to about 7.5 litres/min, or more preferably of about 120 litres/min to about 15 litres/min and/or the oscillating flow rate has one or more frequencies of about 0.1 Hz to about 200 Hz, and preferably about 0.1 Hz to about 3 Hz, and more preferably about 0.5 Hz to about 3 Hz.

The oscillating flow rate may comprise a base flow rate component, wherein the base flow rate is about 375 litres/min to 0 litres/min, or 150 litres/min to about 0 litres/min, or is preferably about 120 litres/min to about 15 litres/min, or is more preferably about 90 litres/min to about 30 litres/min.

The oscillating flow rate may comprise a base flow rate component, wherein the base flow rate about 0.2 litres/min per patient kilogram to about 2.5 litres/min per patient kilogram; and preferably is about 0.25 litres/min per patient kilogram to about 1.75 litres/min per patient kilogram; and more preferably is about 0.3 litres/min per patient kilogram to about 1.25 litres/min or about 1.5 litres/min per patient kilogram.

The method may be for a patient greater than about 30 kg.

The method may be for providing gas flow prior to the medical procedure.

The gas flow may have a flow rate, wherein a first flow rate provided prior to the medical procedure and a second flow rate is provided during the medical procedure, and optionally a third flow rate after the medical procedure.

The second flow rate may be greater than the first flow rate; and/or the third flow rate may be less than the second flow rate.

The method may have: the first flow rate being about 15 L/min to about 90 L/min, or about 20 L/min to about 80 L/min, or about 25 L/min to about 60 L/min, or about 30 L/min to about 50 L/min, or about 40 L/min, or about 30 L/min; and/or second flow rate being about 20 L/min to about 150 L/min, or about 40 L/min to about 120 L/min, or about 50 L/min to about 100 L/min, or about 60 L/min to about 80 L/min, or about 70 L/min, or about 60 L/min; and/or the third flow rate is less than about 90 L/min, or less than about 70 L/min, or less than about 50 L/min, or less than about 40 L/min, or less than about 20 L/min, or about 40 L/min, or about 30 L/min.

The controller may be adapted to receive input relating to exhaled CO2 and utilise that to control the gas flow.

The apparatus may be an apparatus for providing nasal high flow and/or the apparatus comprises or is for use with a high flow nasal cannula.

The method may comprise delivering nasal high flow therapy.

In accordance with at least one of the embodiments disclosed herein there is an apparatus for promoting gas exchange with a patient, comprising: a flow source or connection for a flow source for providing a gas flow, a gas flow modulator, a controller to control the gas flow, and wherein the controller is operable to control the gas flow modulator to provide a varying gas flow with a base gas flow component and at least one oscillating gas flow component with one or more frequencies of about 0.1 Hz to about 3 Hz.

The one or more oscillating gas flow components may have one or more frequencies of about 0.3 Hz to about 3 Hz.

The varying gas flow may have an oscillating flow rate and the controller controls the gas flow modulator to provide the varying gas flow with an oscillating flow rate of: about 375 litres/min to about 0 litres/min, or preferably of about 240 litres/min to about 7.5 litres/min, or more preferably of about 120 litres/min to about 15 litres/min.

The oscillating flow rate may comprise a base gas flow component, wherein the base flow rate is about 375 litres/min to 0 litres/min, or about 150 litres/min to about 0 litres/min, or is preferably about 120 litres/min to about 15 litres/min, or is more preferably about 90 litres/min to about 30 litres/min.

The oscillating flow rate may comprise a base gas flow component, wherein the base flow rate about 0.2 litres/min per patient kilogram to about 2.5 litres/min per patient kilogram; and preferably is about 0.25 litres/min per patient kilogram to about 1.75 litres/min per patient kilogram; and more preferably is about 0.3 litres/min per patient kilogram to about 1.25 litres/min or about 1.5 litres/min per patient kilogram.

The oscillating flow rate may comprise at least one oscillating flow rate component, wherein each oscillating flow rate is about 0.05 litres/min per patient kilogram to about 0.5 litres/min per patient kilogram; and preferably about 0.12 litres/min per patient kilogram to about 0.4 litres/min per patient kilogram; and more preferably about 0.12 litres/min per patient kilogram to about 0.35 litres/min per patient kilogram.

The apparatus may be for use on persons greater than about 30 kg.

The oscillating flow rate may comprise a base gas flow component, wherein the base flow rate component is about 0.5 litres/min to about 25 litres/min.

The oscillating flow rate may comprise a base gas flow component, wherein the base flow rate component in the range of 0.4 litres/min per patient kilogram to 0.8 litres/min per patient kilogram.

The oscillating flow rate may comprise at least one oscillating flow rate component, wherein each oscillating flow rate is in the range of 0.05 litres/min per patient kilogram to 2 litres/min per patient kilogram; and preferably in the range of 0.1 litres/min per patient kilogram to 1 litres/min per patient kilogram; and more preferably in the range of 0.2 litres/min per patient kilogram to 0.8 litres/min per patient kilogram.

The apparatus may be for use on persons within about 0.3 to 30 kilograms.

The base gas flow component may be a base flow rate component in the range, wherein the base flow rate is about 8 litres/min for person under about 2 kilograms.

The oscillating gas flow may have a plurality of oscillating gas flow components at a plurality of frequencies.

The apparatus may have one of more of the frequencies is about 0.1 HZ to about 3 Hz.

The apparatus may have oscillating gas flow has a period of about 0.3 to about 10 s.

The controller may be adapted to receive input relating to exhaled CO2 and utilise that to control the gas flow.

The apparatus wherein: if the resting heart rate is about 40 to about 100 bpm, the oscillation gas flow component has a frequency of about 0.67 to about 1.67 Hz, and if the heart rate is about 30 to about 180 bpm the oscillation gas flow component has a frequency of about 0.67 to about 0.5 to about 3 Hz).

The apparatus may be an apparatus for providing nasal high flow and/or the apparatus may comprises or be for use with a high flow nasal cannula "high flow therapy" may refer to the delivery of gases to a patient at a flow rate of between about 5 or 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For example, according to those various embodiments and configurations described herein, a flow rate of gases supplied or provided to an interface or via a system, such as through a flow path, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100 L/min, about 70 to 80 L/min).

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

"high flow therapy" may refer to the delivery of gases to a patient at a flow rate of between about 5 or 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For example, according to those various embodiments and configurations described herein, a flow rate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100 L/min, about 70 to 80 L/min).

According to another aspect of the invention a gas flow modulator is provided and comprises: an inlet manifold having a gas inlet for inlet gas flow; an outlet manifold having a gas outlet for outlet oscillating gas flow; and a gases connection conduit, which fluidly couples the inlet manifold to the outlet manifold, wherein the outlet manifold further comprises a controllable valve for varying the inlet gas flow to provide the outlet oscillating gas flow.

The inlet manifold and the outlet manifold may be spaced apart from each other.

The gas flow modulator may be adapted for coupling to or within a breathing apparatus system.

The gas flow modulator may further comprise a valve controller wherein the controllable valve is controlled by the valve controller.

The valve controller may comprise a control signal input module configured to receive a control signal with at least one oscillating component and wherein the controllable valve is controlled by the valve controller based on the control signal received on the control signal input module such that, in use, the gas flow modulator oscillates the gas flow produced by or within the breathing apparatus system.

The control signal input module may be configured to receive a control signal having at least one oscillating component that is synchronized with the heart beat or heart rate of the patient.

The control signal input module may be configured to receive a control signal having a plurality of oscillating components.

The plurality of oscillating components may comprise: a first oscillating component based on the heart activity of a patient; a second bulk movement oscillating component; and a third mixing turbulence oscillating component.

The first oscillating component may have an oscillation frequency of about 0.1 Hz to about 3 Hz. The second bulk movement oscillating component may have an oscillation frequency of about 0.05 Hz to about 5 Hz. The third mixing turbulence oscillating component may have an oscillation frequency of about 3.5 Hz to about 150 Hz.

The outlet manifold may comprise a pressure relief valve. The pressure relief valve may comprise a mechanical pressure relief valve.

The pressure relief valve may be configured to activate when the pressure in either the inlet manifold or the outlet manifold exceeds a predefined pressure threshold.

The outlet manifold may comprise an outlet filter/constrictor located between the controllable valve and the gas outlet.

The outlet manifold may comprise an outlet filter/constrictor located between the controllable valve and the pressure relief valve.

The outlet filter/constrictor may have a 40 μm pore size.

The outlet manifold may comprise a differential pressure sensor in fluid communication with two pressure taps, in which one of the pressure taps is in fluid communication with the passageway upstream of the outlet filter/constrictor and the other pressure tap is in fluid communication with the passageway downstream of the outlet filter/constrictor.

The outlet manifold may comprise a flow constrictor located between the controllable valve and the gas outlet.

The outlet manifold comprises a flow constrictor may be located between the controllable valve and the pressure relief valve.

The outlet manifold may comprise a filter located between the controllable valve and the flow constrictor.

The outlet manifold may comprises a differential pressure sensor in fluid communication with two pressure taps, in which one of the pressure taps is in fluid communication with the passageway upstream of the flow constrictor and the other pressure tap is in fluid communication with the passageway downstream of the flow constrictor.

The outlet manifold may comprise an outlet pressure sensing port located at, or near, the gas outlet.

The controllable valve may be a proportional valve.

The inlet manifold may comprise a pressure or flow regulator.

The flow regulator is configured to cap the flow through the gas flow modulator at a flow threshold.

The flow threshold may be 100 L/minute or up to 150 L/minute.

The inlet manifold may comprise a solenoid valve.

The inlet manifold may comprise an inlet filer positioned downstream of the gas inlet.

The inlet filer may be a sintered filter with a 15 μm pore size.

The gas flow modulator may comprise a modular manifold arrangement.

The inlet manifold and the outlet manifold may be separated by a coupling tube, in which the coupling tube connects the outlet of the inlet manifold with an inlet of the outlet manifold.

The coupling tube may be shaped to form an arcuate shape having a smooth sweep.

According to another aspect of the invention there is provided a flow constrictor for mounting in the flow path of a manifold of a gas flow modulator. The flow constrictor comprises: an elongate body; a central bore through the elongate body of the flow constrictor; a plurality of flow channels located on the exterior portion of the elongate body and extending in the general direction of the gases flow path; and a constriction feature located partway each of the flow channels.

The constriction feature may comprise a constriction rib.

The constriction feature may comprise a diffuser portion.

The leading edge of the flow constrictor may be aerodynamically shaped.

The elongate body of the flow constrictor may be generally cylindrical in shape and the flow channels extend in a generally axial direction.

The plurality of flow channels may be arranged substantially as a radial array formation around the cylindrically shaped elongate body.

A threaded fixture may be circumferentially located in the middle of the elongate body of the flow constrictor.

The diffuser portion may be provided at least partially by the threaded fixture.

The constriction rib may be located immediately upstream of the threaded fixture or diffuser portion.

The flow constrictor may be mounted in the flow path of a manifold of a gas flow modulator. The flow constrictor may be mounted downstream of a controllable valve for varying the inlet gas flow to the manifold to provide the outlet oscillating gas flow.

According to another aspect of the invention there is provided a gas flow modulator comprising a plurality of sub-manifolds. The gas flow modulator includes an inlet manifold. The gas flow modulator may include an outlet manifold. The gas flow modulator includes an inlet valve arrangement. The inlet valve arrangement may be included in the inlet manifold.

In one embodiment, the inlet valve arrangement may include two inlet lines. The inlet valve arrangement may include an oxygen inlet line. The inlet valve arrangement may include an air inlet line. The oxygen inlet line may supply a combined pipe or mixing chamber. The air inlet line may supply air to the combined pipe or mixing chamber.

The oxygen inlet line may include a proportional valve. The air inlet line may include a proportional valve. The proportional valves may operate to control the amount of air/oxygen that is delivered into a combined pipe or a mixing chamber.

A flow sensor may be provided on the oxygen inlet line. A flow sensor may be provided on the air inlet line. The flow sensors may provide feedback control to the proportional valves to maintain the concentration of oxygen in the air/oxygen mixture.

The proportional valves may operate to create oscillations in the gases flowing through the individual inlet lines. The proportional valves may include additional control lines from a controller to control the opening and closing of the proportional valves based on an oscillation signal.

A relief valve may be provided in the combined pipe or mixing chamber.

Each of the oxygen inlet line and the air inlet line may include a priming unit. The priming unit may include one or more of: a filter 642; a one-way valve; an over-pressure valve; and a regulator. The regulator may be a flow regulator. The regulator may be a pressure regulator.

In another embodiment, the inlet valve arrangement may include an oxygen inlet line and air inlet line. The oxygen and air from the two inlet lines may be mixed in a combined pipe. The two inlet lines and combined pipe may be included in the inlet manifold.

The oxygen inlet line and the air inlet line may each include a respective proportional valve. The proportional valve of the oxygen inlet line may be controlled based on an oxygen sensor that measures the concentration of oxygen. The proportional valve of the air inlet line may be controlled based on a flow sensor. The proportional valve may control the air supplied thought the air inlet line based on a signal from the flow sensor. The proportional valves may be controlled to create oscillations in the flow.

A relief valve and/or a priming unit may be provided in the combined pipe or mixing chamber.

In another embodiment, the inlet valve arrangement may include an oxygen inlet line. The oxygen inlet line may include a proportional valve. The oxygen inlet line may be included in the inlet manifold.

The proportional valve may be controlled based on an oxygen sensor and a flow sensor.

The inlet valve arrangement may include a venturi arrangement. The venturi arrangement may include a filter. The venturi arrangement may include a one-way valve. The venturi arrangement may draw in additional air as the flow rate of oxygen increases. The venturi arrangement may act as a passive air flow controller.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIG. 1 illustrates an apparatus/system for oxygenating a patient and/or CO2 removal with high flow gas in relation to anaesthesia.

FIG. 1A schematically illustrates a nasal cannula with adjustable diameter prongs.

FIG. 1B illustrates a large bore needle for flow.

FIGS. 3A to 3G illustrate a varying gas flow with oscillating parameters, such as pressure and flow rate.

DETAILED DESCRIPTION OF PREFERRED EMBODIMENTS

1. Overview of Embodiments and Examples

Figure 1C:
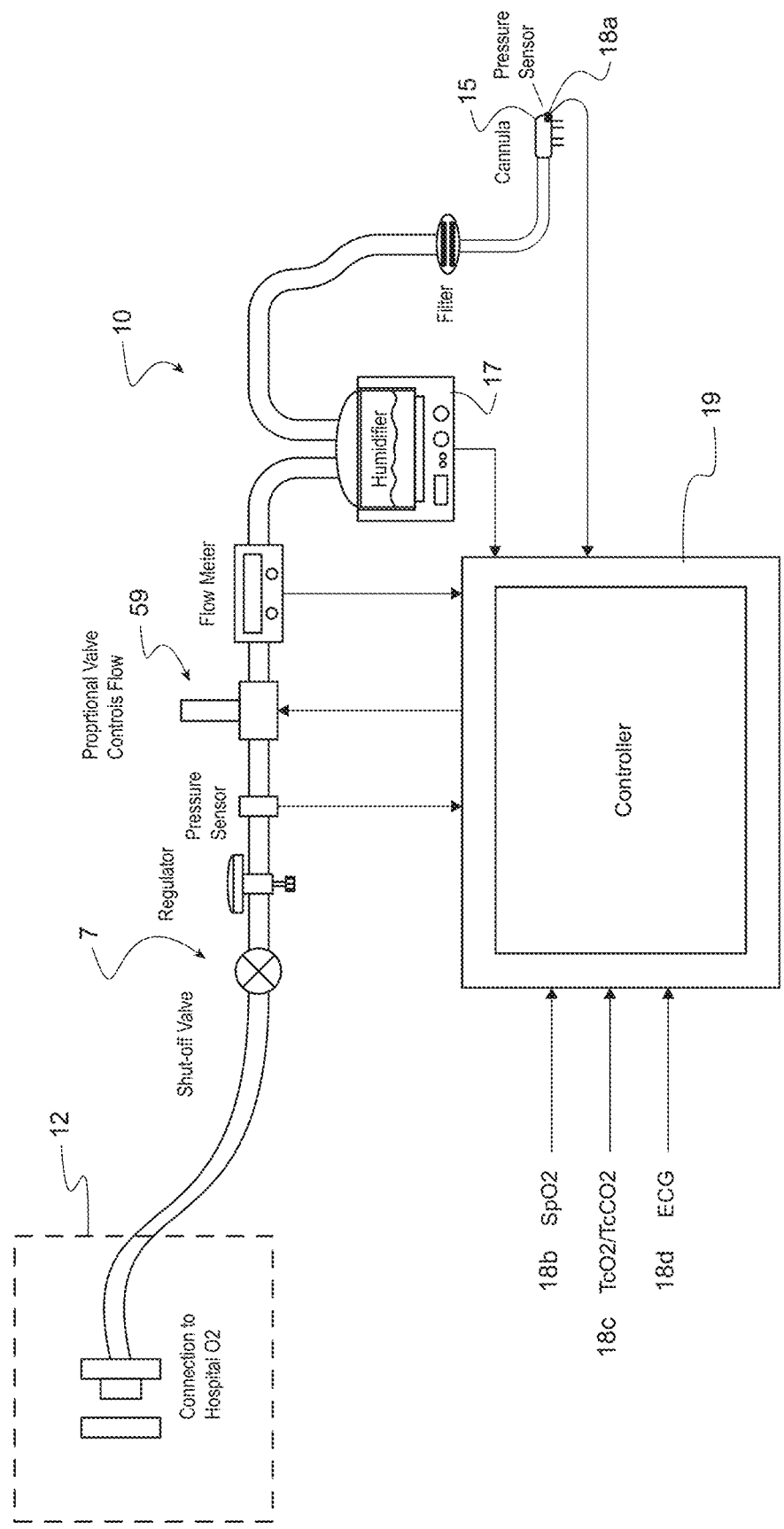
FIG. 1C illustrates a variation of an apparatus/system for oxygenating a patient and/or CO2 removal with high flow gas in relation to anaesthesia.

In general terms, apparatus and methods described herein relate to flow therapy methods and apparatus that assist oxygenation and/or CO2 removal in a respirating patient (respirating referring to either spontaneous or assisted respiration), and preferably during anaesthesia, and/or during resuscitation, and/or at any medical procedure or other time that assistance is required. Flow therapy (also termed high flow therapy) relates to apparatus and methods that deliver relatively high flows of gas to assist a patient respiration.

Some apparatus and methods described herein vary the gas flow to generate a varying gas flow with gas flow oscillations. This assists with CO2 removal, and also can assist with oxygenation of a patient. For example, parameter(s) of the delivered varying high flow of gas are adjusted to oscillate those parameter(s) to provide a varying gas flow. For example, the pressure and/or flow rate of a delivered high flow of gas is oscillated. In some embodiments, the oscillations are based on (such as correspond to, or are synchronised with) or are otherwise determined using, one or more of: the resonant frequency of patient lungs and/or chest wall, patient cardiogenic pulsations, patient diaphragm contraction, patient brain activity, patient breathing rate, partial pressures of CO2 or O2, exhaled CO2 or the like and also using other suitable sensed physiological parameters. Such methods and apparatus can be utilised when the patient is apnoeic or otherwise has diminished respiratory function, either during a medical procedure or otherwise. To provide additional efficacy, optionally the patient's oxygenation requirements can be determined and gas flow oscillations can be adjusted accordingly to improve oxygenation, and/or the patient's CO2 can be sensed to assist with determining how to vary the gas flow with gas flow oscillations to remove CO2. As will be described, it has been determined that providing gas flow oscillations in a varying high flow gas flow assists with/improves CO2 removal. Apnoea can occur due to, for example, respiratory depression from anaesthesia (or a variety of other causes), such that the patient stops breathing.

1.1 Oxygenation and/or CO2 Removal Using Varying Gas Flow

In methods and apparatus described herein, a varying gas flow can be provided, the varying gas flow being oscillated to create an oscillating gas flow comprising a base gas flow component and one or more oscillating gas flow components. The varying gas flow with gas flow oscillations would be useful when a patients' respiratory drive is compromised or at least reduced, whether this is before, during or after a medical procedure or in any other situation. The varying gas flow with oscillating components predominantly assists to remove CO2 from a respiring patient. CO2 removal can be useful when a patient is apnoeic, or when a patient has diminished respiratory function, such as when sedated or descending into or coming out of anaesthesia. During these events, a patient's respiratory function might not be good enough to sufficiently clear CO2 unassisted. There can be other situations where CO2 removal assistance is desirable also. As will be described, it has been determined that providing oscillations in a varying gas flow assists with/ improves CO2 removal.

Varying the gas flow with oscillating components can also help to oxygenate the patient both directly by assisting the delivery of oxygen and indirectly by removing CO2.

Particular embodiments and examples of apparatus/systems and methods are described for altering the parameters of high gas flow oxygenation. At least some of those embodiments can assist CO2 removal from a patient by gas delivery, for example during a medical procedure (such as anaesthesia). Embodiments described are particularly (but not solely) useful for patients that are not spontaneously breathing. When a patient is not spontaneously breathing, their ability to oxygenate and clear CO2 can be diminished. Some embodiments relate to apparatus and methods of oxygenation and/or CO2 removal. In general terms, the embodiments relate to methods and apparatus of utilising a high flow source of gas (such as oxygen and/or other gas mixes) for oxygenating a patient, and/or methods and apparatus that facilitate removal of CO2.

2. First Embodiment of Apparatus/Method for Assisting with CO2 Removal and/or Oxygenation 2.1 Apparatus for Assisting with CO2 Removal and/or Oxygenation Using Varying Gas Flow FIG. 1 shows a system/apparatus 10 for delivering a varying gas flow with oscillations (oscillating gas flow) to a patient to assist with CO2 removal, and which can also to assist with oxygenation, in the situations described above.

The system/apparatus 10 could be an integrated or a separate component based arrangement, generally shown in the dotted box 11 in FIG. 1. In some configurations the system 10 could be a modular arrangement of components. Hereinafter it will be referred to as system, but this should not be considered limiting.

The apparatus comprises a flow source 12 for providing a high flow gas such as oxygen, or a mix of oxygen and one or more other gases. Alternatively, the apparatus can have a connection for coupling to a flow source. As such, the flow source might be considered to form part of the apparatus 10 or be separate to it, depending on context, or even part of the flow source forms part of the apparatus, and part of the flow source fall outside the apparatus.

The flow source could be an in-wall supply of oxygen, a tank of oxygen, a tank of other gas and/or a high flow therapy apparatus with a blower/flow generator 3. FIG. 1 shows a flow source with a flow generator 3, with an optional air inlet 6 and optional connection to an O2 source 5 (such as tank or O2 generator) via a shut off valve and/or regulator and/or other gas flow control (all represented as 7), but this is just one option. In an alternative in FIG. 1C, there is no flow generator, but rather the flow source 12 is an in-wall O2 or blended O2/Air supply, optionally with a flow meter. A shut off valve, regulator and pressure sensor arrangement 7 is also shown. The description from here can refer to either embodiment. The flow source could be one or a combination of a flow generator, O2 source, air source as described. Any valves associated with the flow source 12 could be considered part of the flow source, or external to it, depending on context. The flow source is shown as part of the system 10, although in the case of an external oxygen tank or in-wall source, it may be considered a separate component, in which case the apparatus has a connection port to connect to such flow source. The flow source 12 provides a (preferably high) flow of gas 13 that can be delivered to a patient 16 via a delivery conduit 14, and patient interface 15 (such as a (non-sealing) nasal cannula or sealing nasal mask). The flow source could provide a base gas flow rate of between, e.g., 0.5 litres/min and 375 litres/min, or any range within that range, or even ranges with higher or lower limits. Details of the ranges and nature of flow rates will be described later.

A humidifier 17 can optionally be provided between the flow source and the patient to provide humidification of the delivered gas. One or more sensors 18a, 18b, 18c, 18d, such as flow, oxygen fraction, pressure, humidity, temperature or other sensors can be placed throughout the system and/or at, on or near the patient 16. Alternatively, or additionally, sensors from which such parameters can be derived could be used. In addition, or alternatively, the sensors 18a-18d can be one or more physiological sensors for sensing patient physiological parameters such as, heart rate, oxygen saturation, partial pressure of oxygen in the blood, respiratory rate, partial pressure of CO2 in the blood. Alternatively or additionally, sensors from which such parameters can be derived could be used. Other on patient sensors could comprise EEG sensors, torso bands to detect breathing, and any other suitable sensors. In some configurations the humidifier may be optional or it may be preferred due to the advantages of humidified gases helping to maintain the condition of the airways. One or more of the sensors might form part of the apparatus, or be external thereto, with the apparatus having inputs for any external sensors.

The output from the sensors is sent to a controller to assist control of the apparatus, including among other things, to vary gas flow to provide an oscillating gas flow.

As an example, the sensors can comprise a pulse oximeter 18d on the patient for determining the oxygen saturation the blood. The pulse oximeter provides an analogue or digital electrical signal for the controller 19.

As another example, the partial pressure of oxygen in the blood could be sensed by using a transcutaneous oxygen monitor (sensor). The oxygen sensor measures the concentration of oxygen and this reading is corrected for temperature to produce an estimated partial pressure for oxygen in the blood. The instrument electronic system provides an analogue or digital signal which directly indicates the partial pressure of blood oxygen, and which is connected to the controller 19.

As another example, respiratory rate could be sensed using respiratory inductance plethysmography (RIP) with an analogue or digital signal that is connected to the controller 19.

As another example, the partial pressure of CO2 in the blood can be sensed using a transcutaneous monitor with an analogue or digital signal that is connected to the controller 19.

As another example, exhaled CO2 is sensed using an exhaled CO2 sensor. The CO2 partial pressure reading is transmitted to the controller in either analogue or digital form.

Another example is a heart activity sensor for sensing patient heart activity. The controller 19 is connected to receive input from the heart activity sensor (such as a sensor output signal) relating to heart activity of the patient. This enables the controller to control gas flow based on the received input from the heart activity sensor.

A controller 19 is provided, which is coupled to the flow source 12, humidifier 17 and sensors 18*a*-18*d*. It controls these and other aspects of the apparatus to be described below.

The apparatus also comprises one or more gas flow modulators 59, which can be used to modulate (that is, varying, modify, adjust or otherwise control parameters of the gas flow). Each gas flow modulator can be provided in the flow source (and the flow source itself can be a gas flow modulator), after the flow source and before the humidifier, after the humidifier, and/or in any other suitable place in the apparatus to modulate gas flow path. Examples are shown in FIGS. 1 and 1B, but not all are required, and their position and number can vary based on the requirements of the system. Other examples are described later with reference to FIGS. 4 to 11. Types of gas flow modulators will be described later.

The controller 19 can operate the flow source to provide the delivered flow of gas. It can also operate the gas flow modulator(s) (including the flow source) to control the flow, pressure, volume and/or other parameters of gas provided by the flow source based on feedback from sensors, or optionally without feedback (e.g. using default settings). The controller can also control any other suitable parameters of the flow source to meet oxygenation requirements and/or CO2 removal. The controller 19 can also control the humidifier 17 based on feedback from the sensors 18*a*-18*d*. Using input from the sensors, the controller can determine oxygenation requirements and control parameters of the flow source, gas flow modulator(s) and/or humidifier as required. An input/output interface 20 (such as a display and/or input device) is provided. The input device is for receiving information from a user (e.g. clinician or patient) that can be used for determining oxygenation requirements and/or CO2 detection.

2.2 CO2 Removal and/or Oxygenation Using Varying Flow

Use of the apparatus will now be described.

A high flow gas delivered by a high flow therapy method or apparatus comprises various components with one or more parameters that can be adjusted, including being adjusted to oscillate. Each parameter might be adjusted independently, or in dependence on other parameters. This provides a varying gas flow (varying gas flow parameters). The varying gas flow (with oscillations) assists CO2 removal and can assist oxygenation.

In one embodiment, the controller 19 is configured to vary the gas flow to create an oscillating gas flow to improve CO2 removal (and optionally improve oxygenation). This could be used either during pre-oxygenation or during anaesthesia, or during any other medical procedure where the patient is apnoeic or otherwise where respiratory function might be diminished. To generate the oscillating gas flow, a parameter or parameters of the delivered gas flow are oscillated, with one or more frequencies, amplitudes and/or phases. For example, and typically, the flow rate of the gas flow is oscillated with one or more frequencies (including a phase and amplitude), which in turn oscillates the pressure generated by the delivered gas flow. However, other parameters could be oscillated—for example the pressure of the gas flow could be oscillated. The oscillating gas flow can comprise one or more oscillating components, all of different frequencies, amplitude and phase. The overall oscillating gas flow can be represented as a (summed) waveform, with a waveform shape comprising the various (summed) oscillating components. The nature of the varying gas flow is now described with reference to FIGS. 3A to 3D. The varying gas flow has one or more parameters, including but not limited to, a flow rate (flow rate parameter) and a pressure (pressure parameter). Each varying gas flow parameter (and the gas flow overall) comprises a base component, and one or more oscillating components which together combine (to create a summed waveform or signal). The varying gas flow overall as a result might also oscillate, and oscillation can refer to oscillation of gas flow components, or the overall gas flow. The varying gas flow/gas flow parameters can be represented as one or more waveforms (such as a flow rate waveform and a pressure waveform), with the various components making up the waveform shape, such as in FIG. 3E. The waveform itself may oscillate, and due to the combination of the components will have a waveform shape due to those components. It will be appreciated that the components could be represented or considered as sinusoidal Fourier components, although this is not essential. In this case, the base component would be a fundamental frequency, or DC/bias flow component.

Typically, the apparatus 10 is controlled to generate a varying gas flow with an oscillating gas flow rate, which results in an oscillating gas flow pressure. The remaining description for FIGS. 3A to 3E will be described in that context. However, this is not essential and it will be appreciated that instead the apparatus could be controlled to oscillate the gas flow pressure, or other gas flow parameter.

Figure 3A:
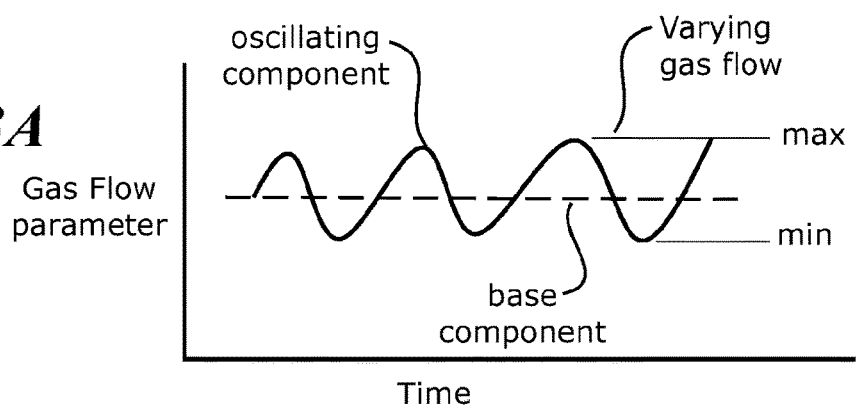
Figure 3B:
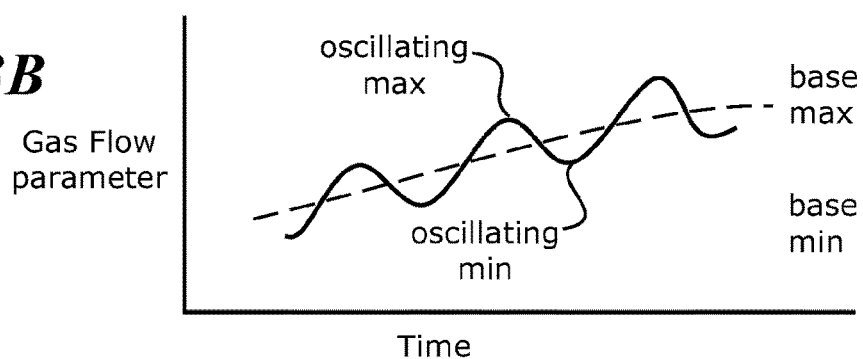
Figure 3C:
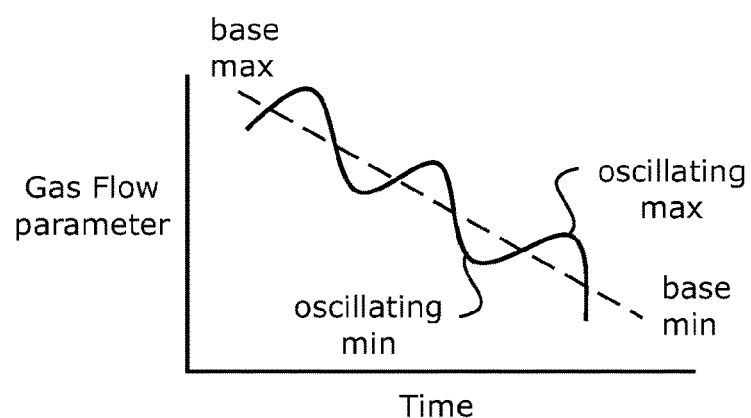
Figure 3D:
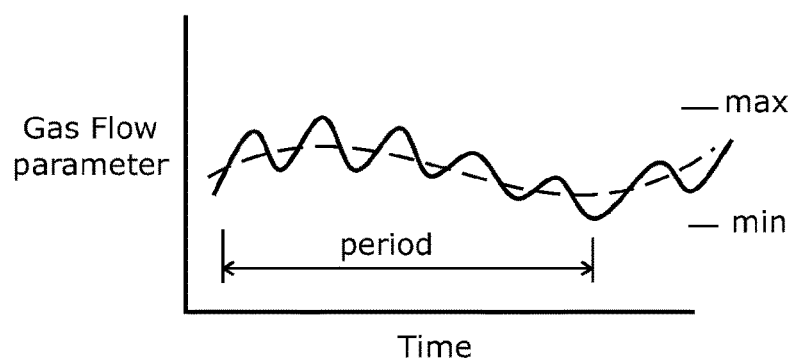

The base flow rate component of a varying gas flow is typically constant (see FIG. 3A), but it could also vary, such as (linear or otherwise) ramping up (See FIG. 3B) or down (see FIG. 3C), or varying in a (relatively slow) oscillatory manner (see FIG. 3D). Oscillation of the base flow rate, if at all, is generally at a very low frequency. Where the base flow rate varies, it can have a maximum and minimum magnitude (amplitude) that it varies between. Likewise, the base pressure component of a varying gas flow is typically constant (See FIG. 3A), but it could also vary, such as (linear or otherwise) ramping up (See FIG. 3B) or down (see FIG. 3C), or varying in a (relatively slow) oscillatory manner (See FIG. 3D). Oscillation of the base pressure, if at all, is generally at a very low frequency. Where the base pressure varies, it can have a maximum and minimum magnitude (amplitude) that it varies between. Other gas flow parameters could vary in a similar manner.

The base flow rate component of a varying gas flow can be summed with/modulated with (e.g. varied, modified, adjusted, or otherwise controlled etc.) or otherwise combined with the one or more (relatively high frequency) oscillatory flow rate components each with a frequency to produce varying gas flow (that may itself oscillate). One oscillatory component summed with the base component is shown in FIGS. 3A to 3D, but more oscillatory components are possible (such as shown in FIG. 3E and described soon). Each oscillatory flow rate component has a frequency that is relatively high compared to any slow oscillatory variation of the base flow rate. Each oscillatory component has a maximum and minimum magnitude (amplitude). Each oscillatory component also has a phase. Likewise, the base pressure component of a varying gas flow will be modulated with/summed with or otherwise combined with one or more (relatively high frequency) oscillatory pressure components to produce an oscillating varying gas flow. Each oscillatory pressure component has a frequency that is relatively high compared to any oscillatory variation of the base flow rate. Each oscillatory component has a maximum and minimum magnitude (amplitude). Each oscillatory component also has a phase.

FIG. 3E shows an example of a general case varying gas flow with a base flow component (e.g. flow rate or pressure) and plurality of oscillating gas flow components (e.g. flow rate or pressure), each of which combine together to provide a varying gas flow (with a waveform shape) with an overall period/oscillation.

Generally herein, reference to an oscillatory component or the like will refer to the high frequency component, not a base component, although it will be appreciated that all such components can be oscillatory. Hereinafter, references to oscillations will be references to oscillations of pressure and/or flow rate as context allows, but this should not be considered limiting and oscillation of other parameters might be possible. Reference to oscillation can also refer to an oscillation with more than one component and frequency.

As an example, and referring to FIGS. 3F, 3G, the controller 19 varies (by controlling the apparatus) the gas flow flow rate 13 from the flow source 12 around a base or bias flow rate 50 (bias in the sense of an offset from zero, equivalent to a DC bias analogy). This provides a (preferably high frequency 51) oscillating gas flow 52 around a (preferably although not necessarily constant) base flow rate 50 that assists with oxygenation and/or CO2 removal. As an alternative or additionally, the gas flow base pressure 53 is modified by an oscillating pressure 54 to provide an oscillating gas flow pressure 55. The pressure might be oscillated directly, or indirectly as a result of oscillating flow rate.

As an example, the frequency of the oscillating component could be 2 to 250 Hz, although the frequency could fall outside this range. More preferably the frequency is about 100 Hz or less, as this is avoids damping issues in the circuit. Where there are multiple oscillating components, each can be in the range above. Other frequencies are possible, as described elsewhere herein. For example, the frequency preferably could be about 0.1 Hz to about 3 Hz.

The frequency or frequencies can be chosen based on a physiological parameter. For example, in the case of basing the frequency on heart activity, frequencies will be around those of heart activity frequencies which are generally below 250 Hz. More preferably, the frequency(ies) is/are about 4 Hz or less and more preferably about 2 Hz or less for a child and about 1 Hz or less for an adult. More preferably, the frequency may be about 0.1 Hz to 3 Hz, or 0.3 Hz to 3 Hz. In either option, the oscillation/variation might not have a single frequency, but might comprise multiple (including a range of) frequencies (with associated phases and amplitudes)—see e.g. FIG. 3E. It will be appreciated that the disclosure herein could relate to any sort of flow rate/pressure or other parameter variation/oscillation with one or more frequencies. Reference in this specification to an oscillation frequency should not be considered limiting and should be considered to cover oscillation comprising two or more frequencies, and might also comprise phase/amplitude information.

The varying gas flow flow rate can have the following non-limiting examples of values. These are made with reference to FIGS. 3A to 3G Flow rate values for an overall combined/summed waveform will be described first—see, e.g. FIG. 3E. This is one or more oscillating components summed together with the base component. The overall (oscillating) waveform has a peak flow rate (amplitude), a trough flow rate (amplitude) and an instantaneous flow rate and a period. This gas flow waveform can have an instantaneous flow rate of about 375 litres/min to about 0 litres/min, or preferably of about 240 litres/min to about 7.5 litres/min, or more preferably of about 120 litres/min to about 15 litres/min. The overall waveform can have a peak (maximum) flow rate of about 375 litres/min to about 0.5 litres/min, or preferably of about 240 litres/min to about 30 litres/min, or more preferably of about 120 litres/min to about 60 litres/min. The overall waveform can have a trough (minimum) flow rate of about 240 litres/min to about 0 litres/min, or preferably of about 120 litres/min to 7 about. 5 litres/min, or more preferably of about 60 litres/min to about 15 litres/min. The frequency can be about 0.1 Hz to 3 HZ, or 0.3 Hz to about 3 Hz.

The base component (see FIGS. 3A to 3G), has an instantaneous, maximum and minimum flow rate (amplitude). The base component can have an instantaneous flow rate of about 375 litres/min to 0 litres/min, or 150 litres/min to about 0 litres/min, or preferably of about 120 litres/min to about 15 litres/min, or more preferably of about 90 litres/min to about 30 litres/min. If the base component varies (e.g. ramps), the component can have a maximum flow rate of about 150 litres/min to about 0 litres/min, or preferably of about 120 litres/min to about 15 litres/min, or more preferably of about 90 litres/min to about 30 litres/min. If the base component varies (e.g. ramps), the component can have a minimum flow rate of about 150 litres/min to about 0 litres/min, or preferably of about 120 litres/min to about 15 litres/min, or more preferably of about 90 litres/min to about 30 litres/min. In one example, the base component is 30 litres/min to 105 litres/min, but could be 50 litres/min to 120 litres/min for an adult with BMI>40. The maximum and minimum flow rates can still fall within the instantaneous flow rate range, and the instantaneous flow rate range can still fall within the overall waveform flow rate range.

Each oscillating component has an instantaneous, maximum and minimum flow rate (amplitude), frequency and/or phase. The amplitude of an oscillating component might be defined as a relative amplitude, for example with reference to the base component, or it might be defined as an absolute amplitude, or both. Each oscillating component can have an instantaneous flow rate of about 375 litres/min to 0 litres/ min, or 150 litres/min to about 0 litres/min, or preferably of about 240 litres/min to about 7.5 litres/min, or more preferably of about 120 litres/min to about 15 litres/min.

The oscillating component can have a maximum flow rate of about 375 litres/min to about 0.5 litres/min (or about 270 litres/min to about 0.25 litres/min relative to the base component), or preferably of about 270 litres/min to about 15 litres/min (or about 120 litres/min to about 0.5 litres/min relative to the base component), or more preferably of about 150 litres/min to about 30 litres/min (or about 60 litres/min to about 10 litres/min relative to the base component). The oscillating component can have a minimum flow rate of about 370 litres/min to about 0.5 litres/min (or about 270 litres/min to about 0.25 litres/min relative to the base component), or preferably of about 240 litres/min to about 15 litres/min (or about 120 litres/min to about 5 litres/min relative to the base component), or more preferably of about 150 litres/min to about 30 litres/min (or about 60 litres/min to about 10 litres/min relative to the base component).

The difference between the peak and the trough (peak to peak flow rate) can be a flow rate of about 240 litres/min to 0.5 litres/min, or preferably 120 litres/min to about 5 litres/min, or more preferably of about 60 litres/min to about 10 litres/min, or alternatively about 0 to about 100 litres/min, or about 40 litres/min to 70 litres/min. The maximum and minimum flow rates can still fall within the instantaneous flow rate range, and the instantaneous flow rate range can still fall within the overall waveform flow rate range. The frequency of an oscillating component can be about 0 to about 200 Hz, or preferably about 0.1 Hz to about 20 Hz, or more preferably about 0.5 Hz to about 3 Hz, and more preferably about 0.1 Hz to about 3 Hz. The phase can be about 0 to about 360 degrees or preferably about 0 to about 270 degrees, or more preferably about 0 to 180 degrees.

In more general terms, the instantaneous flow rate of gases at any point of operation supplied or provided to an interface or via a system, such as through a flow path, may comprise, but is not limited to, flows of 15 litres/min to 150 litres/min and up to 375 litres/min, and optionally at least about 40, 50, 60, 70, or 80 L/min, or more, and useful ranges may be selected between any of these values (for example, about 40 to about 80, about 50 to about 80, about 60 to about 80, about 70 to about 80 L/min, or any other subrange of 15 litres/min to 120 Litres/min, or even up to 150 litres/min or above).

For example, the base flow range would result in min/max flow of about 8 to about 100 L/min and about 30 to about 375 L/min for patients of 40 kg and 150 kg respectively. More preferably, the max/min flow rate is about 15 litres/min to 250 litres/min and more preferably 15 litres/min to 70 litres/min.

For premature/infants/paediatrics (with body mass in the range of about 1 to about 30 kg) the base flow can be set to 0.4-8 L/min/kg with a minimum of about 0.5 L/min and a maximum of about 25 L/min. For patients under 2 kg maximum flow is set to 8 L/min. The oscillating flow is set to 0.05-2 L/min/kg with a preferred range of 0.1-1 L/min/kg and another preferred range of 0.2-0.8 L/min/kg. The table below illustrates the maximum and minimum flow rates for a 40 kg and 150 kg patients respectively (those are somewhat outside the normal mass distribution where the mean for females/males in the US is about 75/85 kg respectively, 2004 survey). The flow rates noted are set so that in the normal ranges, a 150 kg patient can get 30 L/min pre-oxygenation and a very light patient (40 kg) can get ~50% over the typical 70 litres/min flow rate. In the case of oscillating flow rates, the minimum oscillating flow for a 150 Kg is 7.5 L/min and the maximum for a 40 kg patient is 20 L/min. Because pressure is related to flow squared, the pressure fluctuations are highly dependent on the absolute base flow rate plus oscillating flow rate or base flow rate minus the oscillating flow rate values.

| Flow Type | Min gas flow ranges (L/min/kg) | Max gas flow ranges (L/min/kg) | Max flow for 40 kg px | Min flow for 150 kg px |
|---|---|---|---|---|
| Base: example 1 | 0.2 | 2.5 | 100 | 30 |
| Base: example 2 | 0.25 | 1.75 | 70 | 37.5 |
| Base: example 3 | 0.3 | 1.25 | 50 | 45 |
| Fluctuating: example 1 | 0.05 | 0.5 | 20 | 7.5 |
| Fluctuating: example 2 | 0.12 | 0.4 | 16 | 18 |
| Fluctuating: example 3 | 0.12 | 0.35 | 14 | 18 |

Figure 2:
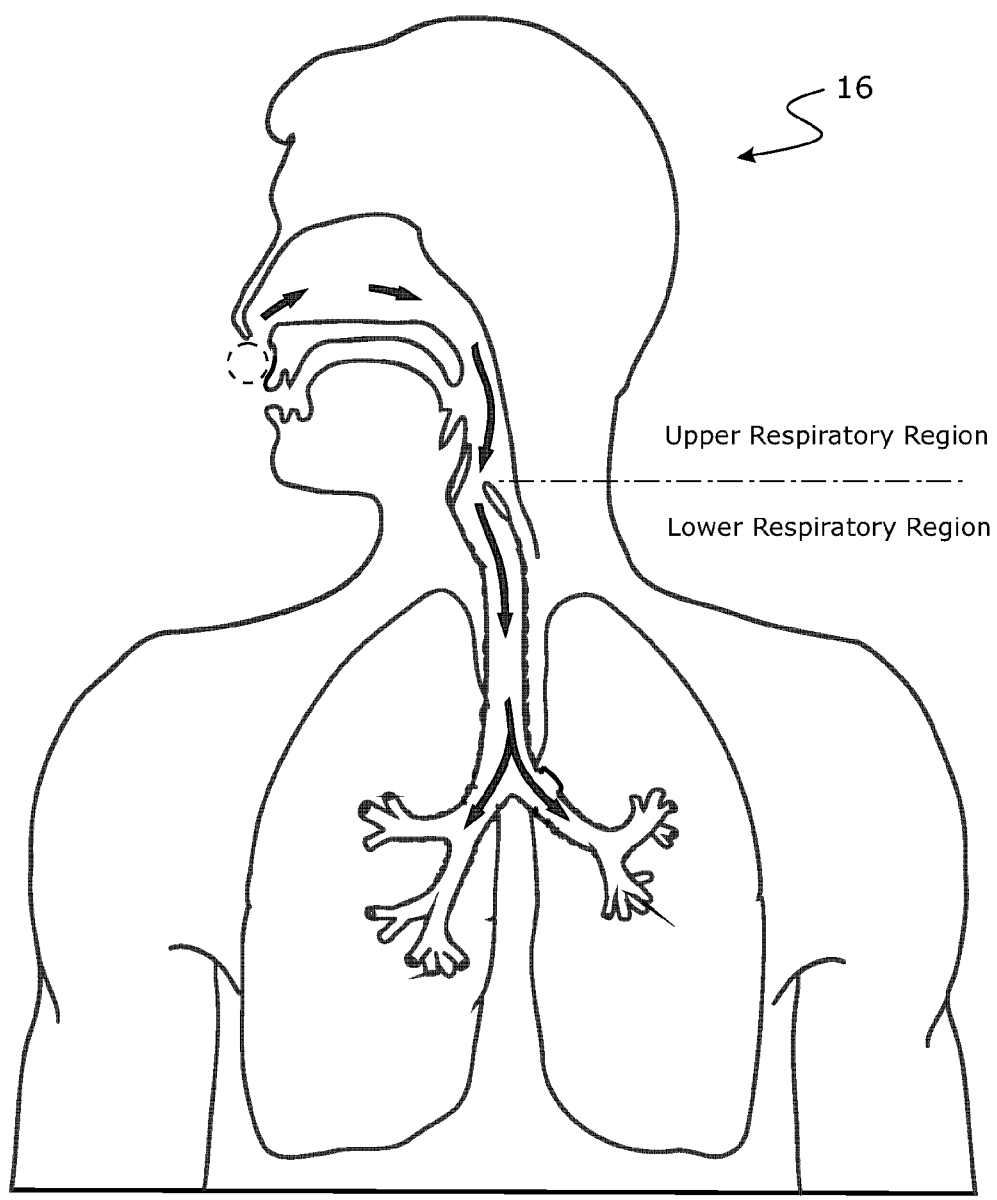
FIG. 2 illustrates airways of a patient.

Such relatively high flow rates of gases may assist in providing the supplied gases into a user's airway, or to different parts of a user's airway, for example such flow rates may allow for a delivery of such gases to the upper or lower airway regions, such as shown in FIG. 2. Upper airway region typically includes the nasal cavity, pharynx and larynx, while the lower airway region typically includes the trachea, primary bronchi and lungs.

Figure 8:
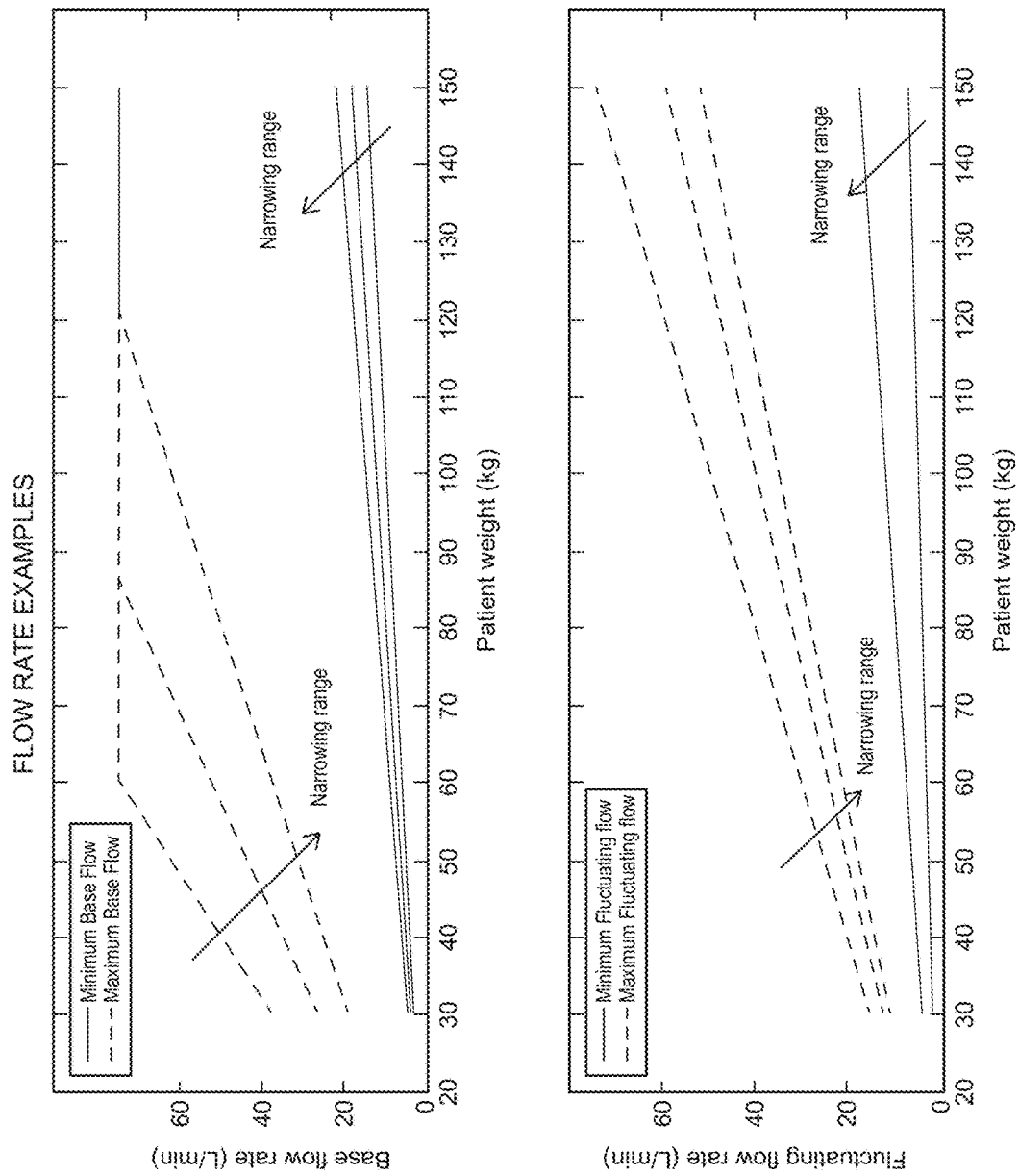
FIG. 8 illustrates possible flow rates delivered by apparatus and methods described.

By way of non-limiting example, gas flow rates provided by apparatus and methods described herein could be as also in FIG. 8. All flow rates herein can be read as about or approximate, and strict compliance with them is not necessarily required.

When considering the various flow rates described above, it will be appreciated preferably there is not a negative flow rate (that would correspond to flow going from the patient up towards the apparatus). It is desired for flow to travel out from the apparatus to the patient. The maximum amplitude of an oscillatory component allowed is therefore equal to the baseline flow rate. If the amplitude became larger than this, the trough flow would be less than zero (i.e. this would correspond to flow being sucked by the apparatus up from the patient). As such, the flow rates above will be considered in this context and a particular flow rate parameter of a particular component might be influenced by the flow rate parameter of another component.

With a symmetric oscillating component, the maximum peak flow is by definition equal to twice the baseline flow. However, under certain circumstances an asymmetric oscillation could be applied to the flow rate whereby the peak flow could go higher than this, but the trough flow always remain at zero or above.

In more general terms, the controller 19 can be configured to control the flow source, generic modulator 59 and/or any other aspect of the apparatus to provide a varying gas flow with: the desired base flow rate and/or pressure (frequency and amplitude) and the desired oscillation component or components (frequency and amplitude) to improve oxygenation and CO2 removal for the patient.

The controller can vary the base gas flow parameter(s) to create the oscillations using any suitable approach. For example, the controller might directly alter the pressure and/or flow rate by controlling the speed of the flow source. Alternatively, an external apparatus such as one or more gas flow modulators 59 might be used. The oscillations can be produced by any suitable mechanical and/or electrical configuration. Any suitable apparatus for oscillation can be used, such as valves (electrical, magnetic or pneumatic, for example), chopper wheels, transducers, pistons, or electronic modulation of the source, for example. FIG. 1 shows a generic modulator 59 operated by the controller for oscillating the gas flow, but this is by way of example and its position and nature should not be considered limiting.

The gas flow modulator(s) 59 (see FIG. 1) that creates the pressure oscillations may be positioned anywhere along the length of the system (from the patient end of the interface 15 to the flow source 12) and may achieve the oscillations 51/54 in a number of ways, such as some of the non-limiting methods and components listed below. The component 59 may be removable from the circuit and/or system.

- Electronic valve such as proportional or solenoid valve
- Rapid variations in blower speed, actioned by the controller.
- Inline speaker or solenoid actuated diaphragm.
- Inline linear actuator
- A rotational or linear flow chopper
- Any aerodynamic or mechanical flutter valve.
- Bursts of compressed gas (i.e. air or oxygen) from a compressed gas source with control valve
- Motor driving any arrangement of rotational to linear motion
- Vibrating reeds that create oscillations
- One way valve/flap that opens at certain pressures, optionally spring loaded
  - Electronically controlled proportional valve that has a rapid response rate. The proportional valve may be a solenoid controlled valve or any other suitable proportional valve having a suitably rapid response.

The addition of flow/pressure oscillations to gas flow as described can do the following.

- Reduce the time averaged flow rate/pressure necessary to achieve a certain level of oxygenation and $CO_2$ clearance. High flow rates can be perceived as less comfortable, so any ability to reduce the flow rate while maintaining the same oxygenation support is desirable.
- Increase the total oxygenation and $CO_2$ clearance capacity of high flow gas delivery
- Decrease the time required for pre-oxygenation The oscillation frequency (pressure or flow) of the gas flow could be anywhere from about 2 to about 200 Hz as previously described or otherwise as described elsewhere herein (more preferably, the frequency may be about 0.1 Hz to 3 Hz, or 0.3 Hz to 3 Hz) and have instantaneous pressure or flow amplitudes of up to 200 L/min and/or 50 cmH2O or otherwise as described elsewhere herein. The waveforms of the oscillations could be any suitable shape. Some examples of waveform shape are:

- Sinusoidal
- Square
- Triangular
- Saw tooth
- Gaussian
- Based on physiological waveforms (e.g. blood pressure or cardiogenic pulsations, cough, sneeze wave patterns etc.)

2.3 Determining Base and Oscillation Component Frequencies, Amplitudes and/or Phases for Varying Gas Flow In general terms the, the amplitude, frequency and/or phase of base and/or oscillation components (including the parameters thereof as stated above) are determined based on default parameters, user input, experimental data and/or physiological parameters. These can be set to optimise patient response. For example, the frequency and/or amplitude and/or phase of the base and/or oscillation components of a varying gas flow can be based on one or a combination of various considerations, such as (but not limited to) the following.

Sweeping the frequency and/or amplitude to find an optimum patient response.

The respiration rate and phase of the patient.

The resonant frequency of the lungs of the patient.

The resonant frequency of the chest cavity of the patient.

The heart rate (or more generally heart activity) of the patient.

The brain activity of the patient.

Random noise.

Clinician input, for example mean pulmonary artery pressure.

Experimental data or default/predetermined parameters or other parameters that assist $CO_2$ removal and/or oxygenation.

Measurement of $O_2$.

Measurement of $CO_2$.

A frequency that promotes mixing or turbulence.

A frequency that promote bulk gas flow movement

Based on the above, the gas flow components have set instantaneous amplitude, frequency, phase, maximum and minimum amplitudes.

For example, oscillation components (that is the various parameters of components, such as phase, frequency and amplitude) could correspond to (be based on) or be synchronised/matched with one or a number of different respiratory or other patient parameters, or other general parameters that assist $CO_2$ removal and/or oxygenation. "Correspond" more generally means to relate to or be influenced by, but not necessarily match (although it could comprise match also).

Also it has been determined that a lower frequency of oscillating flow rate component can promote bulk gas flow movement. This can assist $CO_2$ removal and/or oxygenation—alone or in combination with other oscillating frequency components. This frequency is preferably lower than other frequencies, such as the heart activity frequency and/or trachea flow of the patient frequency.

Also it has been determined that a higher frequency of oscillating flow rate component can promote mixing or turbulence. This can assist $CO_2$ removal and/or oxygenation—alone or in combination with other oscillating frequency components. This frequency is preferably higher than other frequencies, such as the heart activity frequency and/or trachea flow of the patient frequency.

It has been determined that as $CO_2$ is exhaled through the trachea, a plug of $CO_2$ travels through the trachea and oscillating gas flow assist in clearing this plug from the airways. The apparatus and methods described above assist to provide $CO_2$ removal and/or oxygenation by providing for oscillating gas flow. The efficiency of $CO_2$ removal and/or oxygenation can be improved, where the parameters of the oscillation components are based on a physiological parameter, as described above. Oscillations could be chosen to have frequencies and/or phases that are matched to a physiological parameter frequency/phase, or some harmonic or other multiple of that frequency/phase. As another example, the oscillation components could be chosen to have an amplitude (instantaneous, maximum and/or minimum) that is proportional or inversely proportional to the amplitude of the physiological parameter (such as heart activity).

Some of these are described in more detail below, and various other examples described demonstrate how a gas flow component (oscillator or base component) can be based on a physiological parameter (or other parameter).

2.3.1 Heart Activity

Heart activity moves gas flow up and down the trachea of a patient. The heart has electrical signals that have a fundamental frequency. The electrical signals trigger the heart to pump, at that frequency, which in turn pumps blood with oscillatory pulses at that frequency. This influences oscillatory contraction and expansion of the lungs at that frequency, which in turn can move influence the oscillatory movement of gas up and down the trachea at that frequency. Heart activity can refer to any of these processes and the frequency of heart activity can refer to that frequency. While the oscillation at each stage above has the same frequency, each stage could have a different phase, due to a delay between each stage. For example, there could be a phase delay between the oscillating electrical signal occurring and the oscillating gas movement up and down the trachea.

During the delivery of nasal high flow to a patient, transport to the lungs occurs naturally by Aventilatory Mass Flow. However, the clearance of CO2 from the lungs must occur against this net flow. Small oscillations of respiratory flow occurring at the same frequency as the heart activity have been observed during both inspiration and expiration. The inventors determined that cardiogenic pulsations combined with turbulence entrained from high pharyngeal flow cause longitudinal mixing of gas within the trachea. The mixing is sufficient to bring CO2 up from the lungs, while also enhancing the transport of oxygen down the trachea. On the expiratory part of each cardiogenic cycle, a portion of the mixed gas in the trachea is then ejected into the strongly flushed pharyngeal region. For example, if a gas flow with an oscillating pressure is delivered with an amplitude of pressure fluctuations of 2 cmH2O, then approximately 140-200 ml of gas would be pumped in and then back out of the lungs over each pressure cycle. The airway dead space is approximately 150 ml, and so in this example about 0 ml-40 ml of gas would be cleared from the lungs each cycle. In this simplified case, clearance would begin to occur when the volume of gas pumped reaches 150 ml per stroke, and this would correspond to a pressure variation of 2.14 cmH20 (for the case of low lung compliance in the example)—1.5 cmH2O (for the case of high lung compliance) in this example. It is noted that the airway and lungs can readily withstand pressures of up to 5 cmH2O relative to atmospheric pressure.

As such, the inventors have determined that providing a varying gas flow with at least one oscillating component of the right frequency, phase and/or amplitude based on the heart activity frequency can assist the CO2 clearance and/or oxygenation process. For example, if the oscillating component(s) has/have frequency(ies) the same as or near the cardiogenic pulsations (heart activity) creates this effect and facilitates CO2 removal and/or oxygenation. The varying gas flow provided can be varied in synchronism with the heart activity, such as by varying the gas flow to have oscillation components with frequency(ies) matching those of the heart activity. The effect of this is to move gas up and down the trachea and contributing to CO2 transport out of the lungs and oxygen transport in to them. This effect enhances the naturally occurring cardiogenically-induced oscillations of gas up and down the trachea. The net effect of the cardiac-synchronised flow variations to the flow is to greatly enhance the clearance of CO2 achieved by cardiogenesis on its own (typically by a factor of between 3 and 10). More generally, the oscillation frequencies do not need to be synchronised with heart activity, but rather correspond to it in some way.

Figure 9:
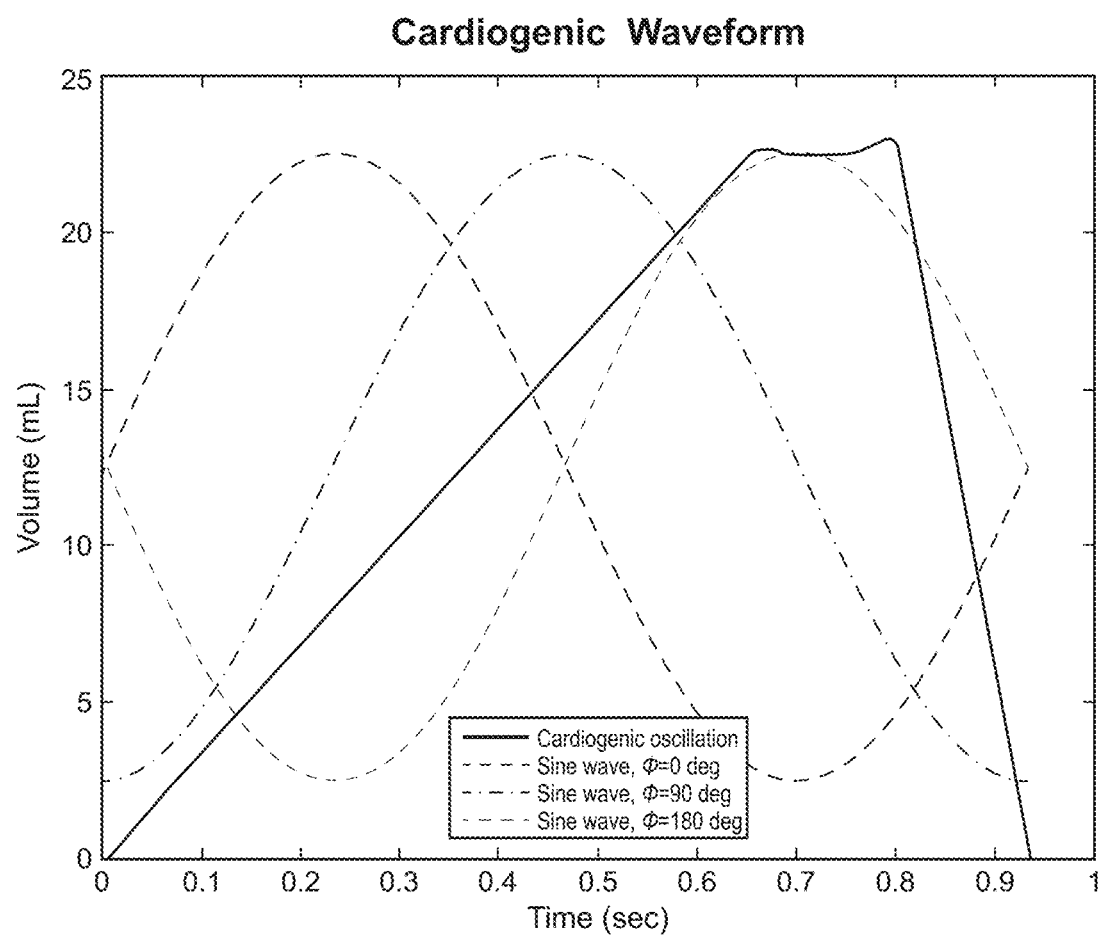
FIG. 9 shows a cardiogenic waveform for experimental example #1.
Figure 16:
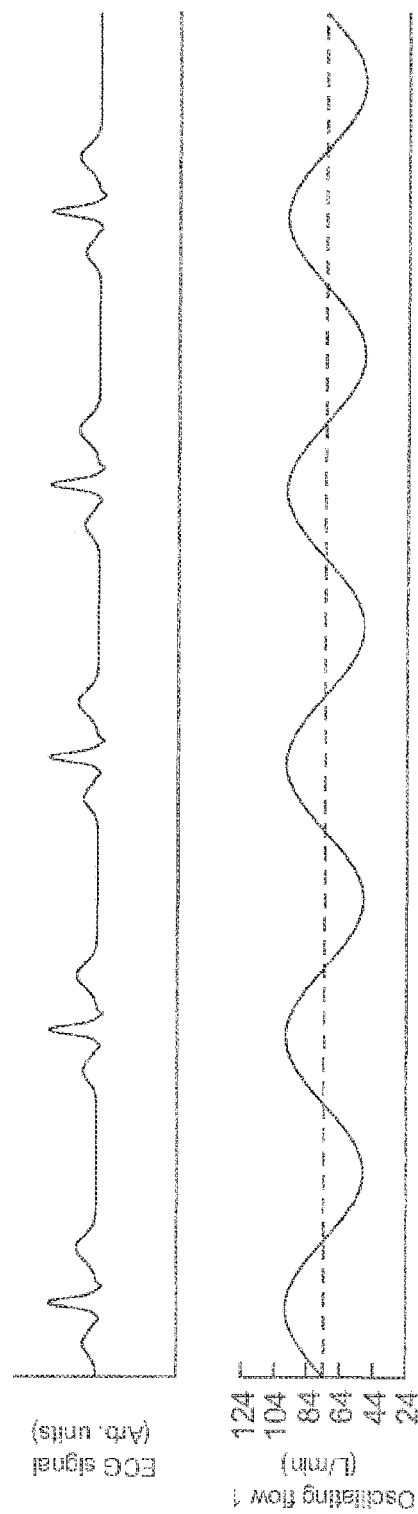
FIG. 16 shows an ECG signal, in relation to an oscillating gas flow.
Figure 17:
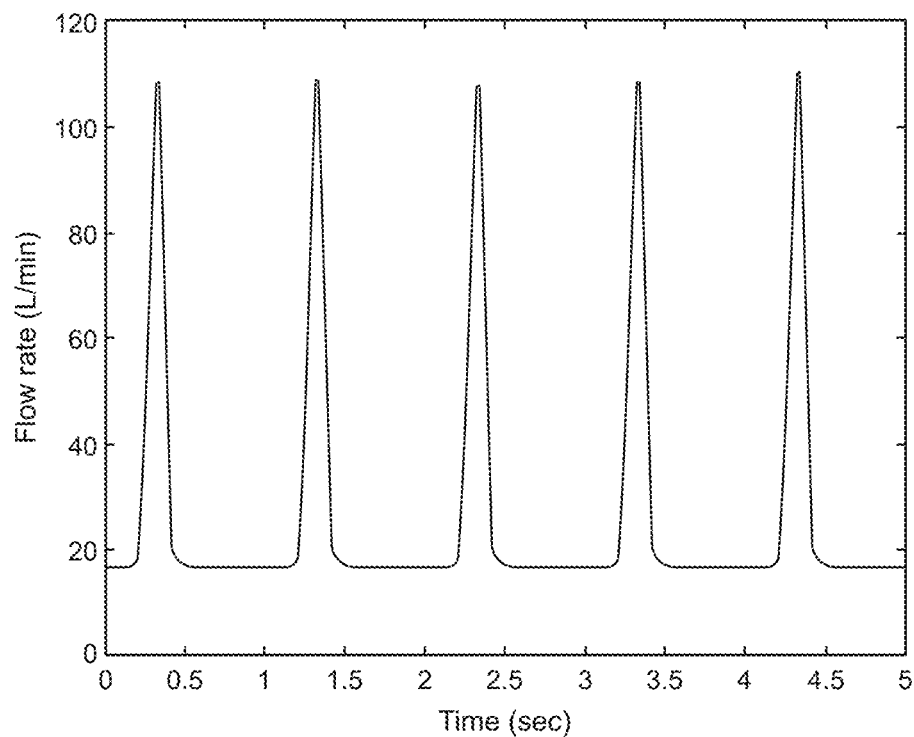
FIGS. 17 and 18 show alternative Gaussian oscillatory flow rate waveform and the related CO2 clearance.
Figure 18:
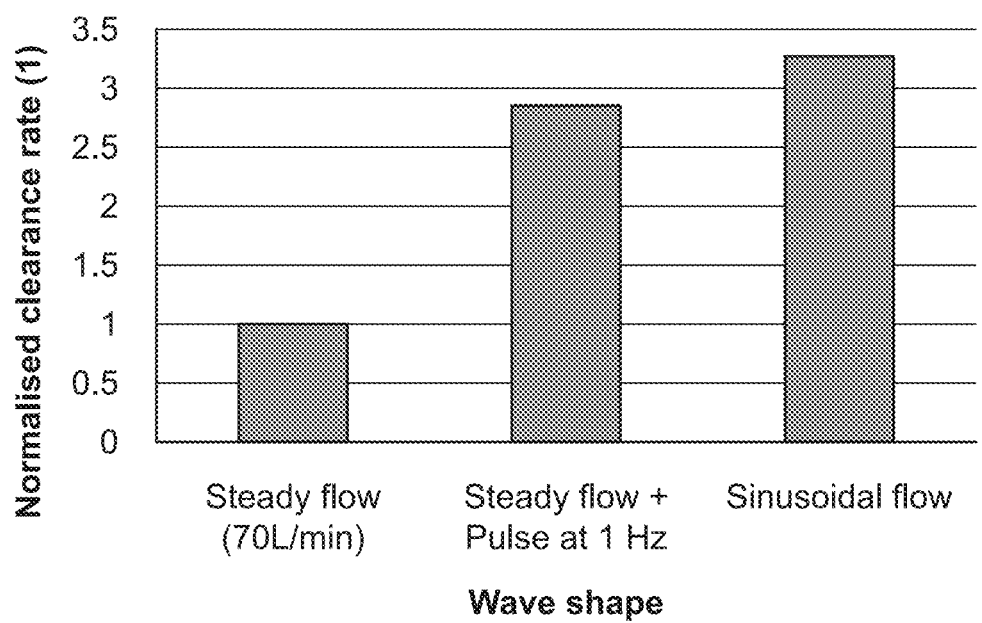

As one example of how a gas flow component can be based on a physiological parameter; heart activity can be sensed and the frequency of one or more oscillation components can be made to have a frequency the same as or similar to the heart activity. Additionally or alternatively, because there is a delay between the heartbeat and the gas flow in the trachea, each oscillation component might have a delay, such as a phase delay, relative to the heart activity waveform, to compensate for the gas flow delay. Preferably, the gas flow oscillation component is matched as closely as possible to the heart activity frequency (such as shown in FIG. 16 which shows an ECG signal showing heart activity and an oscillating component with the same or similar frequency), although some variance is possible, to provide optimum CO2 removal and/or oxygenation. The phase is preferably matched, although a phase difference still produces useful effects (such as shown in FIG. 9). Also, as mentioned earlier, a phase delay relative to one stage of heart activity, may help to align with the phase of another stage of the heart activity.

In one exemplary example, the controller 19 can monitor the patient's heart activity through a sensor (e.g. sensor 18*d*) and control the system 10 so that gas flow oscillations 52/55 are synchronised/matched or otherwise correspond with/are based on the patient's heart activity. The controller 19 can be configured to control the flow source 12 to provide a gas flow that oscillates 52/55 at the same frequency as that of the (or otherwise based on) patient's heart activity frequency to increase the mixing of the gases, promoting oxygenation and CO2 clearance. The oscillation could be in phase, in anti-phase (or constant relative phase) or out of phase with the heart rate but preferably in or close to in phase (or with a phase delay) as previously described. In a preferred example, the frequency of an oscillating component can be about 0.1 Hz to about 3 Hz, or preferably 0.5 Hz to about 3 Hz, and, which corresponds to the frequency of typical heart activity.

In one example, the patient's heart activity (including "heart beat" or "heart rate" or any of the heart activity stages as mentioned earlier) could be monitored using sensor 18*d* and the output signal could be used as the input into the controller to determine the frequency of gas flow oscillation 52/55. For example, the heart activity could be monitored using sensors e.g. 18*d* in one or more of a number of ways. Non limiting examples follow.

Using a heart rate monitor (heart activity sensor). Flow sensor to measure gas flow in the trachea.

Using the plesythmograph signal from a pulse oximeter probe.

Using an ECG signal picked up by electrodes (sensors) attached to the skin (usually the chest) and coupled to a very sensitive amplifier.

In each case, it is the output electrical signal which fluctuates in synchronism with the heart activity that is connected to the controller.

Alternatively or, the user could be prompted to enter the heart activity information into the I/O interface 20, from empirical data, previously recorded heart activity, or some other source. In this case, the controller 19 receives input relating to heart activity of the patient from the I/O—such as from a clinican who takes the patient's pulse. Alternatively or additionally, the heart activity information could be in a memory forming part of or separate to the controller. In this case, the controller 19 receives input relating to heart activity of the patient from the memory, which could be stored based on e.g. empirical data of typical heart activity frequencies and/or typical gas flow oscillation frequencies that prove effective. For example, resting heart rates are typically between 40-100 bpm (0.67-1.67 Hz) but could be in the range of 30-180 bpm (0.5-3 Hz) under extreme physiology (e.g. under medical procedures or intense exercise).

Alternatively, the gas flow system 10 could comprise an electrocardiogram or heart rate monitor or echocardiograph (which could be considered heart activity sensors in the system). In this case, the controller 19 receives input relating to heart activity of the patient from the sensors in the system.

Irrespective of how the heart activity is measured or otherwise determined, it can be used by the controller to determine a suitable frequency(ies) for the oscillation component(s) of the varying gas flow. For example, if the heart rate was measured at 80 beats per minute the high flow system could be set to oscillate 52 the flow between 70 L/min and 40 L/min 80 times a minute (1.333 Hz).

In more general terms, the varying gas flow oscillation component frequency and phase is based on the gas flow in the trachea. Heart activity frequency can be used to determine the frequency of gas flow in the trachea as described above, and therefore the gas flow oscillation component frequency and phase is based on the heart activity frequency. However, another measure could be used for trachea gas flow. For example a flow sensor could be placed to measure flow rate in the trachea, and the oscillation component frequency and phase based on the gas flow frequency is determined from the flow sensor.

Where a sensor is used, there can be continual or periodic feedback of the heart rate activity so the frequency and/or of the oscillating component can be adjusted when it drifts from the desired frequency or phase.

The human body is very adaptable and it is possible the heart would synchronise with oscillatory flow 52/55. Therefore, in an alternative, it is possible the user could enter an oscillatory frequency 51/54 they wished the gas flow to be at and encourage a change in the frequency of the heart. In this case, the user could choose to only have the set frequency or choose to provide some variation to the frequency (e.g. if the user set 80 beats per minute the high flow system could cycle between ±4 beats per minute around the set point). Variation is thought to be beneficial.

The controller 19 can controller the flow source 12 to produce gas flow oscillations in accordance with one of the following.

The oscillations 51/54 are synchronised so that as the heart expands, an increase in gas flow is delivered, flushing the $CO_2$ from the airway and displacing it with oxygen from the flow source. As gas moves up the trachea as a result of the cardiogenic oscillation the gas flow is reduced to facilitate it coming up. As the gas goes down the trachea as a result of the cardiogenic oscillation the gas flow is increased.

The oscillations 51/54 are synchronised so that as the heart expands, a decrease in gas flow is delivered (this could be positive, zero, or negative), causing a suction effect on the $CO_2$ drawing it out from the airway and allowing oxygen to replace it when the flow is increased again.

It will be appreciated that in addition to determining one or more oscillation/base components for a varying gas flow based on heart activity, one or more other oscillation/base components of that varying gas flow could be determined based on other physiological parameters (such as those described next). Any reference throughout the specification to a varying gas flow with one or more oscillation/base components based on heart activity does not preclude that varying gas flow having one or more other oscillation/base components based on some other parameter, such as a physiological parameter. Multiple oscillatory components, each with frequency, phases and/or amplitudes all determined based on multiple different physiological or other parameters could be determined and combined to form a varying gas flow for $CO_2$ removal and/or oxygenation. For example, this could be an oscillating gas flow has a plurality of oscillating gas flow components at a plurality of frequencies. All the examples described herein could be used alone or in combination.

2.3.2 Respiratory Rate

In one example, to assist with determining a suitable oscillation waveform for the gas flow, the controller can monitor the respiratory (breath) flow of the patient (using one or more of the sensors) to determine parameters and/or phases of the respiratory flow and the patient's requirements. For example, the controller 19 can utilise parameters of the respiratory flow wave (including the phase of breath and/or the transition between inspiration and expiration). Methods and apparatus for respiratory flow wave, meeting (e.g. peak) inspiratory demand and estimating (e.g. peak) inspiratory demand could be used. It should also be noted that the following can utilise switching modes of operation between inspiration and expiration. The exact moment of switching should not be limited to the exact transition point.

By determining the patient's respiratory flow the controller 19 could be configured to operate the flow source 12 and other aspects of the system 10 to do one or more of the following.

Superimpose oscillatory flow 51 (such as in FIG. 3F) on the respiratory flow.

Determine the phase of the breath (inspiratory, expiratory), and
only deliver oscillatory flow during a set phase (inspiratory or expiratory or near the end of expiration),
Stop flow during expiration to allow the lung to passively expire; the "stop" flow being for example 0 L/min or a low flow (e.g. below 20 L/min), and/or
provide oscillatory flow 52 (such as in FIG. 3F) and intermittently provide negative flow for the expiratory portion of a breath; the "negative" flow being for example 0 L/min or a negative flow that sucks flow from the patient.

Oscillatory flow could be delivered through the patient interface (e.g. nasal cannula or nasal mask) 15 as done in traditional high flow therapy. However, in present embodiments where oscillating gas flow 52/55 is provided during medical procedures (such as anaesthesia) there are other possible delivery configurations also, which comprise the following.

A device (e.g. mask and cannula combination interface 15) could be used to deliver oscillatory flow 52/55 through the nose and mouth. The delivered oscillations could be the same or different for the nose and mouth. They could also be delivered at different times (e.g. only through the nose, then only through the mouth)

A device (e.g. extended Endotrachaeal tube) could be used to deliver different oscillatory flows 52/55 into the left and right bronchi to maximise the potential to meet the resonant frequency of each side of the lungs.

2.3.3 Resonant Frequency Lungs

In another example, the controller can control the system so that gas flow oscillations are synchronised/matched or otherwise correspond with the patient's lung resonant frequency or frequencies. The patient's lungs are an example of a body cavity with a resonance. Delivering a frequency that matches the resonant frequency/ies of the lungs as a whole, or a spectrum of frequencies that encompasses the resonant frequency of the various airways of the lungs encourages mixing, oxygenation and CO2 clearance. The resonant frequency/ies will be different for each patient. The controller 19 is configured via the sensors (e.g. 18d) and/or other inputs to detect the resonant frequency of the lungs. These are body (lung) cavity resonance sensors. This could involve operating the flow source provide oscillating gas flow 52/55 with a sweep of different frequencies over a range of frequencies while a patient is breathing, and monitoring via the sensor(s) respiratory parameters to provide feedback on when oxygenation and/or CO2 clearance is greatest. Possible respiratory parameters can comprise any one or more of the following.

CO2 (expired, transcutaneous)
O2 (expired, transcutaneous, SpO2)
Respiratory rate (lower CO2 concentrations lead to reduced respiratory rates)

Continuous monitoring of the respiratory parameters by the controller 19 could be used to ensure the frequency is matched throughout the anaesthetic or other medical procedure period.

In another example, the controller 19 is configured to modulate the gas flow 13 with noise to produce gas flow oscillations 52/55 to vibrate the airways at different frequencies. Instead of using a patient specific frequency, such as a resonant frequency, a random signal of random frequencies (noise) could be used by the controller to produce a noisy oscillating gas flow to encompass the majority of the population's optimal resonant frequencies.

2.3.4 Resonant Frequency Chest

In another example, the controller 19 can control the system 10 so that gas flow oscillations 51/54 are synchronised/matched or otherwise correspond with the resonant frequency of the chest wall of the patient. The patient's chest is an example of a body cavity with a resonance. The frequency that causes bulk movement may cause resonance or movement of the chest cavity. In general this frequency causes bulk gas movement rather than specific resonance. Respiratory inductance plethysmography (RIP) is a method of evaluating pulmonary ventilation by measuring the movement of the chest and abdominal wall. The controller 11 can receive input from a chest band or other device/sensor 18d (body (chest) cavity resonance sensors) to measure the chest wall movement. The controller 19 then controls the flow source 12 to deliver an oscillating gas flow 52/55 at a frequency that causes the most movement in the chest and abdominal wall to encourage gas movement and mixing, promoting oxygenation and/or CO2 clearance. The controller 19 might sweep the flow source 12 oscillations through a range of frequencies to ascertain the (resonant) frequency that optimises chest and abdominal wall movement.

2.3.5 Diaphragm Contraction

In another embodiment, the controller 19 can control the system 10 so that gas flow oscillations 52/55 are synchronised/matched or otherwise correspond with the frequency of the diaphragm muscle contraction. This is an example of a body cavity with a resonance. The frequency that causes bulk movement may cause resonance or movement of the diaphragm that causes lungs to move. In general this frequency causes bulk gas movement rather than specific resonance. Electromyography (EMG) is a technique that evaluates and records the electrical activity of muscles. The controller can receive input from an EMG system, which is used by the controller 19 to determine the frequency of oscillation. The controller 19 then operates the flow source 12 to provide a gas flow that oscillates 52/55 at the same frequency as diaphragm muscle contraction to increase the mixing of the gases; promoting oxygenation and CO2 clearance.

2.3.6 Brain Activity

In another embodiment, the controller 19 can control the system 10 so that gas flow oscillations 52/55 are synchronised/matched or otherwise correspond with the frequency of brain electrical activity. The controller 19 can receive input from an EEG system or other sensor 18d, which is used by the controller 19 to determine the frequency of oscillation of neuron firing. The controller 19 then operates the flow source 12 to provide a gas flow that oscillates 52/55 at the same frequency as neuron firing which may increase the mixing of the gases, promoting oxygenation and CO2 clearance.

2.3.7 Other Frequency Determination

2.4 Examples of Using Varying Gas Flow for CO2 Removal and/or Oxygenation

Figure 4:
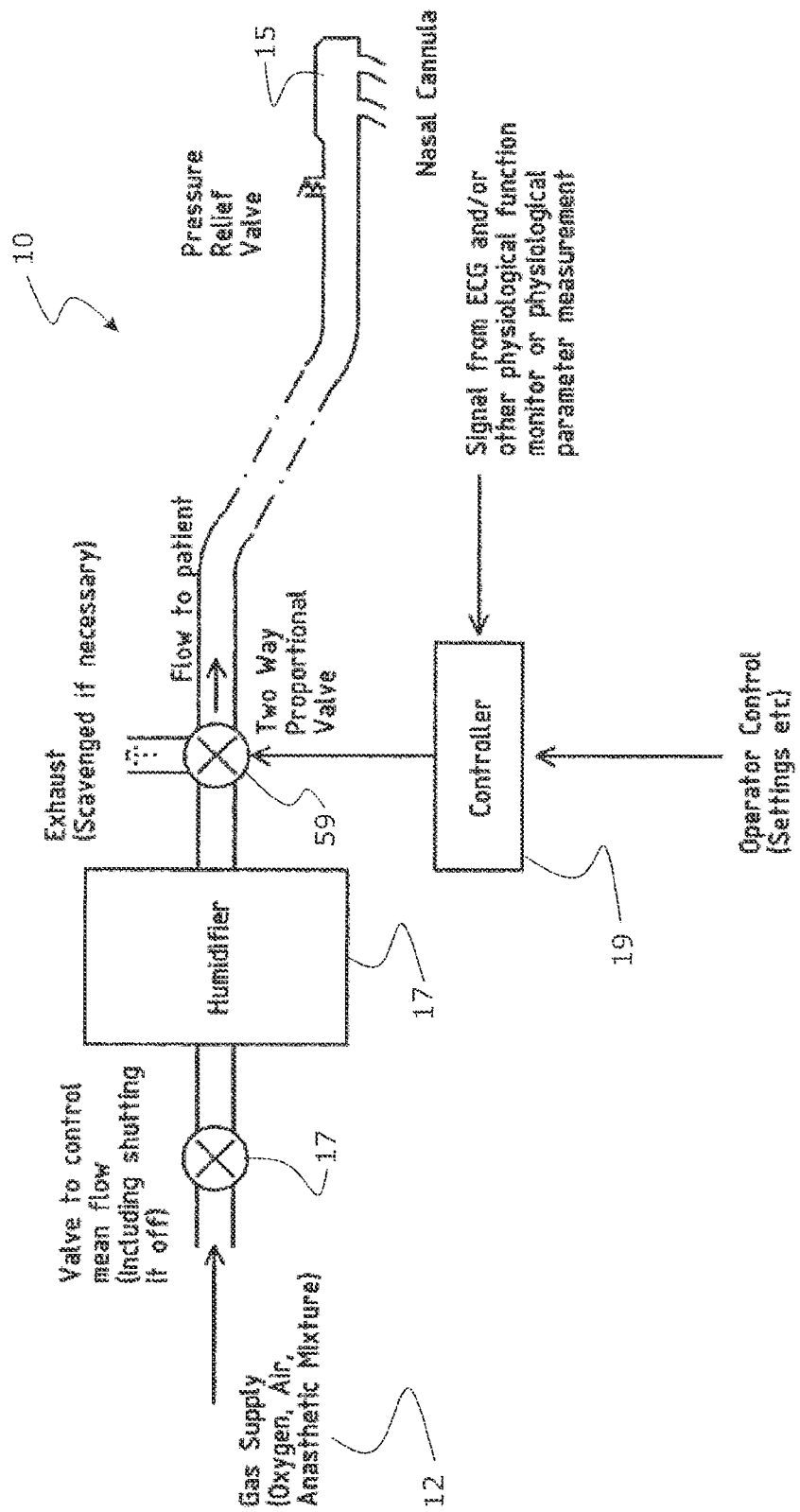
FIGS. 4 and 5 illustrate an apparatus/system for oxygenating a patient with high flow gas in relation to anaesthesia and the resulting parameter waveforms according to one example.

One exemplary and non-limiting example of an apparatus and method for supplying a high flow of humidified gas for oxygenation and/or CO2 removal, will be described with reference to FIG. 4 where the flow rate is cycled periodically to vary the pressure applied to the trachea and cause ventilation of the lungs. The apparatus is one example of the generic embodiment in FIG. 1. In this embodiment, the modulating device is a valve 60 after the humidifier.

In this setup dry gas, which may be air, oxygen, or any mixture of gases appropriate for the therapy to be applied to the patient is supplied from a flow source 12 to a humidifier 17 via a valve 59 which enables control of the mean flow rate. A pressure regulator can also be incorporated into the gas supply. Mean flow rate and oscillating flow rate could be provided on two separately controlled lines, in an alternative.

The humidifier 17 humidifies the gas to a level appropriate for the therapy to be used—normally this would be to just below saturation level at 37 degrees C., but may be any level appropriate for the patient. The humidified gas 13 passes through a two way proportional valve 60, which is controlled by a controller 19. The proportional valve may divert gas to the patient, or to an exhaust—or to any combination thereof. The purpose of using a two way valve is to assist that flow through the humidifier is as constant as possible (thereby providing optimum humidification), notwithstanding that flow to the patient may vary over a wide range under the control of the controller.

The controller 19 controls the valve 60 to vary the flow rate going to the patient cyclically to achieve a varying gas flow with the desired oscillation parameters as previously described, leading to the desired ventilation described above. The controller 19 is provided with input signals from measurements of patient physiological functions for example:—heart activity, spontaneous breathing etc. and physiological parameters for example:—levels of oxygenation, the partial pressure of $CO2$ in the blood etc. It is able to synchronise the flow fluctuations with periodic physiological functions so that the fluctuating flow can—for example—operate to enhance the effect of cardiogenesis for apnoeic patients or enhance spontaneous ventilation for breathing patients, where this is considered appropriate by the clinicians. Note, however, that in many applications— particularly for apnoeic patients—breath synchronisation will not be necessary.

Parameters such as upper and lower flow rates, the period of the flow rate cycle, and the waveform of flow versus time during the flow rate cycle may be set by the controller from inputs provided either by a human operator, or automatically from measurements of patient physiological functions and patient physiological parameters.

Figure 5:
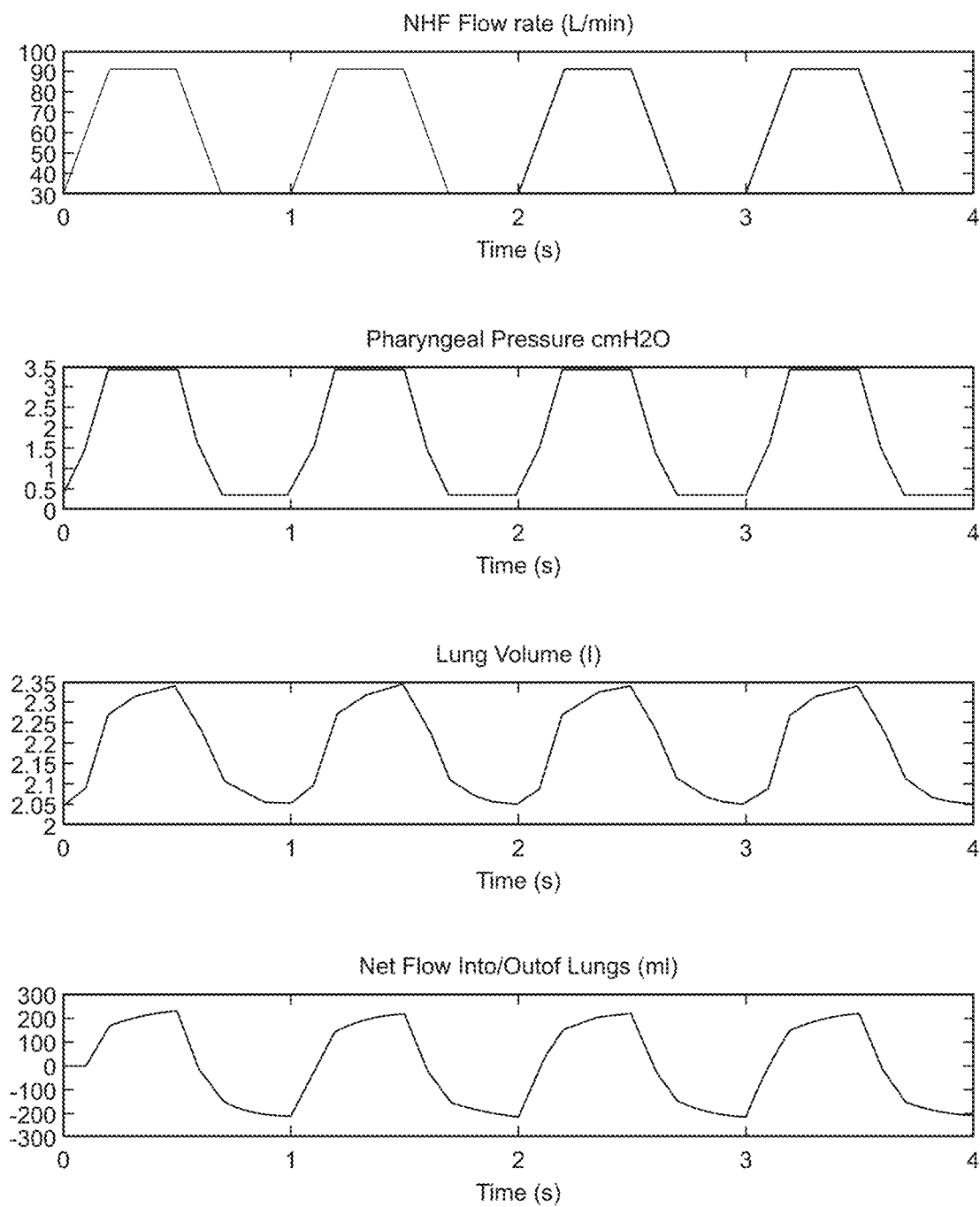

FIG. 5 shows the relationship between the delivered/applied flow rate, pharyngeal pressure, lung volume, and net flow of gas into and out of the lungs after dead space has been accounted for—for an apnoeic patient with open mouth and typical airway dimensions.

In this example, the period of the flow rate cycle was 1 second and flow rate cycles were started at t=0. If a normal patient were ventilated in this way, the minute volume achieved would be approximately 13 1—well above the minimum necessary.

Figure 6:
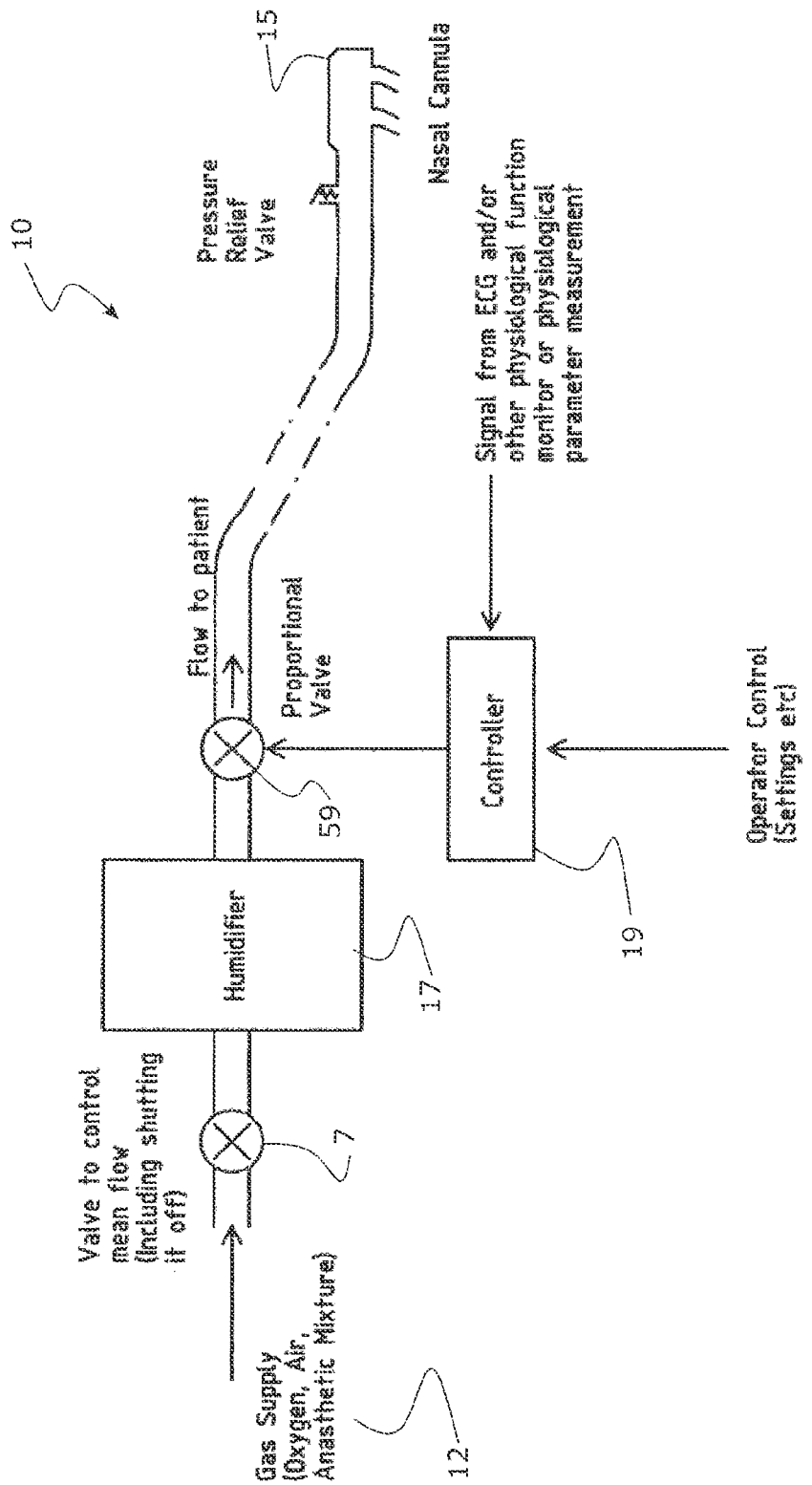
FIGS. 6 and 7 illustrate an apparatus/system for oxygenating a patient with high flow gas in relation to anaesthesia according to alternative examples.

FIG. 6 shows another example embodiment (this time a simplified arrangement) for use where the humidifier and circuit is able to respond to rapid fluctuations in flow. Here, the valve used to control the flow is a proportional valve which turns the overall flow in the system up and down.

Figure 7:
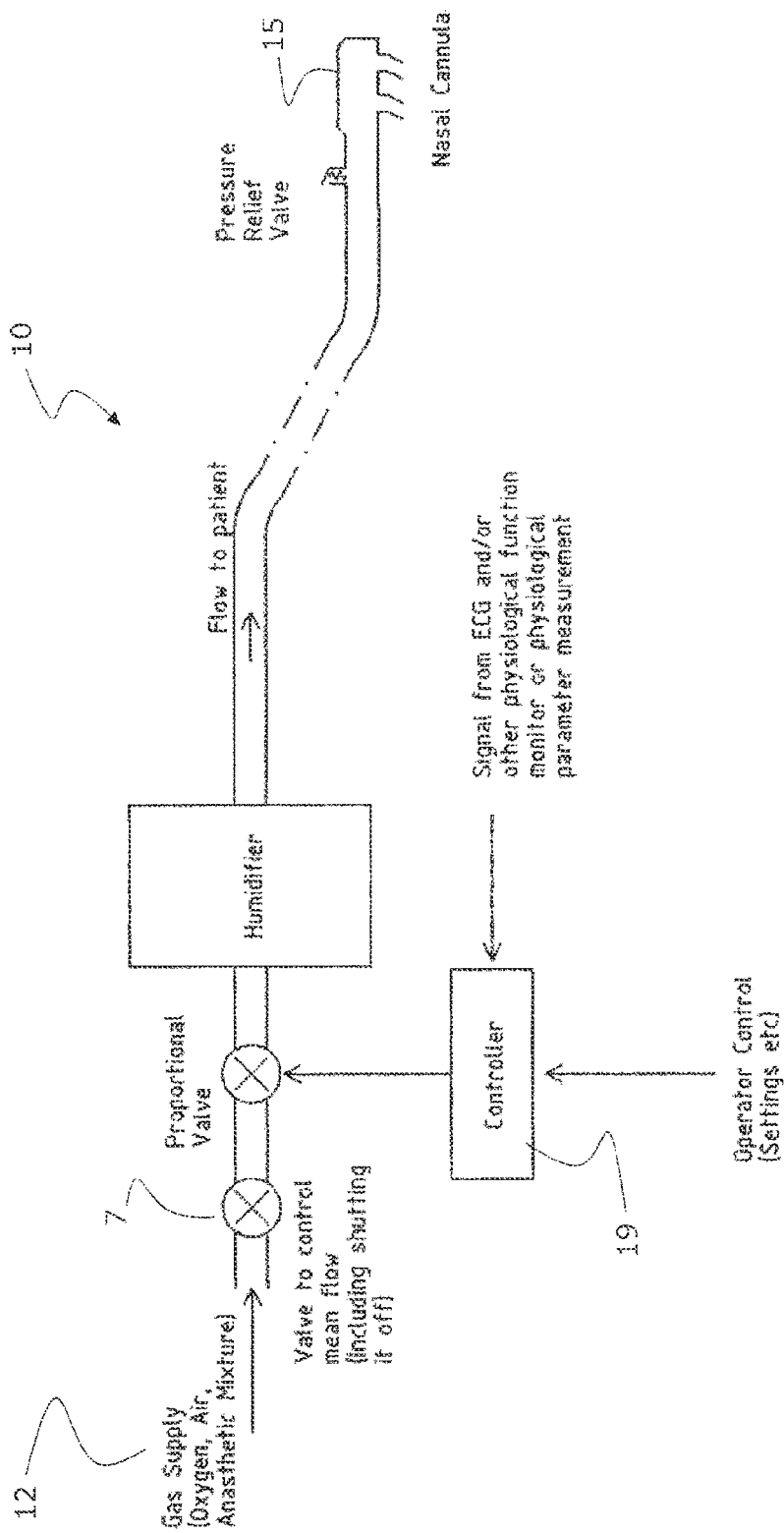

Finally, FIG. 7 shows another example embodiment where the flow control valve is placed in the gas supply to the humidifier. This has advantages because the proportional valve is able to work in dry gas—rather gas which is close to saturation point in humidity—and design of reliable mechanisms which provide rapid and precise control is easier if the gas is dry.

In these example embodiments, an optional pressure relief valve can be provided close to the cannula in order to prevent barotrauma to the patient in the event that the cannula seals into the nose and the mouth is closed. The pressure relief valve could be replaced by a pressure measurement system which is connected to the proportional valve controller, so that the controlled turns the flow off if the pressure at the patient rises above a certain level.

As noted early, and with reference for example to FIG. 1, apparatus according to embodiments described herein comprise a gas flow modulator 59. As described, the gas flow modulator 59 can be coupled anywhere in the system. Examples of positioning are as follows. A gas flow modulator could be placed in any one or more of the following positions. The gas flow modulator could be a standalone module or assembly connectable as per below, or an integrated module/unit, as appropriate.

At/after the oxygen supply 5 (e.g. from hospital wall supply, pressurised gas tank, or blower) and/or air supply 6. For example, the gas flow modulator 59 receives a gas supply via a gas supply tube fluidly connected to an inlet on the gas flow modulator. The gas supply may be a hospital wall supply, pressurised gas tank, blower, or a combination thereof. The gas may be oxygen or air, or a combination thereof.

At the input of the breathing apparatus 11 and/or at the input of the flow generator 3.

At the output of the flow generator 3.

Between the flow generator 3 and humidifier 17.

At the input to the humidifier 17.

At the outlet of the humidifier 17 and/or at the outlet of the breathing apparatus 11.

Anywhere else between the outlet of the breathing apparatus 11 and the patient 16 (such as in the conduit 14).

Within the breathing apparatus 11 housing or outside of it.

In more general terms, the gas flow modulator can be placed anywhere in the gas flow circuit where it can modulate or otherwise vary the gas flow.

Figure 21:
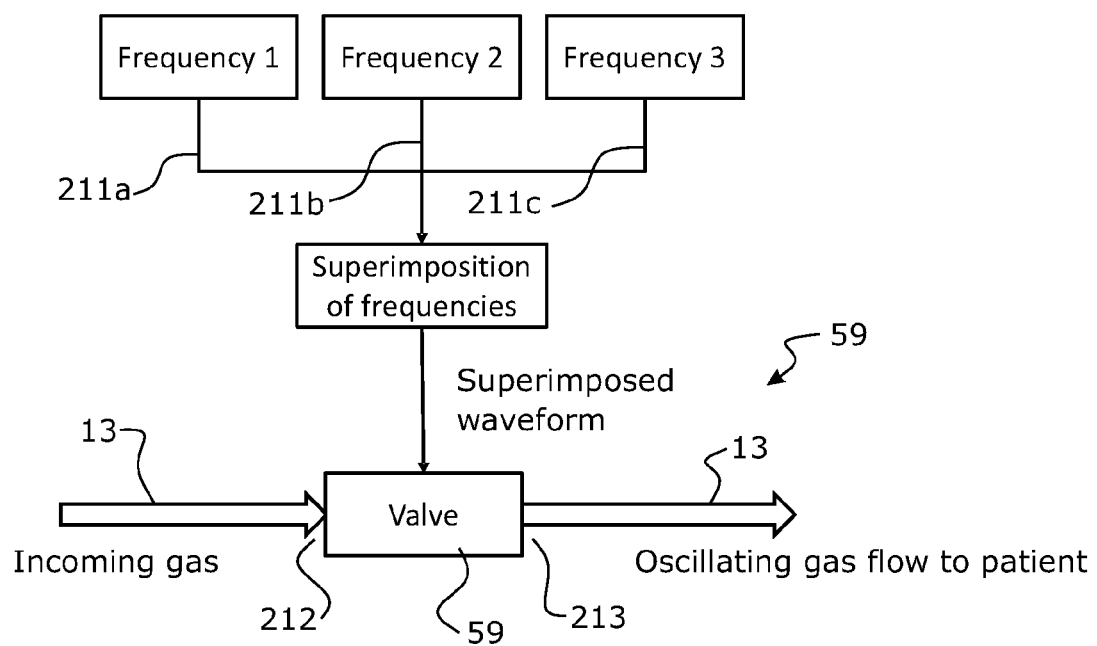
FIG. 21 shows in general form one example of a gas flow modulator.

One exemplary and non-limiting example of a gas flow modulator is described with reference to FIGS. 21 to 25. In this embodiment, the gas flow modulator can also be termed an "oscillator unit", or a "gas control valve". FIG. 21 shows in generic diagrammatic form a gas flow modulator 59. It takes the form of a gas controllable valve, such as a proportional valve or similar, or other device (such as any described previously) that can modulate or otherwise control and vary a gas flow. It has an inlet 212 for receiving an incoming gas flow 13, a control signal input 210, various functional components that are controllable by the control signal input to vary (e.g. oscillate) the gas flow coming into the inlet, and an outlet 213 for the varied output gas flow 13. The control signal input could be one or more inputs and could be user controlled, machine programmed or physiological. The alteration of flow could be a change in flow rate, or a change from a constant flow rate to a varying (oscillating) flow rate. In the FIGS. 21-28, the gas flow modulator is positioned between the gases source and the humidifier. This allows modulator to affect the gases flow as there is minimal interference for the gases. However, as noted previously, the gas modulator could be in any suitable location. The components of a proportional valve (or other device) and their operation of known to those skilled in the art. The gas flow modulator can be integrated in or alternatively removably coupled to the breathing apparatus system, in a position as previously described.

In this case, the gas modulator takes the form of a proportional valve, which receives a control signal 210. The control signal comprises one or more (preferably but optionally a plurality) oscillating components 211a-211c to represent/define a waveform comprising a plurality of summed/superimposed oscillating components as previously described. For example, the control signal/waveform has one, or optionally a plurality of at least two and optionally three or more summed oscillating components, each at a different frequency selected/determined as previously described. The control input signal 210 operates the proportional valve to provide an output oscillating gas flow 13 with a waveform comprising a plurality of summed oscillating components at those frequencies.

The operation of proportional valves are known to those skilled in the art, but they will be briefly described here. In general terms, a proportional valve works by receiving an electrical signal that energises or de-energises a solenoid coil. This causes movement in the valve creating variation in orifice size. This in turn controls the flow. The signals from the controller either rapidly supply or switch off power to the solenoid or alternatively vary the polarity of the voltage signal to cause a valve member to move rapidly.

The (e.g. three) frequencies of the oscillating components 211a-211c can come from any suitable source and can be any of the frequencies previously described.

For example, the user/operator of the gas flow modulator 59 may select the frequency or combinations thereof via a user interface. Each frequency may be:
- a fixed frequency selected and/or manually adjusted by the user/operator; and/or
- a frequency based on patient physiological signs (such as heart rate) communicated to the oscillator unit Alternatively or additionally the gas flow modulator 59 may receive frequency or combinations thereof via a one or more sensors and/or from a controller and/or memory.

Alternatively or additionally, the gas flow modulator 59 may be in electronic communication with an anaesthesia machine, EEG, ECG, pulse oximeter, or the like in order to feedback signals on the patient's physiological signs. For example, the gas flow modulator 59 might receive signals from the aforementioned units corresponding to the patient's heart activity, such as heart rate. The gas flow modulator and/or controller may process the incoming signal(s) and provide a corresponding oscillating frequency.

In one form, the gas flow modulator 59 can take the form of a proportional valve as shown in FIG. 21, placed anywhere in the circuit as previously disclosed, and controlled either with an on-board or external controller. In a further embodiment, the gas flow modulator 59 can be more sophisticated, and include further components to provide an integrated device, which can be placed anywhere in the circuit as previously described.

Figure 22:
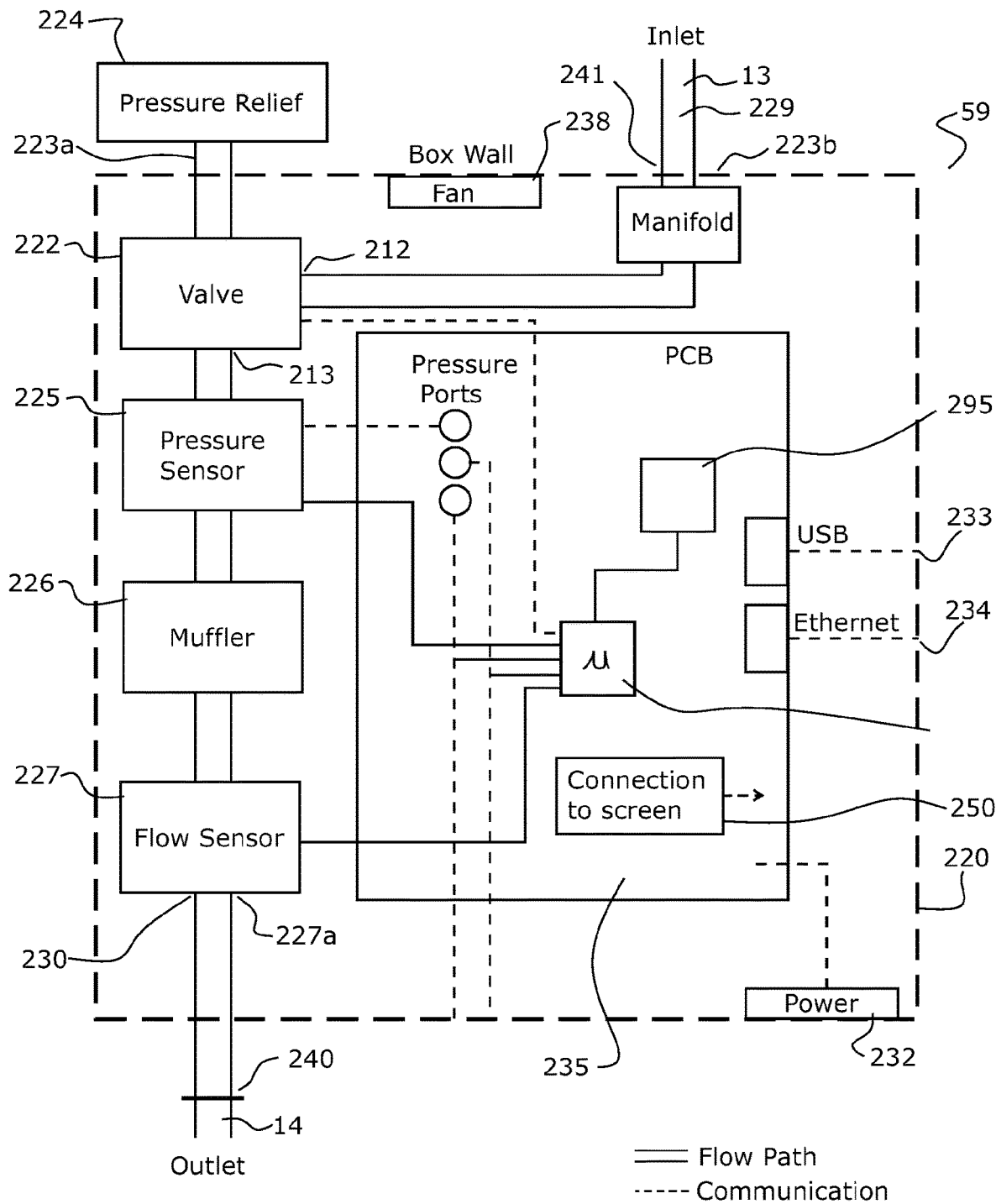
FIG. 22 shows one embodiment of a gas flow modulator.

FIG. 22 shows one such example of a further embodiment of a gas flow modulator 59, which integrates a number of components into a device/package/module.

The gas flow modulator (also termed "oscillator unit") comprises a housing 220 of any suitable shape, such as rectangular. The housing could be formed of polycarbonate, for example. However, it should be appreciated that the housing may alternatively be formed of other plastics.

The housing is preferably provided with the following ports:
- Gases inlet(s) 223b for receiving a gases supply tube 229 and a gas flow/supply 13 therefrom.
- Gases outlet(s) 230 for receiving and providing gases 13 to a gases delivery tube 14.
- A pressure relief valve attachment port 224a.

The housing may further comprise any one of the following ports.
- A carbon dioxide sampling port 231 for receiving a carbon dioxide sampling tube.
- Pressure sensor module ports 225a for receiving tubes in fluid communication with the patient interface 15, such that the pressure sensor 225 provides an indication of pressure at the patient interface 16.
- Inputs for other external sensors.

The housing may further comprise any one of the following electric/electronic ports.
- Power supply port 232.
- Removable data storage port (such as for a USB, SD card, or the like) 233.
- An Ethernet port 234.

In the housing there is a main PCB/electronics board 235 supporting and interconnecting the various components of the gas flow modulator 59. The gas flow modulator has a valve 222, such as a Proportional valve or other gas flow varying valve described herein. The valve has an inlet 212 with a conduit for a gas flow 13 to the outlet 223a of a manifold 223, the manifold also having an inlet for receiving an inlet gas flow 13, via the inlet 223b in the housing 220 of the gas flow modulator 59. The inlet 223b can be connected to any suitable source of gas flow that requires modulating, as previously described.

The Proportional valve 222 can have a pressure relief outlet and valve of 224. The pressure relief valve 224 is provided at the start of the flow path. The pressure relief valve is provided for patient safety and can relieve pressure should the system pressure exceed a predetermined pressure. Alternatively and/or additionally, a pressure regulator may be provided to reduce the pressure of the incoming gas supply and/or maintain a substantially constant system pressure.

The valve has a control input 221 coupled to a processor 265 on the PCB 235, which itself receives the control signal 210. The valve modulates, oscillates or otherwise varies the incoming gas flow on the inlet 212 to generate a varying (oscillating) outlet gas flow that is provided to the outlet 213. The control signal input 221 is generated by the processor 265, and like the control signal input 210, can comprise one or more (preferably but optionally a plurality) oscillating components 211a-211c to represent/define a waveform comprising a plurality of summed/superimposed oscillating components as previously described. For example, the control signal/waveform has one, or optionally a plurality of at least two and optionally three or more summed oscillating components, each at a different frequency selected/determined as previously described. The control input signal 221 operates the proportional valve to provide an output oscillating gas flow 13 with a waveform comprising a plurality of summed oscillating components at those frequencies. The control input signal 221 to the valve 222 could be the same as the control signal 210 provided to the processor 265. But, more likely it might be slightly modified, based on other inputs received by the processor form sensors and the like, as described further below.

The outlet 213 of the Proportional valve 222 is coupled to a pressure sensor 225 that can sense the pressure of the varying output gas flow from the Proportional valve and also receive input from the external pressure ports 225a in the housing that can receive pressure readings from external sources/senses—such as from the patient. For example, the pressure sensor module 225 is in fluid communication with the nasal cannula patient interface via two tubes extending from the external pressure ports 225a in the housing. Each respective tube is in fluid communication with a respective side of the nasal cannula 16—such that the pressure in each tube is indicative of the pressure in a respective side of the nasal cannula. The sensed pressure can be used by the processor 265 to determine if either or both sides of the patient interface are blocked, crushed, or obstructed.

The oscillating flow of gases out the outlet of the valve 213 passes through the pressure sensor 225. The processor 265 may utilise a signal generated by the pressure sensor 225 to determine a pressure in the system.

The outlet of the pressure sensor 225 is passed to an optional muffler 226 to attenuate noise. Alternatively, the muffler can be placed elsewhere, such as after the proportional valve 212. The muffler is optionally provided to dampen noise generated by the oscillating flow. As noted herein an external filter may be provided downstream of the gas modulator adjacent to the patient interface 16. An external filter e.g. 240 can also have the effect of dampening noise generated by the oscillating flow. As such, in an alternative embodiment, the muffler may be excluded and the external filter relied on to dampen noise generated by the oscillating flow.

The outlet of the muffler 226 is passed to a flow sensor 227, so that the oscillating flow of gases passes through the flow sensor. The flow sensor can sense the flow of the outlet gas flow from the Proportional valve 222 and produce a flow rate signal and can also receive input from external sensors. The processor may utilise a signal generated by the flow sensor 227 to compare the outgoing oscillating flow (e.g. flow rate) of gases with the oscillating waveform control signal 221 provided to the oscillating proportional valve and/or control signal 210 provide to the processor and make any corrections to the control signal 221 compensate for differences therebetween. The flow sensor has an outlet 227, which is coupled to the outlet in the housing of the modulator 59.

It should be appreciated that the pressure sensor 225 and flow sensor 227 may be positioned interchangeably.

The outlet 230 in the housing 220 provides the modulated gas flow through to other parts of the system and to the patient, as shown in FIG. 1. The inlet 223b in the housing 220 of the gas flow modulator 59, and the outlet 230 in the housing 220 can be coupled to the appropriate points in the breathing apparatus circuit, such as explained previously in relation to FIG. 1. This provides a self-contained module that can be used as required with the breathing apparatus 11 and used and replaced interchangeably, as required. The gas flow modulator 59 can be made and sold separately from the breathing apparatus 11 itself. The gas flow modulator can also have USB, Ethernet and other data and/or power communications ports, along with on-board power and/or power supply ports, as previously described. It can have memory, including permanent and or removable memory, for example memory connected to a USB or other port.

The gas flow modulator 59 can have an integrated input/output (user) interface 239 and/or have an output for connection 250 to an input/output for device such as a screen. In one embodiment, such as shown in FIGS. 23 and 25 to 28, an integrated user interface is provided 239. The user interface is provided on the exterior of the housing. The user interface may comprise a touchscreen. However, it should be appreciated that alternative embodiments of the user interface are possible. For example, the user interface can comprise a non-touchscreen display and pushbuttons, keypad, touchpad, or the like. The touchscreen can optionally occupy substantially all of the area of the front face of the oscillator unit. Alternatively, the user interface of the gas flow modulator can be remote from the housing 220. For example, the user interface may be embodied in a mobile app or a software interface on a nearby computer.

The user interface 239 can comprise controls for:
Turning gas flow "off".
Providing a gas flow with superimposed oscillations.
Providing a gas flow without superimposed oscillations.

The user interface 239 can further comprise controls for selecting a frequency, frequencies, or source of a signal for producing a frequency (such as based on heart rate) for the control signal 210 or 221. Furthermore, the user interface can comprise controls for selecting an amplitude of the aforementioned frequencies—where amplitude relates to the magnitude of pressure delivered with each oscillation.

The user interface may display a graphical representation of the patient's physiological signs. For example, this may include:
heart rate,
blood oxygen saturation, and/or
carbon dioxide content in breath Signals indicative of the patient's physiological signs may be received from anaesthesia machine, heart rate monitor, pulse oximeter, or the like in electronic communication with the gas flow modulator. The user interface may include alarms or indicators based on signals indicative of the patient's physiological signs (such as is received from an anaesthesia unit in electronic communication). For example, such alarms can comprise one or more of:
excess/low blood oxygenation saturation, and/or
excess carbon dioxide,
lack of airway patency, for example measured from a CO2 trace.

The PCB main board 235 and the housing 220 has inputs/outputs/ports (communication interface) for coupling to communications channels to a controller for operating the modulator. For example, it can be coupled to the controller 19 of the breathing apparatus 11 it will be used with. Alternatively the controller (processor) 265 can be provided in the housing, for example on the PCB main board 235. Preferably the controller is disposed on the PCB. The microcontroller is positioned in the housing of the oscillator. The PCB may comprise at least the processor and a memory unit, integrated with or separate to the processor. The PCB can comprise other hardware modules e.g. USB module, Ethernet module, Pressure modules or the like to process pressure signals from pressure sensors, a flow module to process flow signals from flow sensors, a biological signals module that is configured to process ECG or pulse oximeter signals. The biological signals module can also determine breath rate or other biological or respiration signals. Alternatively these modules can be software modules that can be stored as executable instructions in memory. Alternatively the controller could be integrated with a flow generator controller. The controller/processor 265 (whether on board or remote) receives signals indicative of the patient's physiological signs from external devices in electronic communication with the gas flow modulator 59 (such as an ECG, anaesthesia machine, pulse oximeter etc.). The controller receives signals indicative of the patient's physiological signs from sensors (such as those previously described) or other devices internally located within the gas flow modulator 59 (possibly comprising a carbon dioxide capnography 295, for example, that could be inside the gas flow modulator). Alternatively the capnography module may be remote of the gas modulator and may be electronically connected to the gas flow modulator/controller. The processor can also do one or more of the following:
Convey signals representative of the patient's physiological signs to the user interface 239 for graphical display.
Receive control instructions from the user interface, which may include a touch screen to receive input.
Determine a combined/superimposed waveform/control signal 221 from:
a waveform or waveforms selected by the user via the user interface,
a control signal 210 received, and/or;
waveforms indicative of the patient's physiological signs (such as heart rate) received from external devices in electronic communication with the gas flow modulator 59.
Drive the oscillating proportional valve in accordance with the combined/superimposed waveform based on the control signal 210 and other inputs.
Receive a signal from the pressure sensor 225 located within the gas flow modulator flow path.
Compare the signal generated by the flow sensor 227 located within the oscillator unit with the combined/ superimposed oscillating waveform 221 provided to the oscillating proportional valve, or with the received control signal 210.

Provide corrections to the combined/superimposed oscillating waveform/control signal 221 or 210 in order to compensate for any differences between combined/superimposed oscillating waveform/control signal 221 provided to the oscillating proportional valve 212, the received control signal 210 and/or the signal generated by the flow sensor 227.

Receive a signal from the pressure sensor 225 module indicative of pressure at the patient interface 16.

Determine whether the patient interface 16 is blocked, crushed, or obstructed based on the signal from the pressure sensor module 225 indicative of pressure at the patient interface.

Read/write data relating to the following to/from a removable data storage device 233 (such as a USB or SD card, for example).
 Gas flow modulator performance data.
 Gas flow modulator software maintenance/upgrade.
 Data indicative of the patient's physiological signs.

Send/receive data via an associated Ethernet port 234 relating to the following.
 Gas flow modulator performance data.
 Gas flow modulator software maintenance/upgrade.
 Data indicative of the patient's physiological signs.

Use inputs received at the gas flow modulator from distal pressure and/or flow sensor(s). For example, pressure sensors may be positioned downstream of the humidifier or at the interface or anywhere else external to the gas flow modulator and downstream of the gas flow modulator. There could be lines coming into the gas flow modulator. The modulator could use these signals to modulate or control the gas flow received by the user, by operating the valve 222 using the control signal input 221. The sensors could alternatively be in the breathing circuit.

The processor may comprise a single PCB or multiple PCBs and/or be disposed on one or more PCBs. Multiple PCBs may be dedicated to different respective functions.

The gas flow modulator can optionally comprise a carbon dioxide capnograph module 295: The module will be in fluid communication with a port located on the exterior of the housing 220. In use, a small-diameter breath sampling tube extends from the port and terminates in vicinity of the patient's mouth or nostrils. The gas flow modulator 59 draws a small flow of gas through the tube, drawing in a continuous sample of air and gases from in vicinity of the patient's mouth and nostrils. The carbon dioxide capnograph module determines the proportion of carbon dioxide in the sampled air and gases. Sampled gases are exhausted from the carbon dioxide capnograph to atmosphere. Alternatively the capnography module may be remote of the gas modulator and may be electronically connected to the gas flow modulator/controller.

A fan 238 can optionally be provided in the housing 220. The fan in is fluid communication with the interior of the housing 220 and atmosphere. The fan can draw ambient air in to the housing 220 or, conversely, draw air out of the housing, in order to cool components located inside the housing. Components that may generate a significant amount of heat comprise the processor and the oscillating proportional valve.

Figure 24:
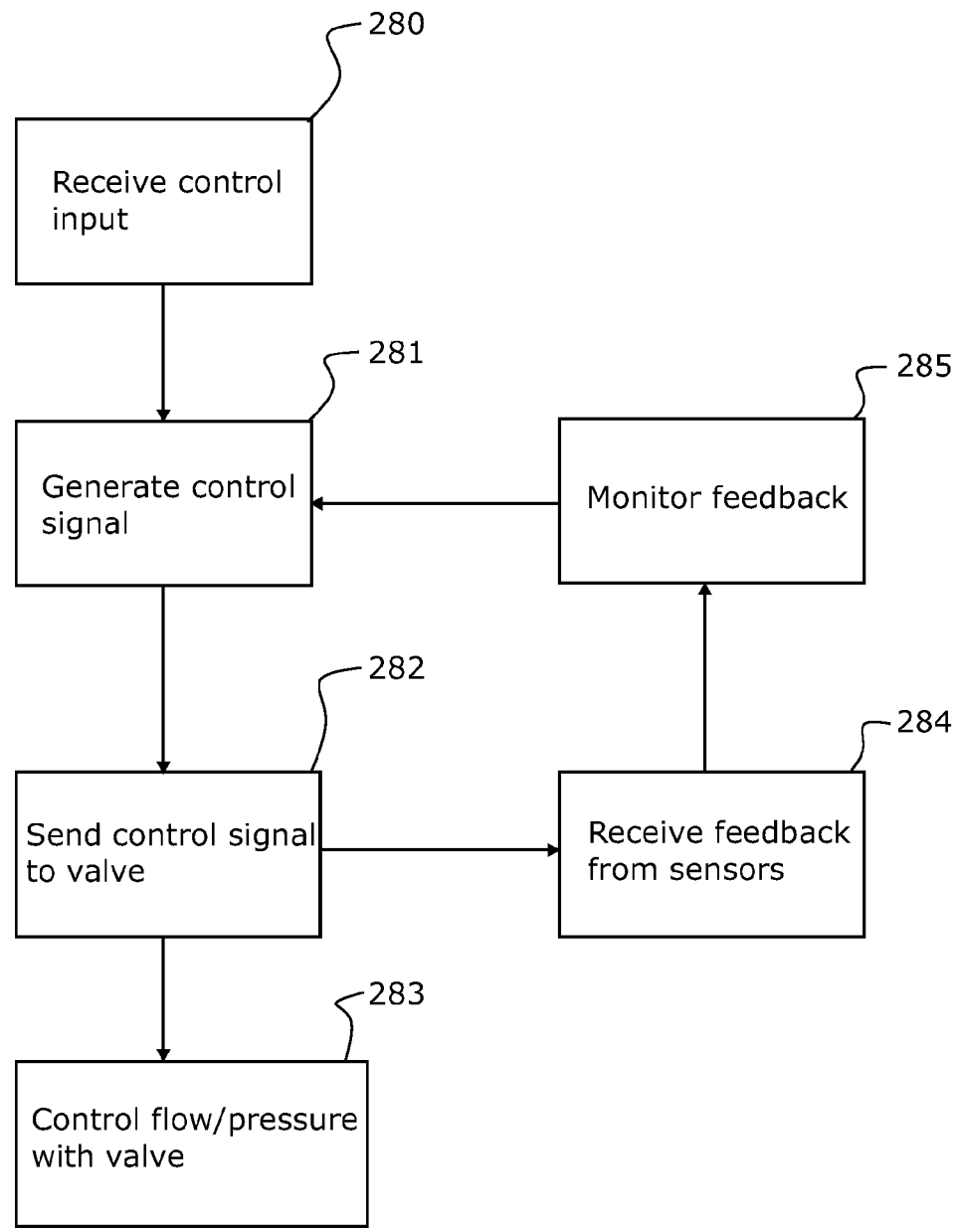
FIG. 24 shows a flow diagram of the method of operation of the gas flow modulator of FIGS. 21, 22, 23 and 25

Referring to FIG. 24, a method of use of the gas flow modulator will now be described. In use, the processor of the gas flow modulator 59 will receive an input control signal 210 that will operate the valve 222, step 280. The control signal can comprise a superposition of frequencies 211a-211c as previously described from an external source. Alternatively, the control signal 210 can be generated internally. Where generated internally, optionally the signal can be generated from user input via the user interface 250 or via stored data. In addition, the processor gas flow modulator optionally receives and monitors sensors inputs/feedback, steps 284, 285, from sensors, such as flow 227 or pressure 225 sensors on board or remote, or via the ports 225a, 231 or via other sensors described herein, which are either located remote to or in the gas flow modulator. The control signal 210 and the sensor(s) signal(s) received at or generated in the processor 265 are utilised by the processor to generate the control signal 221, step 281, which is sent to the control the valve 222, step 282. This might comprise comparing the signal 221 previously sent to the valve 221 in a previous cycle, and comparing it to the actual flow rate waveform of gas flow out of the valve, and correcting the control signal 221 to minimise the differences using feedback, steps 284, 285, 281. The processor passes the control signal 221 to the valve, step 282, which controls the valve, step 284 as described previously. The sensors are continually or periodically monitored steps 284, 285 and the control signal 221 is continually or periodically updated, and sent to the valve, steps 281, 282.

The gas 13 from the inlet 229/223 travels to the proportional valve 222. The proportional valve restriction oscillates according the control signal input 221 that represents a superimposed oscillating waveform. As a result, the flow of gases 13 passing through the valve oscillates according to that waveform.

As noted, the processor compares the signal generated by the flow sensor 227 located within the gas flow modulator 59 with the combined/superimposed oscillating waveform/signal provided to the oscillating proportional valve. The processor subsequently provides corrections to the combined/superimposed oscillating waveform (control signal 221) in order to compensate for any differences between combined/superimposed oscillating waveform provided to the oscillating proportional valve and the signal generated by the flow sensor.

Figure 23:
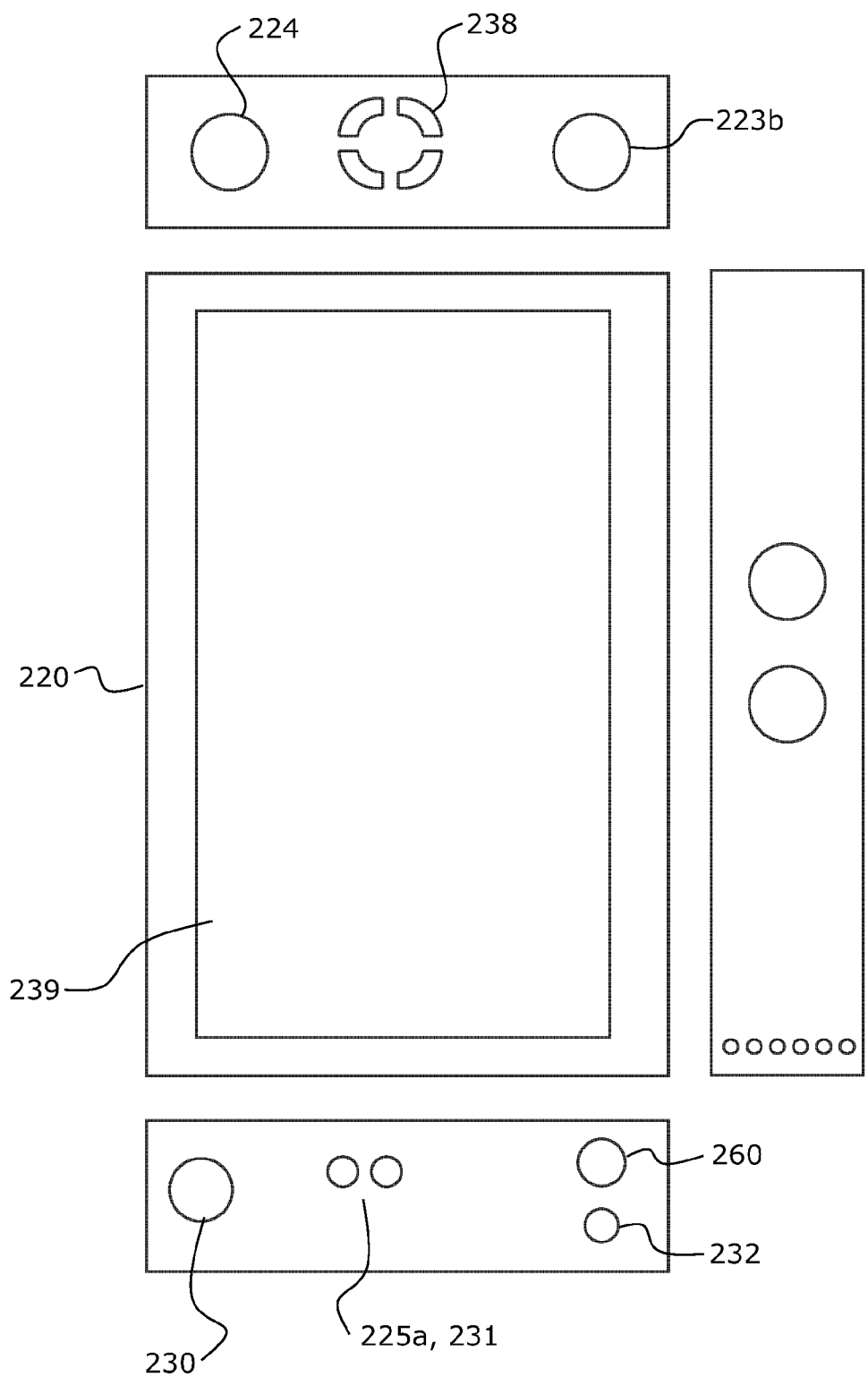
FIG. 23 shows a template of one embodiment of a gas flow modulator housing.

FIG. 23 shows one possible physical embodiment of the housing 220. It has a front, top, side and base. The front can comprise an input output interface 239, which may include a display, touchscreen and/or buttons. The pressure relief valve 224, fan 238 and flow inlet 223b is provided on the top, while the pressure ports 225a, 231, power button 260, power source socket 232 and flow outlet 230 are provided on the base. On one of the sides is provided USB 233, Ethernet 234 and other data/communications ports, and vents can be provided also.

In the earlier mentioned embodiments of the gas flow modulator, the gas flow modulator 59 employs a single proportional valve driven by an oscillating waveform/control signal 210. The oscillating waveform comprises multiple superimposed oscillating frequencies. These oscillating frequencies are superimposed electronically. In an alternative embodiment is envisaged in which multiple valves are provided in the same flow path. The valves may be provided in parallel configuration in the flow path. Each valve is driven by an oscillating waveform/control signal corresponding to a single (or possibly multiple) frequency. As the respective gas flows then recombine in the flow path, these oscillating waveforms are superimposed mechanically.

Figure 25:
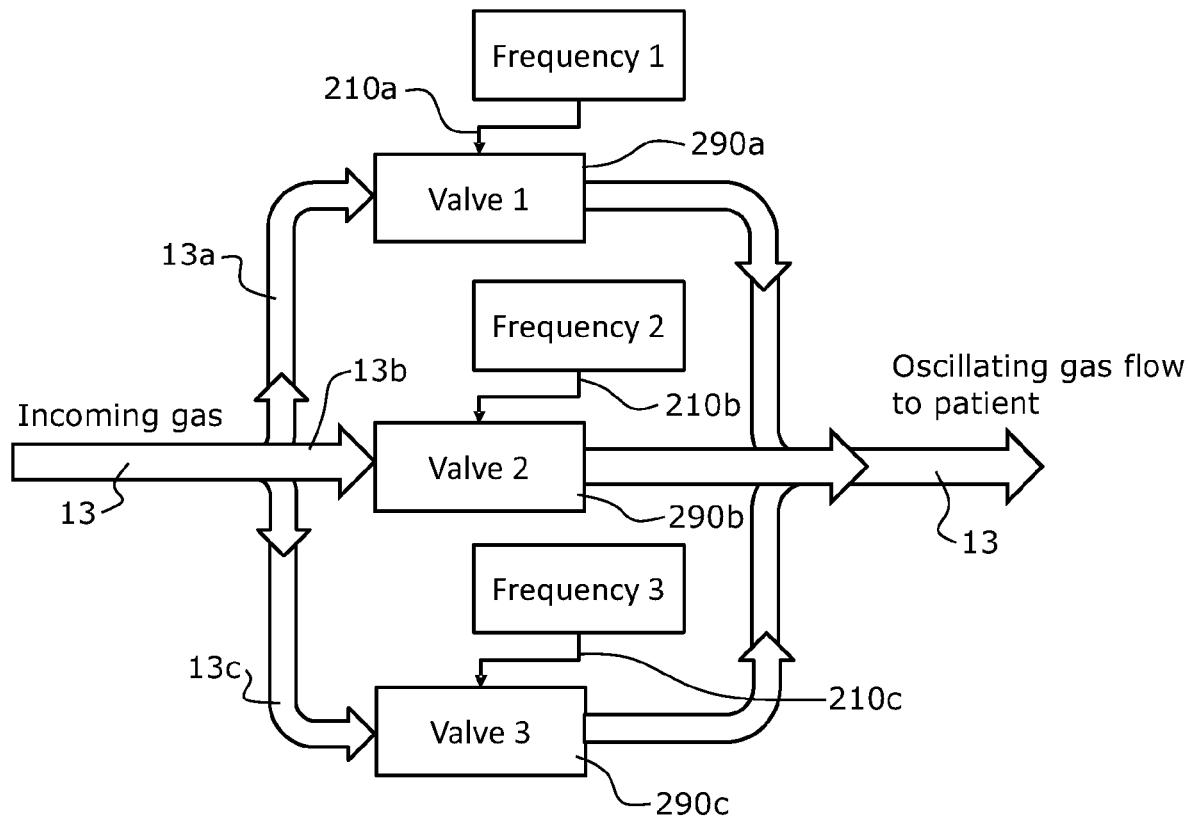
FIG. 25 shows in general form another example of a gas flow modulator with multiple valves.

An example of an alternative general embodiment of the gas flow modulator such as this as shown in FIG. 25. In this embodiment there is not one valve, but multiple valves 290a-290c (or other gas varying devices). Instead of providing a plurality of combined oscillation components as a single control signal 210 to a single valve 212, instead each oscillation component is provided as a single control signal 210a, 210b, 210c to each valve. The gas flow inlet on each valve is multiplexed to come from a single gas flow inlet 13, and the gas flow outlet of each valve is multiplexed to provide a single gas flow outlet 13 with an oscillating gas flow. Each valve 290a to 290c is controlled by an oscillating component 210a to 210c with a frequency as previously determined. The outlet from each valve provides an oscillating or otherwise varying gas flow of a single frequency, which is then combined to provide the overall superimposed gas flow 13 which oscillates (varies) based on the various components. Clearly, each valve 290a to 290c could be controlled with more than one frequency also. Each valve could be considered a gas flow modulator 59, or the whole combination considered a gas flow modulator 59, which can sit anywhere as a single package/device/module/unit in the breathing apparatus system. This embodiment could be implemented in a similar manner to that described and depicted in relation to FIGS. 22 to 23. The method of operating each valve and/or the arrangement overall is the same as described in FIG. 24.

The embodiments above could be configured to just receive a control signal 210 with a single oscillating frequency and provide an output oscillating waveform with a single oscillating frequency.

Another exemplary and non-limiting example of a gas flow modulator 59 is described with reference to FIGS. 26 to 31. Again, in this embodiment, the gas flow modulator can also be termed an "oscillator unit", or a "gas control valve".

The embodiments described with respect to FIGS. 26 to 35 may include similar features to those of the example gas flow modulator 59 described above with respect to FIGS. 21 to 25. Accordingly, like-numbered reference signs are used to indicate these similar features in FIGS. 26-35. It should be understood however, that the embodiment described with respect to FIGS. 26 to 35 may, where compatible, include any of, or all of, the features of the gas flow modulator 59 described above with respect to FIGS. 21 to 25 even where these are not explicitly described as being present in the embodiment of FIGS. 26 to 35.

Figure 26:
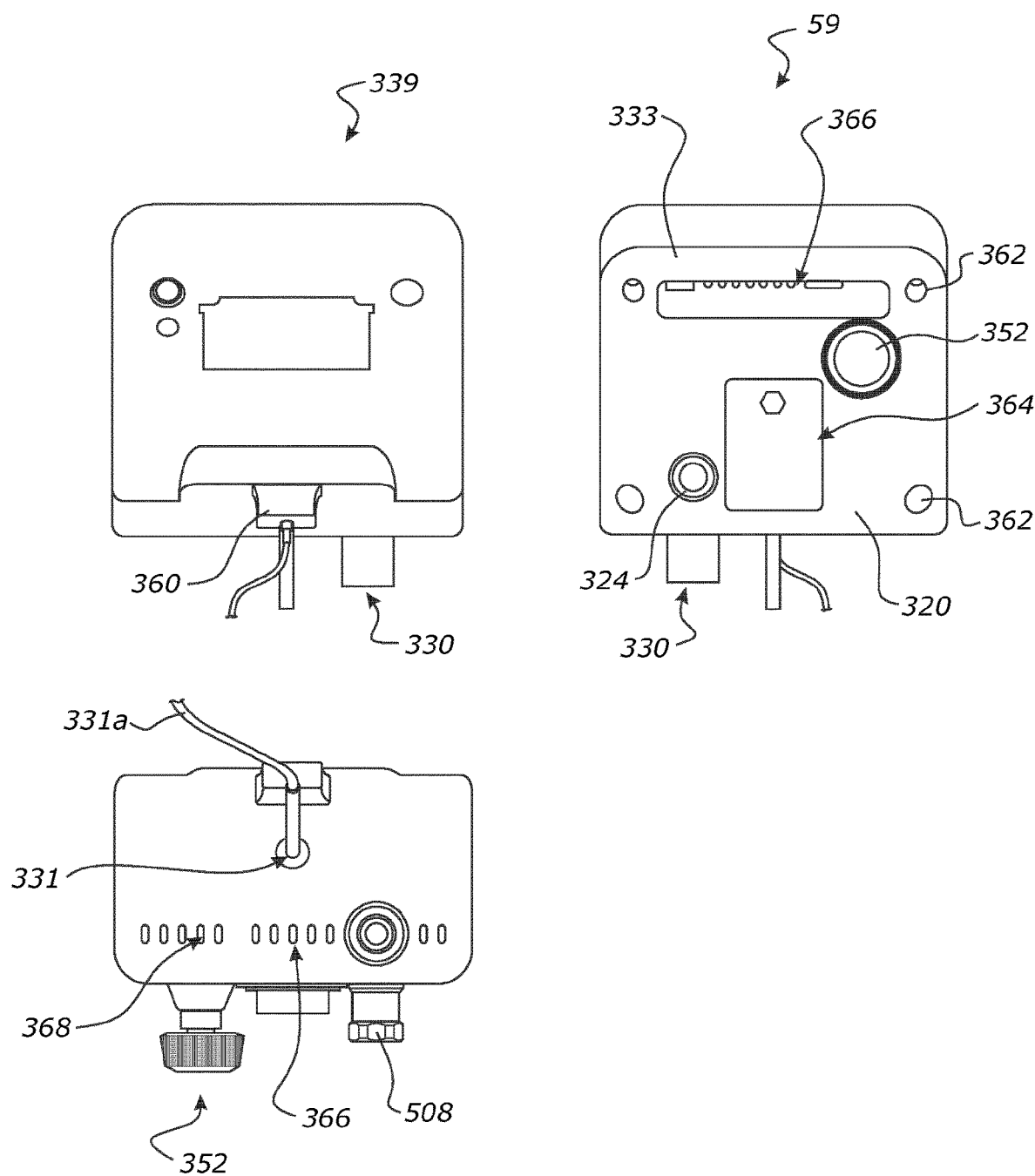
FIG. 26 shows front, back, and bottom views of another embodiment of a gas flow modulator.

FIG. 26 shows that the gas flow modulator 59 comprises a housing 320, which is rectangular in shape. The housing could be formed of polycarbonate, for example, or formed of other plastics.

The housing 320 comprises an input output interface 339, which is located on the front of the housing. The input output interface 339 may include a display, touchscreen and/or buttons. The housing 320 may include a power button.

The housing 320 is provided with a gases inlet 323b for receiving a gases supply tube 229 and a gas flow/supply 13 therefrom. A supply tube fitting 352 couples the gases supply tube to the gases inlet 323b. The gases inlet 323b may be provided on the rear side of the housing 320. The gases inlet 323b may extend out from the housing 320 of the gas flow modulator 59. The housing 320 may include a port that is in fluid communication with the gases inlet 323b.

The housing 320 is provided a gases outlet 330 for receiving and providing gases 13 to a gases delivery tube 14. The gases outlet 330 is provided on the bottom of the housing 320.

The housing accommodates a relief valve 508. The relief valve 508 may be a pressure relief valve. Alternatively, the relief valve 508 may be a relief valve that can be triggered based on flow rate.

The housing 320 also optionally accommodates a gases sampling line or tube 331a. When used, the gases sampling line 331a is received in a gases sampling port 331. The gases sampling port 331 is located on the bottom of the housing 320.

The housing 320 is also provided with a port for optionally receiving a data cable 360. The data cable 360 may be in communication with a pulse oximetry probe, for example. The data cable port may be provided on the bottom of the housing 320. The housing 320 may also comprise a removable data storage port (such as for a USB, SD card, or the like) 333. The removable data storage port 333 is located on the rear of the housing 320. The housing 320 may also comprise one of, or a combination of, any of the following ports: a power supply port, a USB port, a HDMI port, and an Ethernet port.

Figure 27:
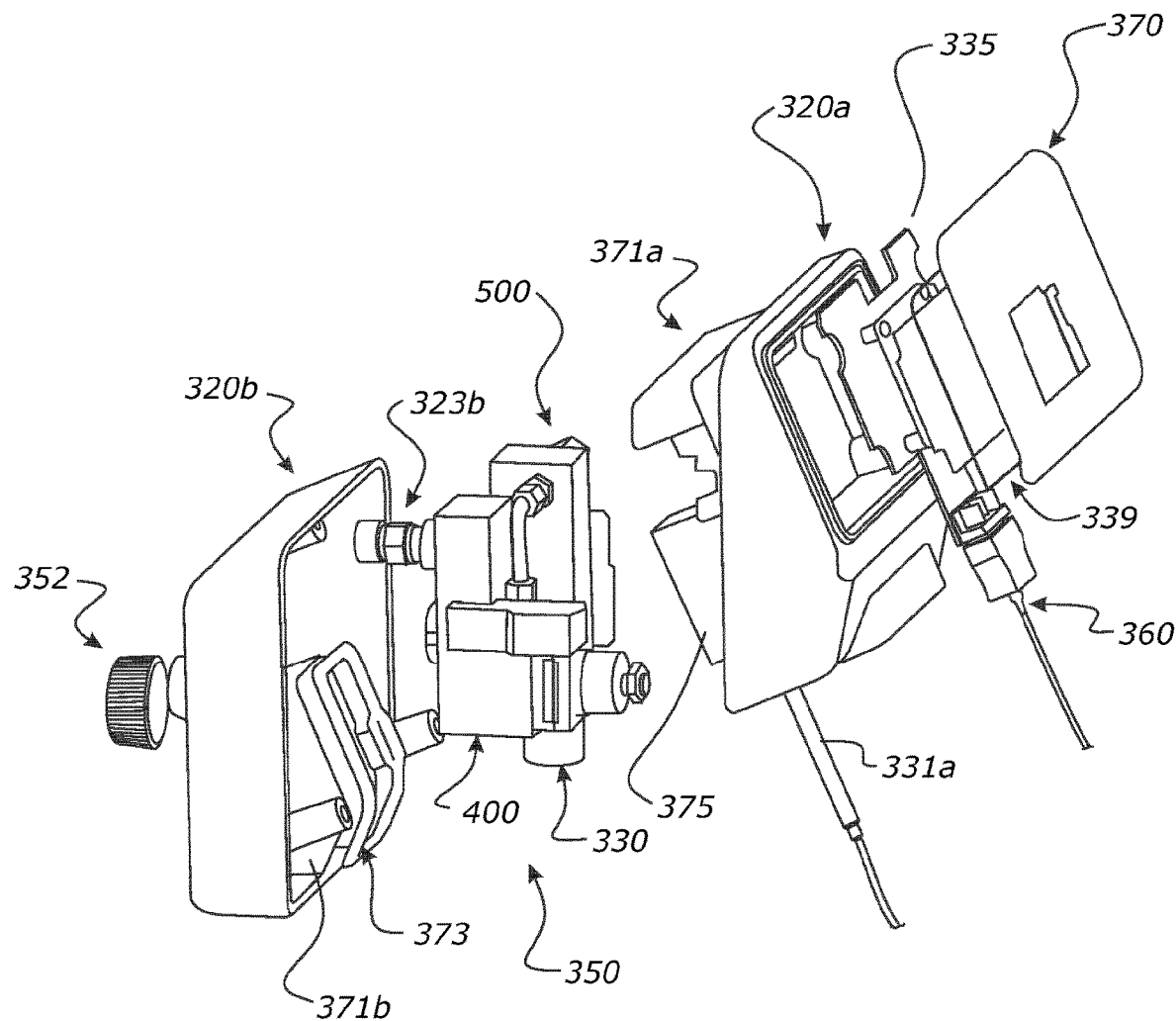
FIG. 27 shows an exploded view of the gas flow modulator of FIG. 26.

The housing 320 may be of more than one part, for example two parts 320a, 320b as shown in FIG. 27. The parts may fixed together by screws, which are accommodated in screw holes 362 in the housing 320.

The housing 320 may comprise a mounting bracket 364. The mounting bracket 364 may be configured to allow the housing 320 to be mounted on a vertical pole.

The housing 320 may include electrical vents 366. The electrical vents 366 allow for natural ventilation of the electronics housed in the housing 320. Alternatively, a fan may be provided in the housing 320. The fan in is fluid communication with the interior of the housing 320 and atmosphere. The fan can draw ambient air in to the housing 320 or, conversely, draw air out of the housing, in order to cool components located inside the housing.

The housing 320 may also include pneumatic vents 368. The pneumatic vents 368 may allow gases to be vented from the housing 320. For example, the pneumatic vents 368 may allow gases to be vented from the housing 320 in the event of a gases leak from the pneumatic fittings located within the housing 320.

FIG. 27 shows an exploded view of the gas flow modulator of FIG. 26. The housing 320 comprises two components: a front part 320a and a rear part 320b. The input output interface 339 is mounted on a PCB 335. The input output interface 339 may be surrounded, on assembly, by a bezel 370. The bezel 370 may be printed with information that is useful to a user/carer. For instance, the bezel may indicate the location of an on/off power button or provide a graphical indication of the type of alarm being indicated from the input output interface 339.

The PCB 335 may be a single PCB or multiple PCBs stacked on one another. The multiple PCBs may be dedicated to different respective functions, for instance one PCB could be dedicated to interfacing with the input output interface 339.

As described above with respect to the gas flow modulator 59 of FIGS. 21-25, the PCB 335 has inputs/ouputs/ports (communication interface) for coupling to communications channels to a controller for operating the modulator. The PCB 335 and the housing 320 can be coupled to the controller 19 of the breathing apparatus 11 it will be used with. This coupling may be via the data cable 360. Alternatively, a controller (processor), which operates the gas modulator 59, can be provided on the PCB 335.

The front part 320a and rear part 320b of the housing 320 each respectively include mounting supports 371a and 371b that support the gases flow path components of the gas modulator 59.

The housing 320 may accommodate a gases sensor 375. The gases sensor 375 may receive a sample of gases from the gases sampling line 331a via the gases sampling port 331. For example, the gases sampling line 331a may collect a continuous sample of air and gases from in vicinity of the patient's mouth and nostrils. Sampled gases may be exhausted from the gases sensor 375 to atmosphere through the pneumatic vents 368. In addition, or alternatively, sampled gases may be exhausted from a dedicated tubing and port assembly.

The gases sensor 375 may an exhaled/expired gases sensor. The gases sensor 375 may be a nitrogen sensor. The gases sensor 375 may be a carbon dioxide sensor. If the gases sensor 375 is a carbon dioxide sensor, the gases sensor 375 maybe in communication with a carbon dioxide capnograph module as described above with respect to the gas modulator 59 of FIGS. 21-25. The capnograph module may be located within the housing 320. The carbon dioxide capnograph module determines the proportion of carbon dioxide in the sampled air and gases. The capnograph module may be configured to determine a waveform of the carbon dioxide that can be displayed on the input output interface 339. Alternatively, the gases sensor 375 may be in communication with a remote capnograph module by way of an electronical connection to the gas flow modulator/controller.

The housing 320 also comprises a housing gasket 373. The housing gasket 373 may separate the housing 320 into separate compartments. The housing gasket 373 may separate the housing 320 into a plurality of separate compartments. For example, the housing gasket 373 may separate the housing 320 into two separate compartments. One of the separate compartments may house some of the electronic components, for example the PCB 335 and input output interface 339. The other separate compartment may house pneumatic components as set out below and some low powered electronics, for example PCB 520 as discussed below. The housing gasket 373 seals against oxygen entering the PCB regions of the gas flow modulator 59. In particular, the gasket 373 seals off the gases flow from entering the PCB area. Sealing off the gases from reduces the risk of a fire due to the high flow/high oxygen concentrated gas being close to electronics, which can arc for example.

The gas flow modulator 59 may comprise a modular manifold arrangement. The gas flow modulator 59 may comprise a plurality of sub-manifolds. For example, the gas flow modulator may comprise two, or a pair of, sub-manifolds. For example, when the housing 320 of the gas flow modulator 59 is assembled together, the mounting supports 371a and 371b support a modular manifold arrangement 350 comprising an inlet manifold 400 and an outlet manifold 500 of the gas flow modulator 59. The inlet manifold 400 and an outlet manifold 500 are shown without the housing 320 in FIG. 28.

The modular manifold arrangement 350 allows for easier cleaning and easier servicing of the gas flow modulator 59. The modular manifold arrangement 350 also allows for easy replacement of damaged parts. For instance, the inlet manifold 400 or outlet manifold 500 could be each replaced independently or together. Separating the manifolds in this way also helps to isolate various electrical circuits, sensors and PCBs from potential fire is due to the separate nature of the manifolds. Furthermore, separating the sub-manifolds allows the PCBs and sensors to be isolated so that the risk of a fire or explosion is reduced. The modular nature of the sub-manifolds also allows for customization of the gases path within the housing 320. The separation of the sub-manifolds also protects the gas flow modulator 59 components from any sudden spikes in flow or pressure.

Gases flow, from the gases supply tube 229, through gases inlet 323b and the components of the inlet manifold 400 and then through the components of the outlet manifold 500 to exit through the gases outlet 330. A gases connection flow tube 450 connects the inlet manifold 400 with the outlet manifold 500. The gases connection flow tube 450 may be flexible. The gases connection flow tube 450 may be made from polyurethane tube, for example. By being a flexible flow tube allows for a smooth flow path. This reduces corners in the flow path, which therefore reduces areas where resistance to flow can increase. The flexibility of the tube 450 also allows different configurations of the sub-manifolds. The gases connection flow tube 450 provides separation between the inlet 400 and outlet 500 manifolds, which, as discussed above, helps isolate electrical circuits and sensors to reduce the risk of fire. This especially critical as it is expected the gas flow modulator 59 will be operated with a pure oxygen gas flow.

The flow path through the inlet manifold 400 and outlet manifold 500 should be as smooth as possible to prevent pressure loss and turbulence. Given that the gas flow modulator 59 is expected to be used with a pure oxygen supply, having a smooth flow path will help reduce the chance of particles striking the wall defining the flow path through the manifolds. Furthermore, having a smooth flow path will help reduce spark formation from particles striking the wall defining the flow path. Particulate matter striking any sharp corners is more likely to generate sparking. The kinetic energy from particle impact may generate heat, which may ignite the particle and/or the wall defining the flow path if there is sufficient energy and the auto-ignition temperature of the materials is reached. Such sparks can lead to an explosion or fire if there is a spark resulting from any particles striking flow path in the inlet 400 and outlet 500 manifold walls. Hence, the flow path has rounded corners.

Furthermore, even if there is a fire initiated by a spark, the fire is more likely to be contained within the manifold concerned because the manifolds are separated by the gases connection flow tube 450. Additionally, the electronics on one-sub-manifold, e.g. the PCBs, can be separated from the other sub-manifolds and this also helps to mitigate the risk of a fire on the PCBs.

The components of the inlet manifold 400 and outlet manifold 500 will now be described with regards to FIGS. 28-31. FIG. 31 is a schematic flow chart of the inlet manifold 400 and the outlet manifold 500 shown in FIG. 28.

The components of the inlet manifold 400 are assembled on a manifold inlet block 412. Similarly, the components of the outlet manifold 500 are assembled on an outlet manifold block 512. The manifold blocks 412, 512 may be made from brass and nickel plated. The manifold blocks 412, 512 are machined as necessary in order to mount the appropriate components.

Figure 28:
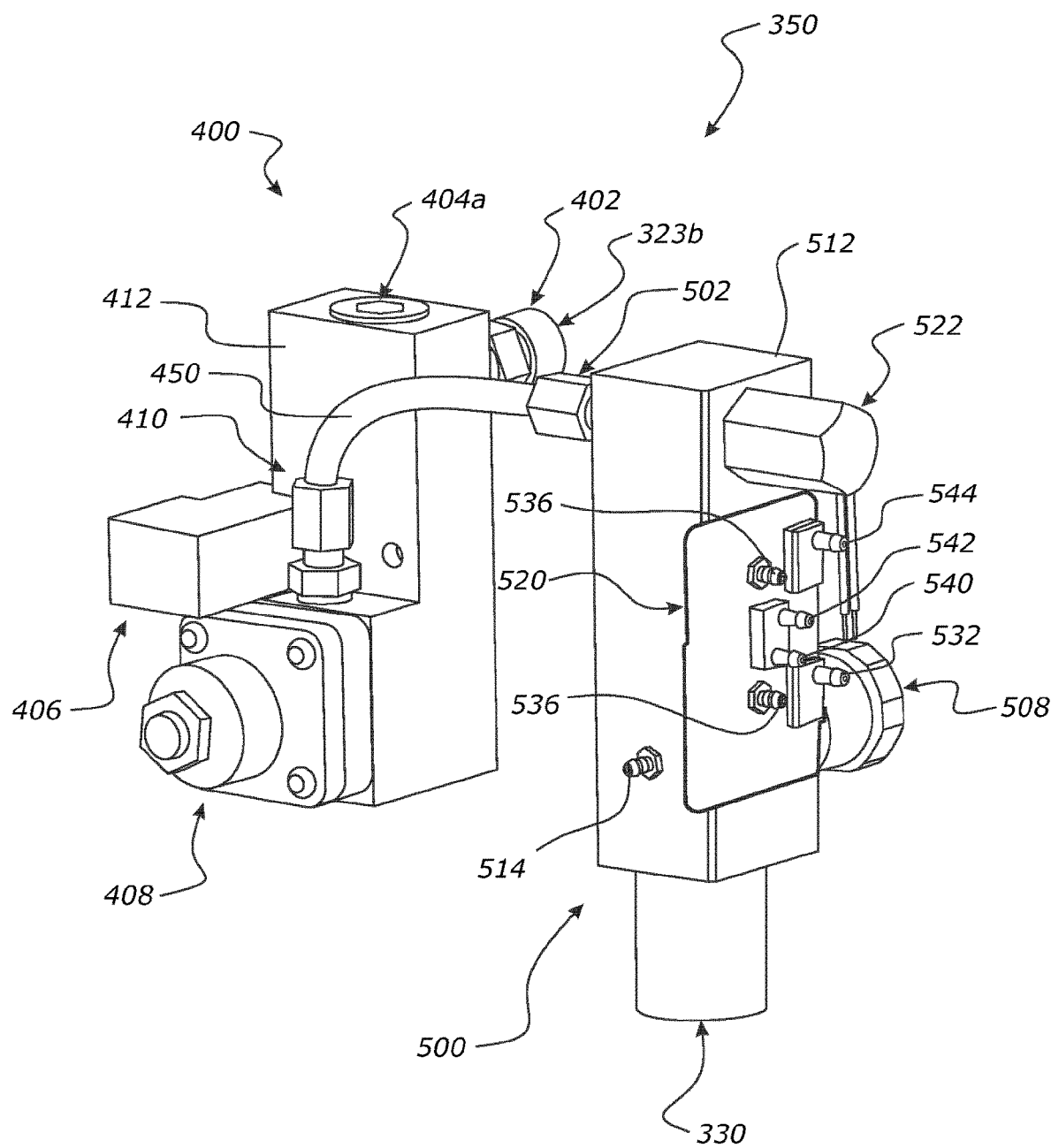
FIG. 28 shows an inlet manifold and an outlet manifold of the gas flow modulator of FIG. 26.
Figure 29:
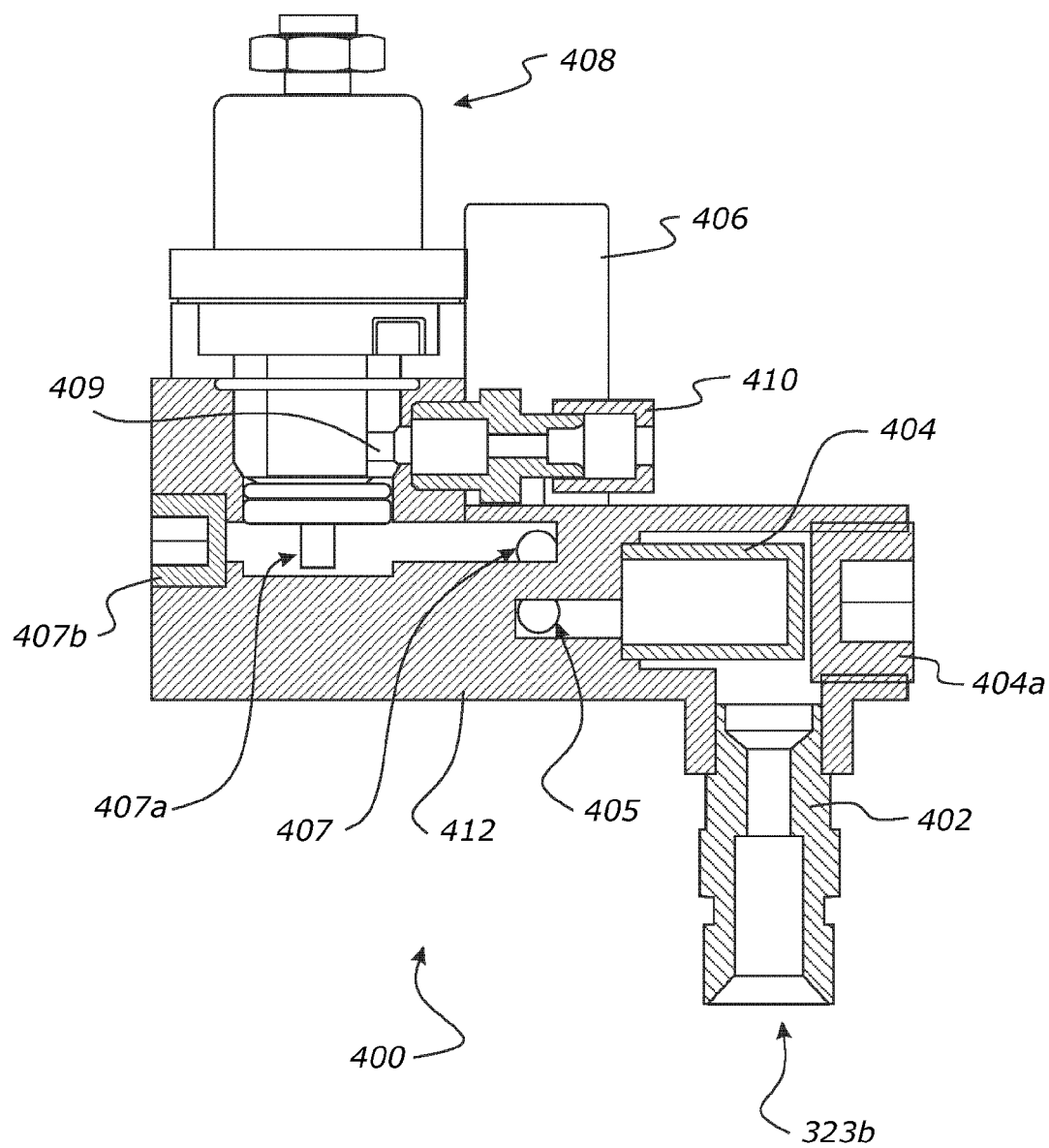
FIG. 29 shows a cross-sectional view through the inlet manifold shown in FIG. 28.

With reference to FIGS. 28 and 29 in particular, the inlet manifold 400 comprises a gases inlet fitting 402, an inlet filter 404, a solenoid valve 406, a pressure regulator 408 and an outlet compression fitting 410. Gases flow through each of these components in series until they exit the inlet manifold 400 through the gases connection flow tube 450. These components are mounted in, or on, the inlet manifold block 412.

The gases inlet fitting 402 may optionally include a check valve 403 (see schematic FIG. 31). Gases pass from the inlet fitting 402 to the inlet filter 404.

The inlet filter 404 is shown in cross-section in FIG. 29. As FIGS. 28 and 29 show, a filter plug 404a seals the blind hole bored in the inlet manifold block 412 to accommodate the inlet filter 404. The plug 404a can be seen at the top of the inlet manifold block 412 in FIG. 28. The plug 404 may be a ⅜" brass plug.

The inlet filter 404 protects the proportional valve mounted in the outlet manifold from particles that enter the inlet manifold via the gases inlet 323b. The inlet filter is required to provide protection from particles damaging the proportional valve and its components due to the fact that the particles are travelling at high speed as a result of the high flow rates involved in delivering the gases to a patient. The inlet filter 404 may be a sintered filter. The inlet filter 404 may be a filter with a 15 μm pore size. The inlet filter 404 may be a single layer of filter material. Alternatively, inlet filter 404 may have multiple layers of filter material. Furthermore, the inlet filter 404 acts to prevent any particulate matter from being delivered to the patient as a part of the high flow rate of gases.

Located between the inlet filter 404 and the pressure regulator 408 is the solenoid valve 406. The solenoid valve 406, however, could be located elsewhere in the inlet manifold 400. The solenoid valve 406 is a shutdown valve. Thus in other words, the solenoid valve 406 is a safety valve that can be activated of the pressure and/or flowrate rises above a certain threshold. The solenoid valve 406 acts as a safety backup feature which is operated/controlled electronically, as opposed to mechanically, to shut down the flow of gases.

Fluid communication passageways 405 are provided in the inlet manifold block 412 between the inlet filter 404 and the solenoid valve 406. Similarly, fluid communication passageways 407 are provided in the inlet manifold block 412 between the solenoid valve 406 and the pressure regulator 408. Fluid communication passageways 407 leads to the pressure regulator 408 inlet port 407a. See FIG. 29. The gases flow through the manifold block 412 in these passageways. For ease of manufacture the passageways 405, 407 can be drilled in the block 412. The passageway 407 may be sealed with a plug 407b. The plug 407b may be a ⅛" brass plug.

The pressure regulator 408 regulates the maximum amount of flow through the gas flow modulator 59. The pressure regulator 408 also assists in smoothing some of the gases flow so as to reduce turbulence in the gases flow. Additionally, the pressure regulator 408 has a safety function. In the event that the proportional valve 522 mounted in the outlet manifold 500 fails open, then the pressure regulator 408 maintains the outlet pressure of the gases flow delivered to the proportional valve at a constant pressure. For example, in the event the proportional valve fails open, the pressure regulator 408 caps the flow at 100 L/minute as opposed to over 250 L/minute that can be delivered to the gas flow regulator 59 through the inlet 323b, for example, from the wall supply.

Downstream of the pressure regulator 408 the gases flow passes through the pressure regulator outlet port 409 and then exits the inlet manifold through the outlet compression fitting 410. The outlet compression fitting 410 is coupled to the gases connection flow tube 450 through which the gases flow travels to the outlet manifold 500.

As FIG. 31 shows, a temperature reading of the gases flow may be taken in the inlet manifold 400. A temperature sensor 414 is provided for this purpose and measures the flow temperature at a location between the solenoid valve 406 and the pressure regulator 408. However, the temperature sensor 414 may be located at any location desired along the flow path in the inlet manifold 400.

Figure 30:
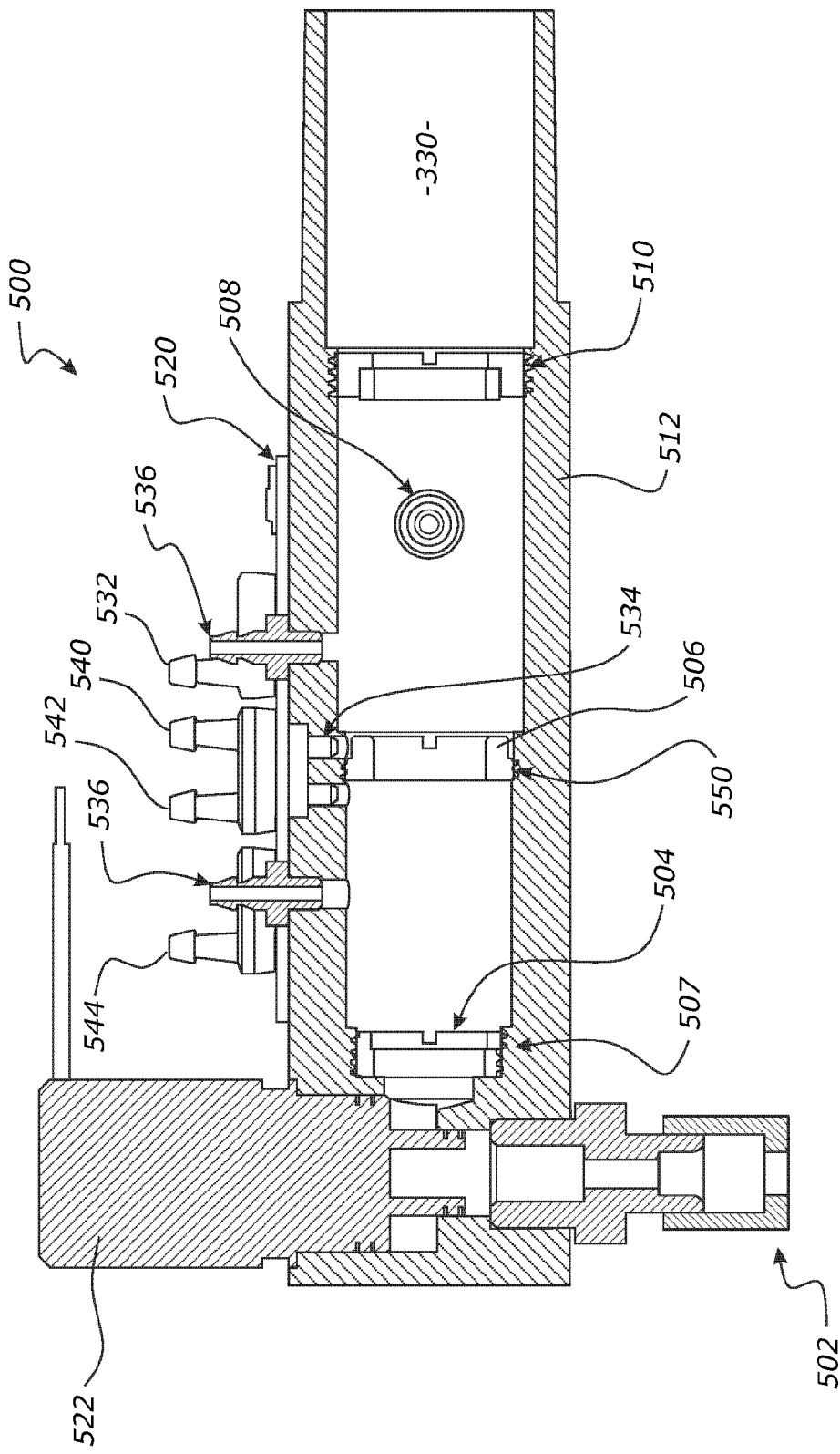
FIG. 30 shows a cross-sectional view through the outlet manifold shown in FIG. 28.
Figure 31:
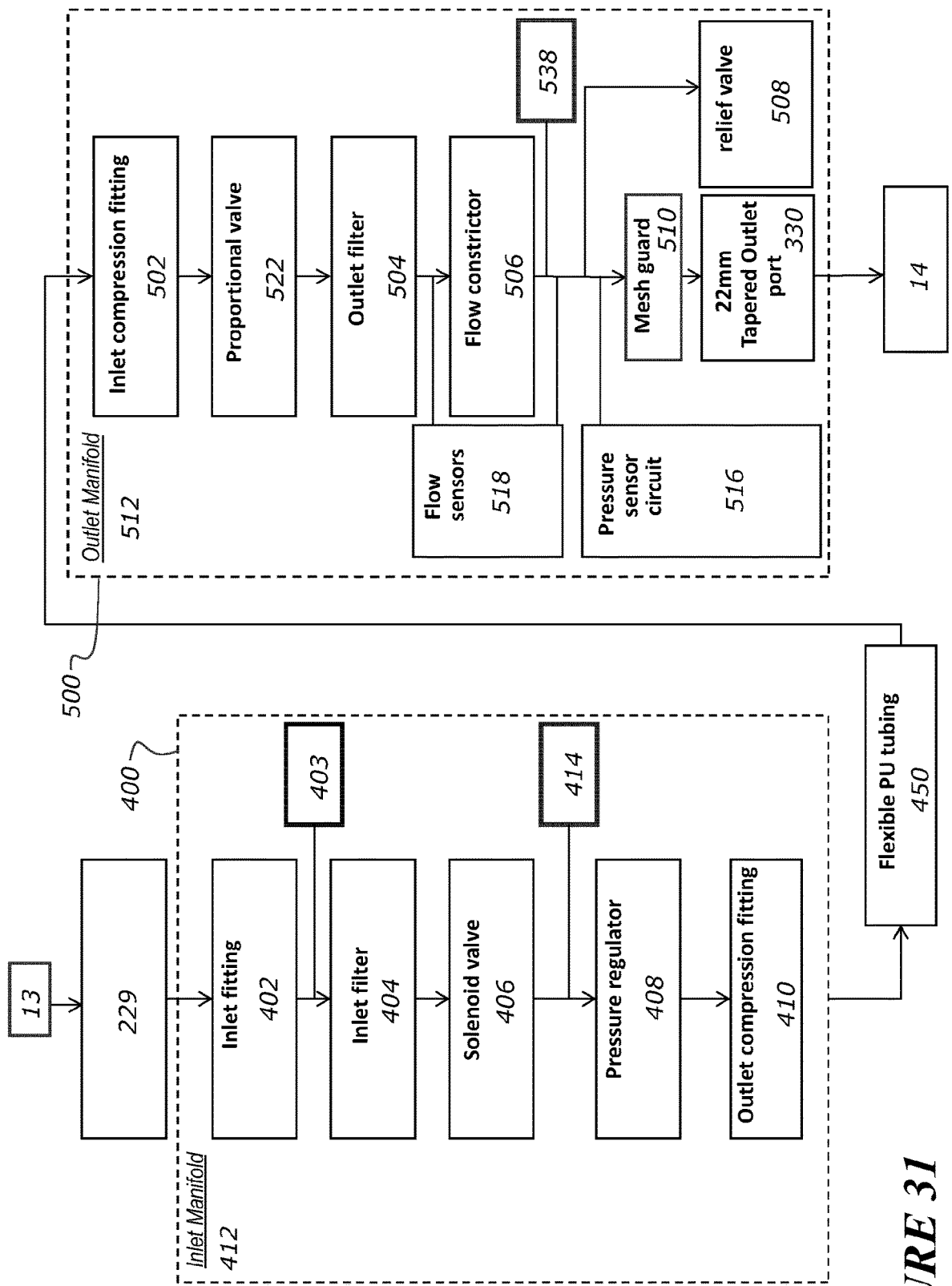
FIG. 31 is a schematic showing the flow path of gases through the inlet manifold and outlet manifolds of the gas modulator of FIG. 26.
Figure 33:
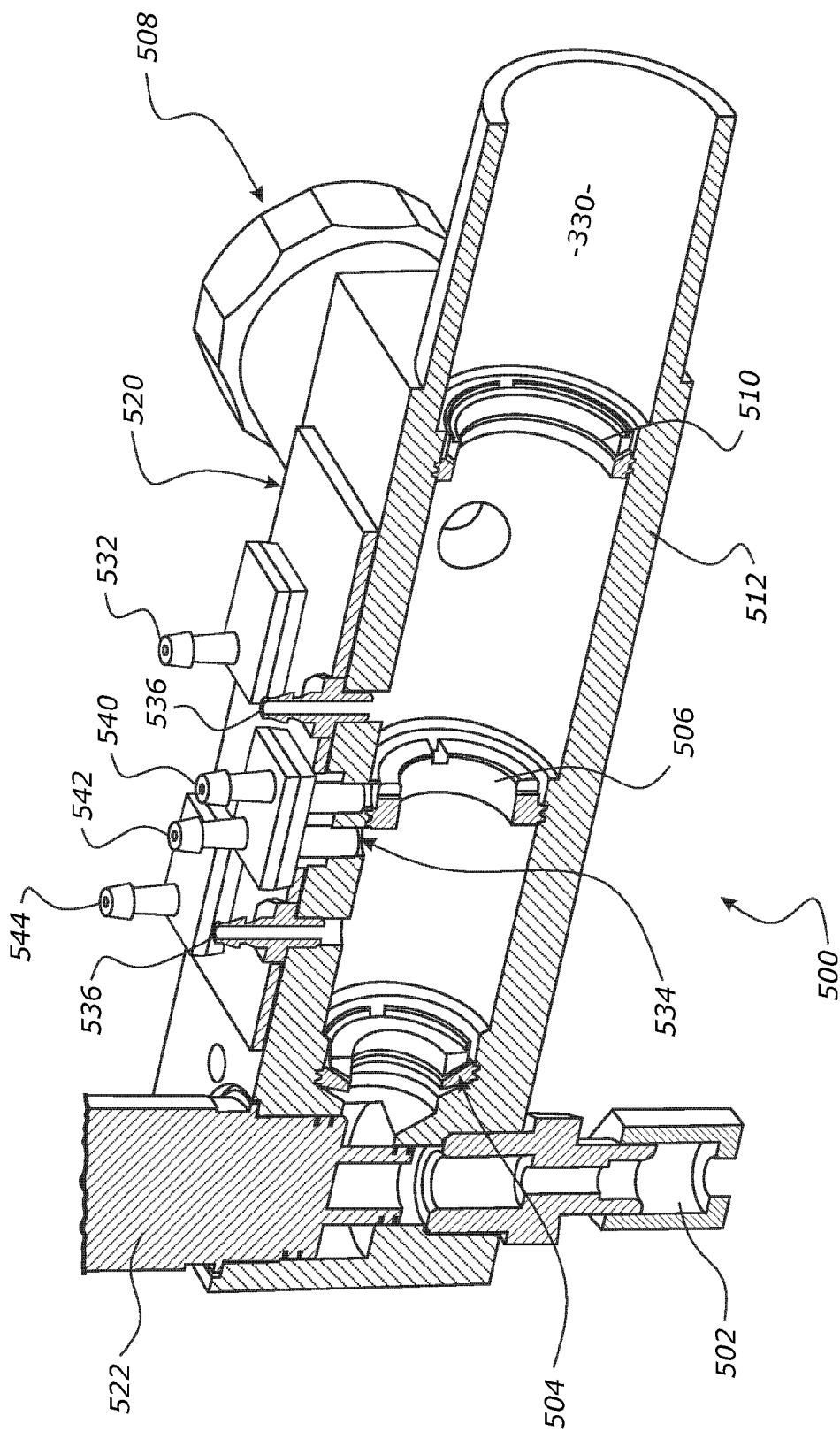
FIG. 33 is a perspective view of the outlet manifold of FIGS. 28 and 30.

With reference to FIGS. 28, 30 and 33 in particular and in order relative to the flow path, the outlet manifold 500 has an inlet compression fitting 502, a proportional valve 522, an outlet filter 504, flow constrictor 506, a relief valve 508, and a mesh guard 510. The outlet manifold 500 accommodates the gases outlet 330. Gases flow, from the gases connection flow tube 450, through each of these components in series until from the they exit the outlet manifold 500 through the gases outlet 330 into a gases delivery tube 14. The components are mounted in, or on, the outlet manifold block 512.

The gases outlet 330 may be a standard tapered outlet port connector adapted to couple to a patient gases delivery circuit/tube. The gases outlet 330 may be a 22 mm medical taper. As can be seen in FIG. 30, the mesh guard 510 may be located immediately upstream of the flow passage defined by the gases outlet 330. Alternatively, the mesh guard 510 may be positioned in the flow passage defined by the gases outlet 330 or at the downstream end of the gases outlet 330. The mesh guard 510 prevents instruments being inserted into the outlet manifold 500 of the flow modulator 59. The mesh guard may be a stainless steel mesh. The mesh guard may be a TWP mesh disc.

From the inlet compression fitting 502, the gases flow enters the proportional valve 522.

Optionally, an additional filter may be provided in the outlet manifold 500 between the inlet compression fitting 502 and the proportional valve 522. This filter may protect the proportional valve from particles that may fly into the proportional valve 522 thereby protecting the components of the proportional valve 522. This additional filter may be a sintered filter and may have a 15 μm pore size. Alternatively, the additional filter may have 40 μm pore size. The filter may be a single layer of filter material or maybe a multiple layers of filter material.

As described in above in respect of the gas flow modulator 59 of FIGS. 21 to 25, the proportional valve 522 subjects the gases flow to oscillations to provide the therapy described herein. The operation and control of the proportional valve 522 is described above along with the component oscillation frequencies.

The gases flow leaving the proportional valve 522 passes through the outlet filter 504, which is located in the flow path. The outlet filter 504 is mounted in the outlet manifold block 512 on an outlet filter assembly 507. The outlet filter assembly 507 is shown in cross-sectional FIG. 30.

The outlet filter 504 acts to smooth the gases flow and reduce turbulence. The outlet filter 504 acts to guide the flow in a more unitary bulk flow stream toward the flow constrictor 506. The outlet filter 504 acts to protect the proportional valve from particles that may fly into the proportional valve 522 when gases are being drawn back into the gas flow modulator 59. Particulate matter may be drawn back into the gas flow modulator 59 due to pressure differentials. The outlet filter 504 also prevents dust or other contaminants from entering the proportional valve body when the gas flow modulator 59 is not in use (for example, in storage).

The outlet filter 504 may be a mesh filter. The mesh filter may be a stainless steel mesh. The mesh filter may be a TWP mesh disc. The outlet filter 504 may be a sintered filter. The outlet filter 504 may have a 40 μm pore size. The outlet filter 504 may have a 15 μm pore size. The outlet filter 504 may have a single layer of filter material or multiple layers of filter material.

Downstream of the outlet filter 504, the gases flow passes through the flow constrictor 506. The flow constrictor 506 acts to smooth the gases flow as it passes through the outlet manifold 500 and is discharged through the gases outlet 330. The flow constrictor 506 provides a pressure drop to improve the calculation of the gases flow rate. As described below, pressure taps, which are in fluid communication with pressure sensors, are provided into the flow path in various positions to allow the flow calculations to be made.

The pressure relief valve 508 is positioned downstream of the outlet filter/constrictor 506 and adjacent to the gases outlet 330. The pressure relief valve 508 acts to limit the pressure of the gases downstream of the proportional valve 522 and exiting the outlet manifold 500. Furthermore, the pressure relief valve 508 can be used as an additional safety valve to relieve the pressure of the gases flow. In other words, if the pressure in the gases flow exceeds a predetermined threshold then the pressure relief valve 508 will open and a portion of the gases flow will be vented to atmosphere. The pressure relief valve 508 may be an electronically operated pressure relief device. The predetermined threshold may be an electronically stored pre-set pressure. The pressure relief valve 508 may be a mechanical pressure relief device. The predetermined threshold may be a pre-set pressure on the mechanical pressure relief device. Alternatively, a mechanical pressure relief device and an electronically operated pressure relief device may be provided. Activation of the pressure relief valve 508 is most likely to take place if an occlusion takes place. For example, if the outlet port 330 becomes blocked.

As shown in FIGS. 28, 30 and 33, a manifold PCB 520 is mounted to the manifold block 512. The manifold PCB 520 may be in communication with the PCB 335, located on the front housing 320a. Optionally, the controller (processor) that operates the gas modulator 59 could be provided on the manifold PCB 520 instead of on the PCB 335.

A number of pressure sensors may be located on the manifold PCB 520 or another one of the PCBs of the gas flow modulator 59. See FIGS. 28, 30 and 33, which show the pressure sensors mounted on the manifold PCB 520.

An outlet pressure sensing port 514 may be included in the outlet manifold block 512. The outlet pressure sensing port 514 is a pressure tap (i.e. in fluid communication) to the gases flow passageway through the outlet manifold block 512. The outlet pressure sensing port 514 allows the delivered outlet pressure (at the gases outlet 330) to be determined through a pressure sensing circuit 516, which is shown in FIG. 31. The pressure sensing circuit 516 may comprise a pressure sensor and a coupling tube that fluidly couples the pressure sensor to the outlet pressure sensing port 514.

The pressure sensing circuit 516 may comprise a pressure sensor 532 mounted on the manifold PCB 520. A coupling tube may fluidly couple the pressure sensor 532 to the outlet pressure sensing port 514. The pressure sensor 532 may measure the absolute pressure in the gases outlet 330.

Alternatively, the outlet pressure sensing port 514 may be fluidly coupled to two of the pressure sensors. Coupling the outlet pressure sensing port 514 to two pressure sensors provides redundancy in case one of the pressure sensors fails.

One or more of the pressure sensors 532 that are fluidly coupled to the outlet pressure sensing port 514 may be in electrical communication with the solenoid valve 406 of the inlet manifold 400. If the delivered outlet pressure of the gases exiting the outlet manifold 500 is determined to exceed a predetermined threshold pressure by the pressure sensors 532, then the controller of the gas flow modulator 59 may instruct the solenoid valve 406 to activate and shut down the gases flow.

One or more of the pressure sensors 532 that are fluidly coupled to the outlet pressure sensing port 514 may be in electrical communication with the pressure relief valve 508. If the delivered outlet pressure of the gases exiting the outlet manifold 500 is determined to exceed a predetermined threshold pressure by the pressure sensors 532, then the controller of the gas flow modulator 59 may instruct the pressure relief valve 508 to activate and vent the gases flow to atmosphere if the pressure is too high.

A differential pressure sensor 534 may also be provided mounted on the outlet manifold block 512. The differential pressure sensor 534 is mounted in a recess in the outlet manifold block 512. The differential pressure sensor 534 consists of two pressure taps, which are in fluid communication with the outlet flow passageway. One of the pressure taps is in fluid communication with the passageway upstream of the flow constrictor 506. The other of the pressure taps is in fluid communication with the passageway downstream of the flow constrictor 506. As will be well understood, measuring the static pressure of the gases flow both upstream and downstream of the flow constrictor 506 allows the flow rate of the gases flow to the determined/inferred.

The static pressure difference, as determined from the differential pressure sensor 534, may be correlated to a flow value based on a look-up table or a pressure vs flow curve. The look-up table or pressure vs flow curve may be created by calibrating the differential pressure sensor 534 (or other sensors as described below). The look-up table or pressure vs flow curve resulting from the calibration may be stored in a memory of the pressure sensor or in a processor/controller mounted on one of the gas flow modulator 59 PCBs described herein. The look-up or pressure vs flow curve resulting from the calibration may also be stored in a processor/controller and used as a reference for the measurements of other pressure sensors (as described below) in order to determine the gases flow rate value.

This arrangement is shown schematically in FIG. 31, in which flow sensors 518 indicate the position of the pressure taps/measurements. Schematically, the measurements may be taken between the proportional valve 522/outlet filter 504 and the flow constrictor 506 and also between the flow constrictor 56 and the gas outlet 330. The flow sensors 518 may be used to determine the flow across the flow constrictor 506 and, therefore, through the gas flow modulator 59. Furthermore, the flow sensor 518 information may be used to display the flow rate being delivered to the patient on the input output interface 339. Alternatively, the flow sensor 518 information may be used by the controller to further control relief valve 508 if the flow is above a particular threshold.

Another set of pressure ports 536 may be provided on the outlet manifold block 512. The additional set of pressure ports 536 allow an additional flow sensor to be provided. As can be seen from FIGS. 28, 30 and 33, the pressure ports are in fluid communication with the gases flow path and straddle the flow constrictor 506. In other words, one of the pressure ports 536 is a pressure tap located upstream of the flow constrictor 506 and the other pressure port 536 is a pressure tap located downstream of the flow constrictor 506. Each of the pressure ports is a part of a pressure sensing circuit. A first pressure sensing circuit may comprise a pressure sensor 540, a coupling tube and the pressure tap 536 located downstream of the flow constrictor 506. A second pressure sensing circuit may comprise a pressure sensor 542, a coupling tube and the pressure tap 536 located upstream of the flow constrictor 506. The coupling tubes fluidly couple the pressure sensors 540, 542 to their respective pressure ports 536. The pressure sensors 540, 542 may be mounted on the manifold PCB 520.

The first and second pressure sensing circuits allow the pressure sensors 540, 542 to determine the respective static pressure of the gases flow upstream and downstream of the flow constrictor 506. Again, as with the differential pressure sensor 534, measuring the static pressure both upstream and downstream of the flow constrictor with these pressure ports 536 and sensors 540, 542 allows the flow rate of the gases flow to the determined/inferred. Hence, the pressure ports 536 and pressure sensors 540, 542 act as a second source of flow rate calculations in the event of a failure of the differential pressure sensor. The pressure ports 536 and pressure sensors 540, 542 also provide redundancy in determining the static pressure of the gases flow travelling through the outlet manifold 500 passageways on either side of the flow constrictor 506.

The differential pressure sensor 534 and pressure sensors 540, 542 also provide pressure measurement redundancy with respect to safely controlling the pressure in the flow path in the event of a malfunction. In addition to the pressure relief valve and the a pressure sensor 532, the differential pressure sensor 534 and pressure sensors 540, 542 provide additional reference points of the pressure of the gases flow passing through the outlet manifold 500 passageways. Accordingly, there are several positions in the gases flow path where the pressure can be calculated/determined. In the event any of the pressure levels of the relevant sensors exceed a predetermined threshold, the various safety valves can be activated to vent the gases flow to atmosphere or shut the gases flow off.

In an alternative embodiment, the outlet manifold 500 of the gas flow modulator 59 may include a single pressure sensor and a single flow sensor. The single pressure sensor and the single flow sensor may be used to determine the pressure of the gases flow and its flow rate.

Other pressure sensors may be provided on the manifold PCB 520. For example, a patient pressure sensor 544 may be provided on the manifold PCB 520. The patient pressure sensor 544 may be part of a patient pressure sensing circuit. The patient pressure sensing circuit may also include a patient pressure tap that is located proximal to the patient. The patient pressure tap may be in fluid communication with the patient pressure sensor 544. The patient pressure tap may be in fluid communication with the gases flow proximal to the point where the gases are delivered to the patient. In this manner, the patient pressure sensor 544 may measure the pressure of the gases flow at the point of delivery to the patient. The patient pressure sensing circuit may include a coupling tube that couples the patient pressure sensor 544 to a patient pressure port provided in the housing 320. An additional patient pressure coupling tube may be in fluid communication with the patient pressure port provided in the housing 320 and patient pressure tap. The additional coupling tube may be detachable from the housing 320. The additional coupling tube may be a single use tube that is replaced with each new patient that uses the gas flow modulator 59.

As FIG. 31 shows, a temperature reading of the gases flow may be taken in the outlet manifold 500. A temperature sensor 538 is provided for this purpose and measures the flow temperature at a location between the outlet filter/constrictor 506 and the gases outlet 330. However, the temperature sensor 538 may be located at any appropriate location along the flow path in the outlet manifold 500.

Figure 32A:
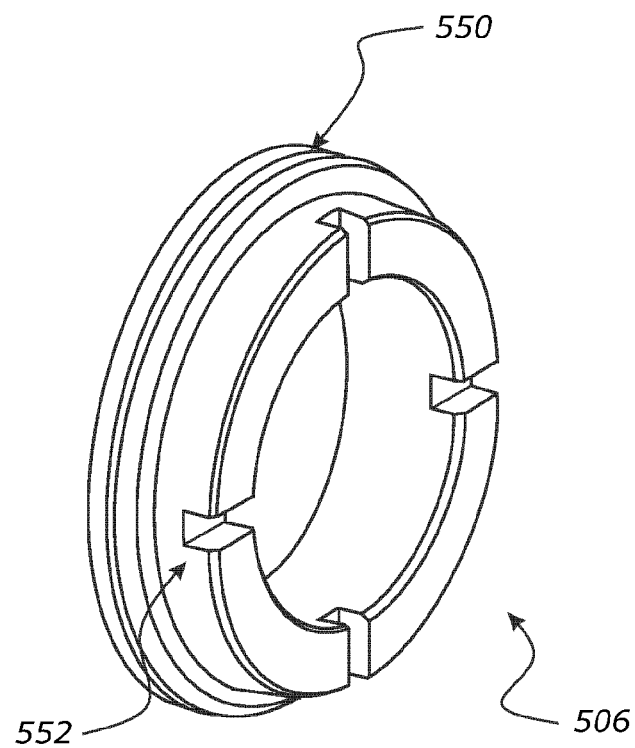
FIG. 32A is a perspective view of an embodiment of a flow constrictor that may be mounted in the outlet manifold of FIGS. 28 and 30.
Figure 32B:
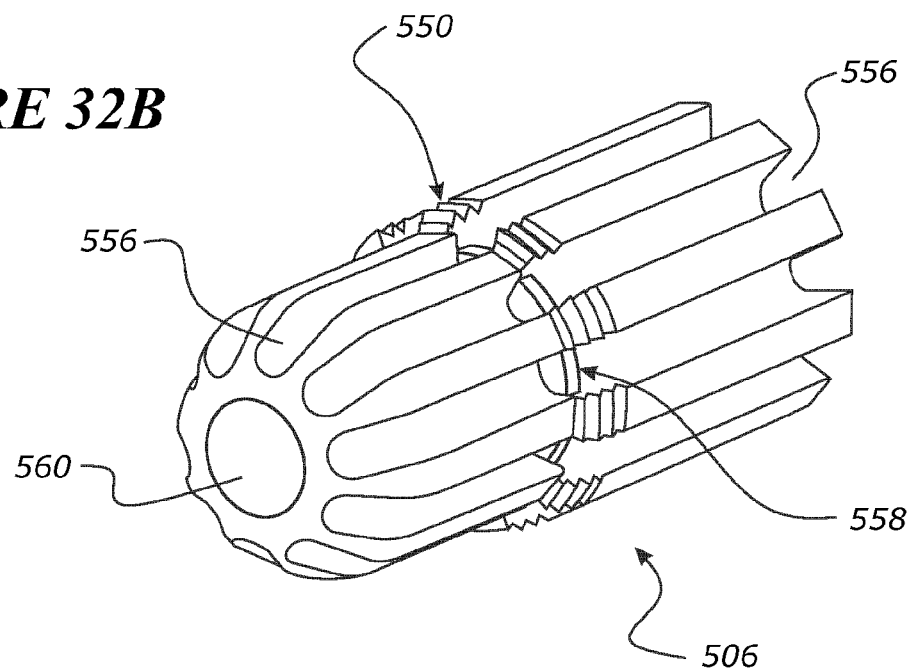
FIG. 32B is a perspective view of another embodiment of a flow constrictor that may be mounted in the outlet manifold of FIGS. 28 and 30.

Turning now to FIGS. 32A and 32B, flow constrictor 506 embodiments will now be described.

FIG. 32A shows one embodiment of the flow constrictor 506. The flow constrictor 506 takes the form of an annulus or washer shape. When installed in the manifold block 512, the flow constrictor 506 forms an orifice plate in the flow path. The orifice plate creates the necessary pressure drop in the fluid passing through the flow constrictor 506. The flow constrictor 506 may be mounted in the outlet manifold block 512 by way of a threaded fixture 550 on the circumference of the flow constrictor 506. A plurality of slots are provided on the downstream axial face of the flow constrictor 506 to allow the flow constrictor to be threaded into place in the manifold block 512.

Another embodiment of flow constrictor 506 is shown in FIG. 32B. A threaded fixture 550 is circumferentially located in the middle of the body of the flow constrictor 506. The flow constrictor 506 may be threaded into place in the manifold block 512 by way of the threaded fixture 550.

The flow constrictor 506 includes flow channels 556 that extend in the general direction of the gases flow path. The flow channels 556 are located on the outer portion of the flow constrictor's 506 body. The flow channels 556 help smooth and guide the flow through the flow constrictor 506. In the embodiment shown in FIG. 32B, the flow constrictor 506 is generally cylindrical in shape and the flow channels 556 extend in a generally axial direction. However, the flow constrictor 506 may be another suitable shape, for example, having a rectangular cross-section. Also in the embodiment show in FIG. 32B, the plurality of flow channels 556 are substantially arranged as a radial array formation around the circumference of the cylindrically shaped flow constrictor 506.

A central bore 560 is provided through the flow constrictor 506. The central bore 560 is relatively large in comparison with each of the flow channels 556. The central bore 560 provides a flow passage for majority of the flow to travel through. Thus, the flow channels 506 provide a bypass flow arrangement relative to the central bore 560.

The geometry of the flow channels 556 is also arranged to be associated with the differential pressure sensor 534 described above. Since the flow channels 506 provide the bypass flow arrangement, the pressure measurements on either side of the flow constrictor 506 can be taken by the differential pressure sensor 534 whilst only subjecting the overall gases flow through the outlet manifold 500 to a minimal pressure loss.

Moreover, the flow channels 556 help to guide some of the flow into the differential pressure sensor 534, which can then measure a pressure drop across a constriction feature located part way along each of the flow channels 556. The constriction feature is a constriction in the flow path that causes a change in pressure as the gases travel through the constriction feature.

The outer channels help to smooth the flow and reduce vortices and turbulence within the flow path upstream of the constrictor feature before the bypassed gases flow reaches the constriction feature. This helps to improve accuracy of the static pressure measurements taken across the constriction feature and, therefore, improves the accuracy of the gases flow rate reading.

The constriction feature comprises a constriction rib 558 extending circumferentially around the flow constrictor 506.

The constriction rib 558 may also be described as a constriction wall or constriction barrier. As FIG. 32B shows, the constriction rib 558 extends through each of the flow channels 556 and acts to block a portion of the flow channel 556 to gases flow. The constriction feature may also be described as comprising a constriction rib 558 provided in each of the flow channels 556. In the embodiment shown in FIG. 32B, constriction rib 558 is located immediately upstream of the threaded fixture 550, although it could be located elsewhere along the length of the flow constriction 506.

The constriction feature also comprises a stepped portion that provides a change in cross section of the flow path. The stepped portion is a diffuser. In the embodiment shown in FIG. 32B, the stepped portion is provided at least partially by the threaded fixture 550 located in the middle of the body of the flow constrictor 506. However, the stepped portion may be provided independently of the threaded fixture 550. The stepped portion could instead be located further downstream of from the middle of the body of the flow constrictor 506.

The constriction rib 558 and the stepped/diffuser portion together form the constriction feature in the flow path. Moreover, the constriction rib 558 and the stepped/diffuser portion cause a change in pressure as the gases travel through the constriction feature.

The two pressure taps of the differential pressure sensor 534 may be arranged on respective sides of the constriction feature. The two pressure taps may be arranged to be very close to the constriction feature on either side. One of the pressure taps is in fluid communication with the most proximal flow channel 556 or channels 556 upstream of the constriction feature of the flow constrictor 506. The other of the pressure taps is in fluid communication with the most proximal flow channel 556 or channels 556 downstream of the constriction feature of the flow constrictor 506. Thus, the two pressure taps of the differential pressure sensor 534 are in fluid communication with the bypassed gases flow passing through the flow channels 556. This arrangement further improves the efficiency and accuracy of static pressure measurements of the gases flow taken by the differential pressure sensor 534. Thus, the flow rate through the outlet manifold 500 gases flow path is determined in the most efficient and accurate manner.

As described above, the static pressure difference, as determined from the differential pressure sensor 534, may be correlated to a gases flow value based on a look-up table or a pressure vs flow curve.

The applicant has found that constructing an inlet 400 and outlet manifold 500 arrangement using commercially available components has worked satisfactorily. The preferred commercially available components and their relevant reference signs are set out in the table below.

| REF NUMBER | COMPONENT | SUPPLIER & PART NUMBER | MATERIAL |
|---|---|---|---|
| 229 | gases supply tube | Amvex HS-10IO0DFBMC4 | PVC, nylon, ferrous material |
| 402 | gases Inlet | Amvex BA-O-M4 | Stainless steel (SS) |
| 404 | inlet filter | Swagelok SS-4F-K4-15 | SS |
| 406 | solenoid valve | IMI 01-211P-0361H1 63111A 12 VDC/.5 W B03 Oxy | SS (AISI 430, 302), PAA, FPM |
| 408 | pressure regulator | IMI RM1H-NND-NCV | SS, Aluminium, PPS, FPM |
| 410, 502 | compression fittings | Legris 01050610 | Brass |
| 450 | gases connection flow tube | SMC 10-TU0604C-20 | PU |
| 522 | proportional valve | IMI 2.2 FlatP 16 mm 12 V 211 mA 57 | SS, Brass, FPM |
| 504 | outlet filter | TWP mesh disc | SS |
| 506 | flow constrictor | machined | SS or brass |
| 534 | differential pressure sensor | Sensirion SDP31 | Glass (Si3N4, SiO2), LCP, epoxy resins |
| 532, 540, 542, 544 | Static pressure sensors | Amphenol NPA-700 | Silicone, epoxy, RTV, pyrex |
| 514, 536 | Pressure ports | SMC barbed ports, M-3AU-4 | SS |
| 508 | pressure relief valve | IMI SPGB/38479-110 | EN AW 6082-T6 (anodised), FKM, SS (AISI-302) |
| 412, 512, 507 | inlet manifold block, outlet manifold block, filter assembly | machined | Brass, Nickel plated |
| 510 | Mesh guard | TWP mesh disc | SS |
| 404a, 407b | plugs | Legris 02051700, 020510000 | Brass |

Figure 34:
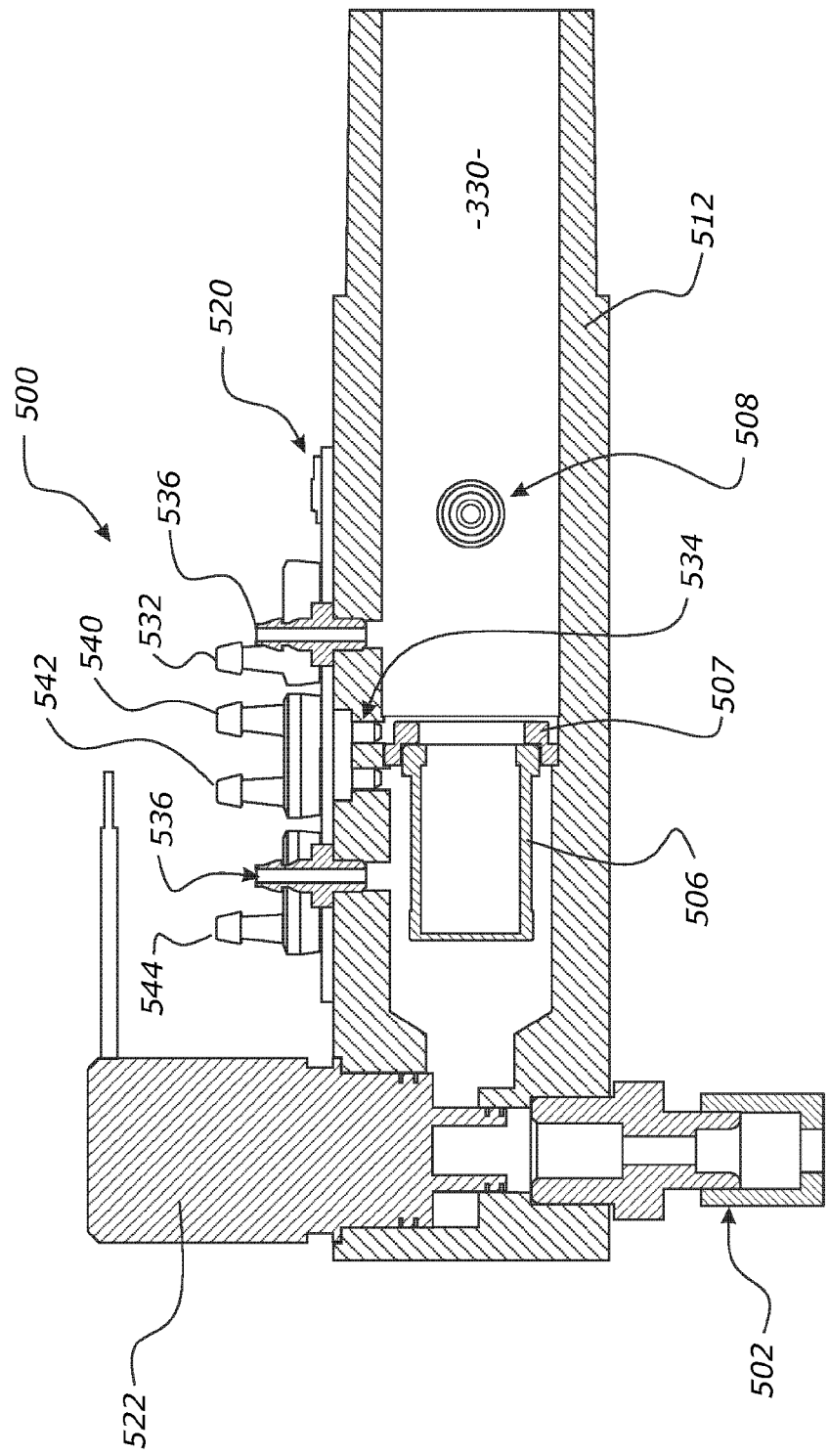
FIG. 34 shows a cross-sectional view through another embodiment of outlet manifold shown in FIG. 28.

Another embodiment of the outlet manifold 500 is shown in the cross-sectional view of FIG. 34. This outlet manifold 500 embodiment is substantially the same with the exception that the outlet filter and flow constrictor have been rearranged. In this embodiment the outlet filter and flow constrictor have been combined into a single component. The outlet manifold 500 is also schematically illustrated in FIG. 35, which is a schematic showing the flow path of gases through the inlet manifold and outlet manifolds of a gas modulator 59 including this embodiment of outlet manifold 500.

In order relative to the flow path, the outlet manifold 500 has an inlet compression fitting 502, a proportional valve 522, outlet filter/constrictor 506 and a relief valve 508. The outlet manifold 500 accommodates the gases outlet 330. Gases flow, from the gases connection flow tube 450, through each of these components in series until from the they exit the outlet manifold 500 through the gases outlet 330 into a gases delivery tube 14. The components are mounted in, or on, an outlet manifold block 512.

As with the outlet manifold 500 described above, the gases outlet 330 be a standard tapered outlet port connector adapted to couple to a patient gases delivery circuit/tube. An additional filter may be provided in the outlet manifold 500 between the inlet compression fitting 502 and the proportional valve 522. As described above, the proportional valve 522 subjects the gases flow to oscillations to provide the therapy described herein.

The gases flow leaving the proportional valve 522 passes through the outlet filter/constrictor 506, which is located in the flow path. The outlet filter/constrictor 506 is mounted in the outlet manifold block 512 on an outlet filter/constrictor housing 507. The outlet filter/constrictor housing 507 is shown in cross-sectional FIG. 34.

The outlet filter/constrictor 506 acts to smooth the gases flow. The outlet filter/constrictor 506 acts to protect the proportional valve from particles that may fly into the proportional valve 522 when gases are being drawn back into the gas flow modulator 59. Particulate matter may be drawn back into the gas flow modulator 59 due to pressure differentials. The outlet filter/constrictor 506 may be a sintered filter. The outlet filter/constrictor 506 may have a 40 µm pore size. The outlet filter/constrictor 506 may have a 15 µm pore size. The outlet filter/constrictor 506 may have a single layer of filter material or multiple layers of filter material.

The pressure relief valve 508 is positioned downstream of the outlet filter/constrictor 506 and adjacent to the gases outlet 330. The pressure relief valve 508 is substantially the same and performs the same safety functionality as for the embodiment of outlet manifold 500 described above.

As with the embodiment described with respect to FIGS. 28 and 30, a manifold PCB 520 is mounted to the manifold block 512. Again pressure sensors 532, 540, 542 and 544 are mounted on the manifold PCB 520. They may perform the same functions as described earlier herein.

Again, as with the embodiment described with respect to FIGS. 28 and 30, a differential pressure sensor 534 may also be provided mounted on the outlet manifold block 512. The differential pressure sensor 534 functions in a similar way to the embodiment described above except that pressure measurements are performed upstream and downstream of the outlet filter/constrictor 506.

The differential pressure sensor 534 consists of two pressure taps, which are in fluid communication with the outlet flow passageway. One of the pressure taps is in fluid communication with the passageway upstream of the outlet filter/constrictor 506. The other of the pressure taps is in fluid communication with the passageway downstream of the outlet filter/constrictor 506. The static pressure of the gases flow both upstream and downstream of the outlet filter/constrictor 506 can be measured by the differential pressure sensor 534 and the flow rate of the gases flow can be determined/inferred using a look-up table or a pressure vs flow curve.

Figure 35:
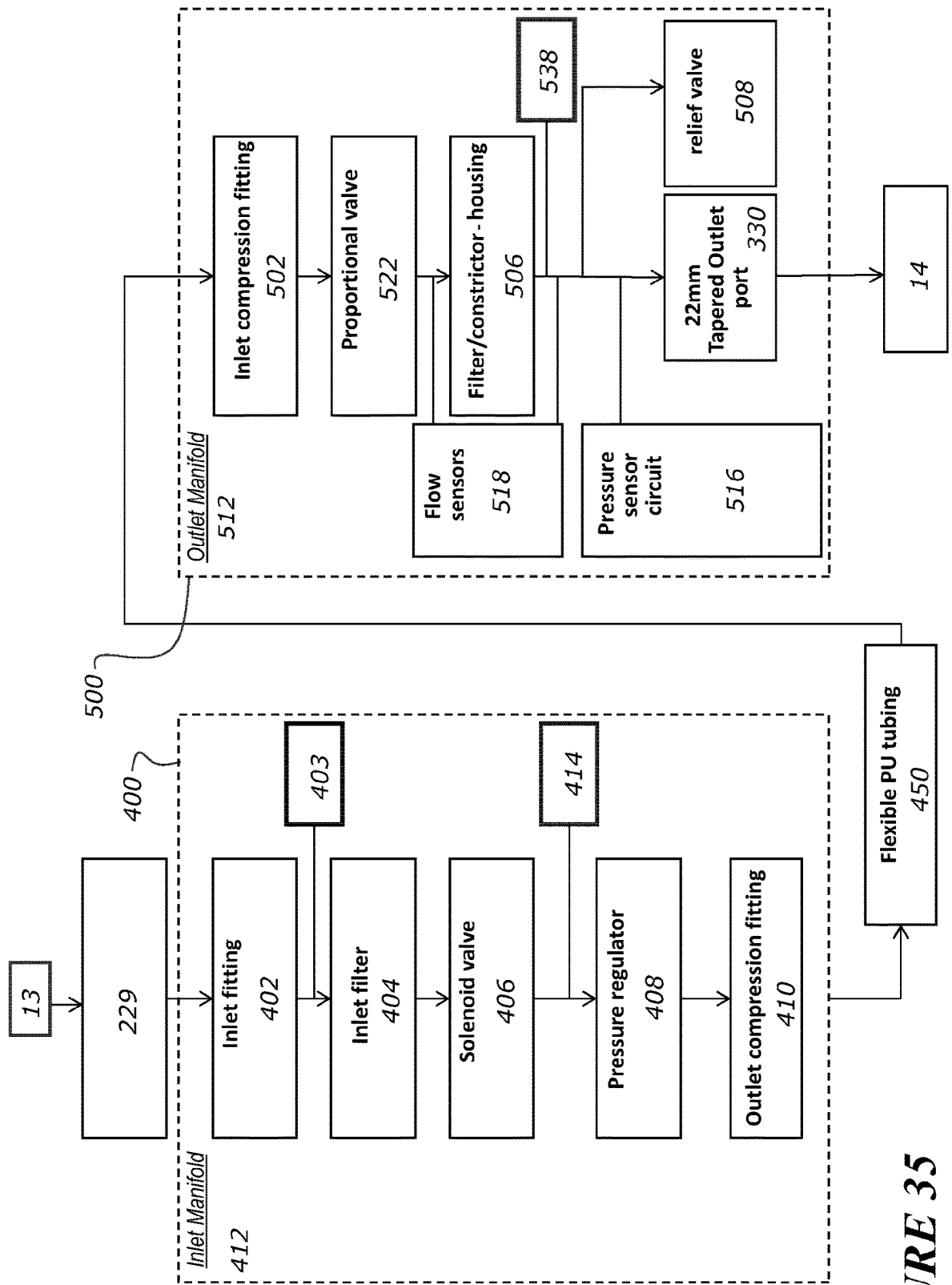
FIG. 35 is a schematic showing of the flow path of gases through the inlet manifold and an outlet manifold of FIG. 34.

This arrangement is shown schematically in FIG. 35, in which flow sensors 518 indicate the position of the pressure taps/measurements. Schematically, the measurements may be taken between the proportional valve 522 and the outlet filter/constrictor housing 506 and also between the outlet filter/constrictor housing 56 and the gas outlet 330. The flow sensors 518 may be used to determine the flow across the outlet filter/constrictor housing 506 and, therefore, through the gas flow modulator 59. Furthermore, the flow sensor 518 information may be used to display the flow rate being delivered to the patient on the input output interface 339. Alternatively, the flow sensor 518 information may be used by the controller to further control relief valve 508 if the flow is above a particular threshold.

As FIG. 35 shows, a temperature reading of the gases flow may be taken in the outlet manifold 500. A temperature sensor 538 is provided for this purpose and measures the flow temperature at a location between the outlet filter/constrictor 506 and the gases outlet 330. However, the temperature sensor 538 may be located at any appropriate location along the flow path in the outlet manifold 500.

The preferred construction, using commercially available components, for the gas flow modulator using this embodiment of outlet manifold 500 is set out in the table below.

| REF NUMBER | COMPONENT | SUPPLIER & PART NUMBER | MATERIAL |
|---|---|---|---|
| 229 | gases supply tube | Amvex HS-10IO0DFBMC4 | PVC, nylon, ferrous material |
| 402 | gases Inlet | Amvex BA-O-M4 | Stainless steel (SS) |
| 404 | inlet filter | Swagelok SS-4F-K4-15 | SS |
| 406 | solenoid valve | IMI 01-211P-0361H1 63111A 12 VDC/.5 W B03 Oxy | SS (AISI 430, 302), PAA, FPM |
| 408 | pressure regulator | IMI RM1H-NND-NCV | SS, Aluminium, PPS, FPM |
| 410, 502 | compression fittings | Legris 01050610 | Brass |
| 450 | gases connection flow tube | SMC 10-TU0604C-20 | PU |
| 522 | proportional valve | IMI 2.2 FlatP 16 mm 12 V 211 mA 57 | SS, Brass, FPM |
| 506 | outlet filter/constrictor | Swagelok SS-4F-K4-40 | SS |
| 534 | differential pressure sensor | Sensirion SDP31 | Glass (Si3N4, SiO2), LCP, epoxy resins |
| 532, 540, 542, 544 | Static pressure sensors | Amphenol NPA-700 | Silicone, epoxy, RTV, pyrex |
| 514, 536 | Pressure ports | SMC barbed ports, M-3AU-4 | SS |
| 508 | pressure relief valve | IMI SPGB/38479-110 | EN AW 6082-T6 (anodised), FKM, SS (AISI-302) |
| 412, 512, 507 | inlet manifold block, outlet manifold block, filter housing | machined | Brass, Nickel plated |
| 404a, 407b | plugs | Legris 02051700, 020510000 | Brass |

In an alternative embodiment, the gas flow modulator 59 may receive multiple gas supplies via multiple respective gas supply tubes fluidly connected to multiple respective inlets. For example, the gas flow modulator may receive an oxygen gas supply and an air gas supply—whereby the respective gas supplies may mix within the gas flow modulator. As noted earlier, in an alternative embodiment, the gas flow modulator 59 might receive multiple gas supplies via multiple respective inlets. For example, the gas flow modulator might receive an oxygen gas supply and an air gas supply. In such an embodiment, the respective gas supplies may mix within the oscillator unit and the proportion of the gas mixture controlled by respective proportional valves.

In some embodiments, the gas flow modulator 59 may include additional inlet valve arrangements. The additional valve arrangements may be located in an inlet sub-manifold of the flow manifold. Such arrangements may include a plurality of sub-manifolds. For example, two sub-manifolds may be provided as described above, one of which is the inlet sub-manifold.

The additional valve arrangements allow the concentration of the oxygen ($O_2$) delivered to the patient to be controlled. The valve arrangements control the concentration of oxygen ($O_2$) in an air/oxygen mixture. Further still, the additional valve arrangements allow control of the oscillations delivered to the patient.

The percentage of oxygen can be controlled based on the state of the patient. For example, if the patient is apnoeic a larger proportion of oxygen may be delivered in comparison with a situation where the patient is spontaneously breathing.

Figure 36:
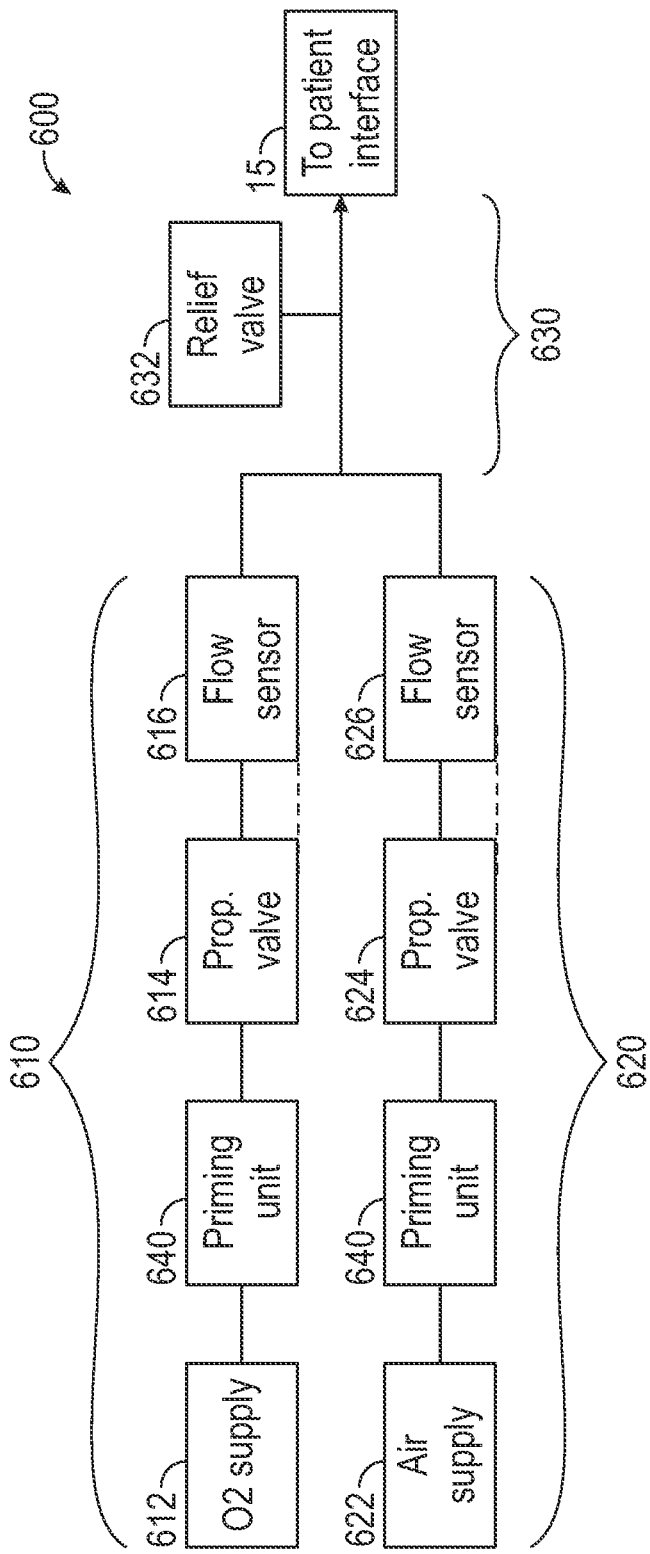
FIG. 36 schematically shows an inlet valve arrangement for another embodiment of the gas flow modulator 59.

FIG. 36 schematically shows one inlet valve arrangement 600 for an embodiment of the gas flow modulator 59.

The inlet valve arrangement 600 includes two inlet lines. An oxygen inlet line 610 supplies oxygen to a combined pipe 630 or mixing chamber. An air inlet line 620 supplies air to the combined pipe 630 or mixing chamber. An inlet 612 is provided for oxygen supply on the oxygen inlet line 610. An inlet 622 is provided for air supply on the air inlet line 620. The two inlet lines may be included in the inlet manifold.

The oxygen inlet line 610 and the air inlet line 620 each include a respective proportional valve 614, 624. The proportional valves 614, 624 operate to control the amount of air/oxygen that is delivered into a combined pipe or a mixing chamber. The combined pipe or mixing chamber may be included in the inlet manifold.

The inlet valve arrangement 600 can also be used to create oscillations by controlling the proportional valves 614, 624 the individual inlet lines. A flow sensor 616 is provided on the oxygen inlet line 610. A flow sensor 626 also is provided on the air inlet line 620. The flow sensors 616, 626 provide feedback control, indicated by the dashed lines in FIG. 36, to the proportional valves 614, 624 to maintain the concentration of oxygen in the air/oxygen mixture.

The proportional valves 614, 624 may also include feedback from a pressure sensor. The proportional valves 614, 624 may include additional control lines from a controller to control the opening and closing of the proportional valves 614, 624 based on an oscillation signal. In this manner the proportional valves 614, 624 may create an oscillating oxygen flow and an oscillating air flow. The oscillating oxygen flow and an oscillating air flow may later mix and pass along the gases flow path through the gas flow modulator 59 to ultimately be delivered to the patient interface 15. The mixed gases flow from the inlet valve arrangement 600 may flow through the inlet manifold and an outlet manifold of the gas flow modulator, as described above.

A relief valve 632 may be provided in the combined pipe 630 or mixing chamber. In the event that the pressure of the gases flow in the combined pipe 630 exceeds a predetermined threshold, then the relief valve 632 may be activated and vent the gases flow to atmosphere. The relief valve 632 is a safety feature provided in the inlet valve arrangement 600 to prevent excess gases pressure build up in the gases flow path of the inlet valve arrangement 600. The relief valve 632 may be entirely independent of the other safety valves and features provided in the gas flow modulator 59. The relief valve 632 may act in concert with the other safety valves and features provided in the gas flow modulator 59. The relief valve 632 maybe a mechanically operated relief valve. The relief valve 632 may be an electrically operated relief valve that operates under the direction of a controller.

Figure 36A:
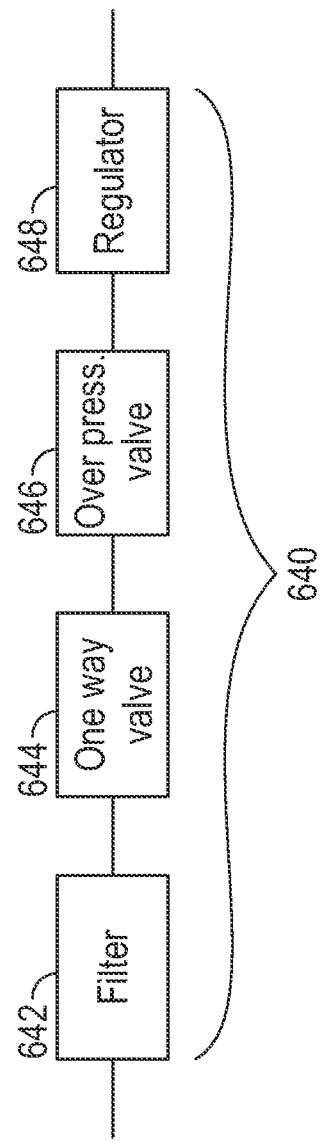
FIG. 36A schematically shows a priming unit of the inlet valve.

Each of the oxygen inlet line 610 and the air inlet line 620 may include a priming unit 640. The priming unit is shown in FIG. 36A. The priming unit 640 may include a filter 642. The filter 642 may be a mesh filter. The priming unit 640 may include a one-way valve 644. The priming unit 640 may include an over-pressure valve 646. The priming unit 640 may include a regulator 648. The regulator 648 may be a flow regulator. The regulator 648 may be a pressure regulator.

The priming unit 640 may include all of, some of, or only one of the components described above and shown in FIG. 36A.

Figure 37:
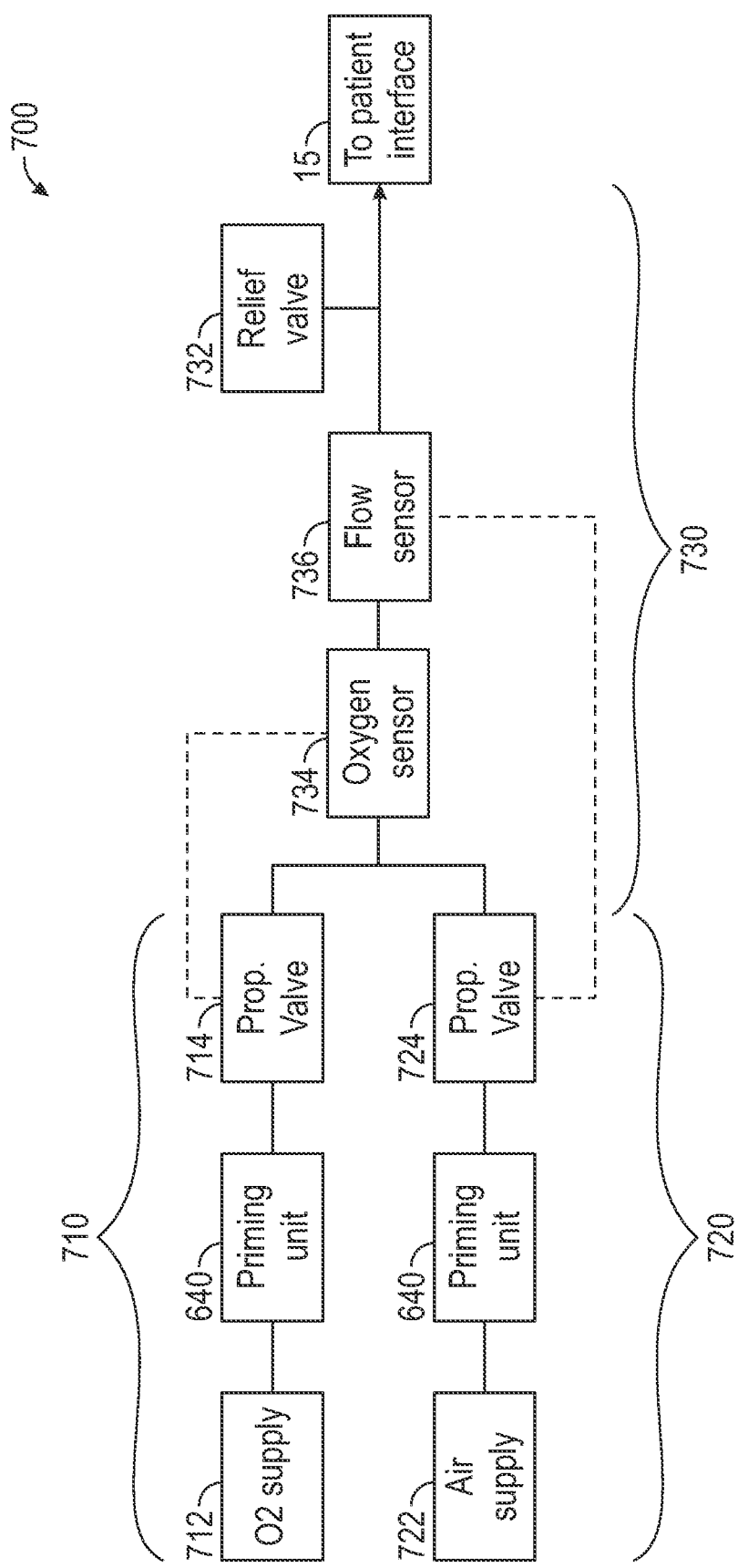
FIG. 37 schematically shows another inlet valve arrangement for another embodiment of the gas flow modulator 59.

FIG. 37 schematically shows another inlet valve arrangement 700 for an embodiment of the gas flow modulator 59.

The inlet valve arrangement 700 is arranged to control the concentration of oxygen. The inlet valve arrangement 700 includes an oxygen inlet line 710 with an inlet 712 and an air inlet line 720 with an inlet 722. The oxygen and air from the two inlet lines are mixed in a combined pipe 730. The two inlet lines and combined pipe 730 may be included in the inlet manifold.

The oxygen inlet line 710 and the air inlet line 720 each include a respective proportional valve 714, 724. The proportional valve 714 of the oxygen inlet line 710 is controlled based on an oxygen sensor 734 that measures the concentration of oxygen. The proportional valve 724 of the air inlet line 720 is controlled based on a flow sensor 736. The proportional valve 724 controls the air supplied thought the air inlet line 720 based on a signal from the flow sensor 736. The signal from the flow sensor 736 is processed by a controller to ensure that a required flow rate is delivered.

Again, either one of the proportional valves 714, 724 may also be controlled to create oscillations in the flow. The percentage of oxygen can be controlled based on the state of the patient, for example, if the patient is apnoeic a larger proportion of oxygen may be delivered to the patient.

As with the inlet valve arrangement 600 above, each of the oxygen inlet line 710 and the air inlet line 720 of the inlet valve arrangement 700 may include a priming unit 640 as shown in FIG. 36A. The priming unit 640 may include all of, some of, or only one of the components described above and shown in FIG. 36A.

Also as with the inlet valve arrangement 600 above, a relief valve 732 may be provided in the combined pipe 730 or mixing chamber.

Figure 38:
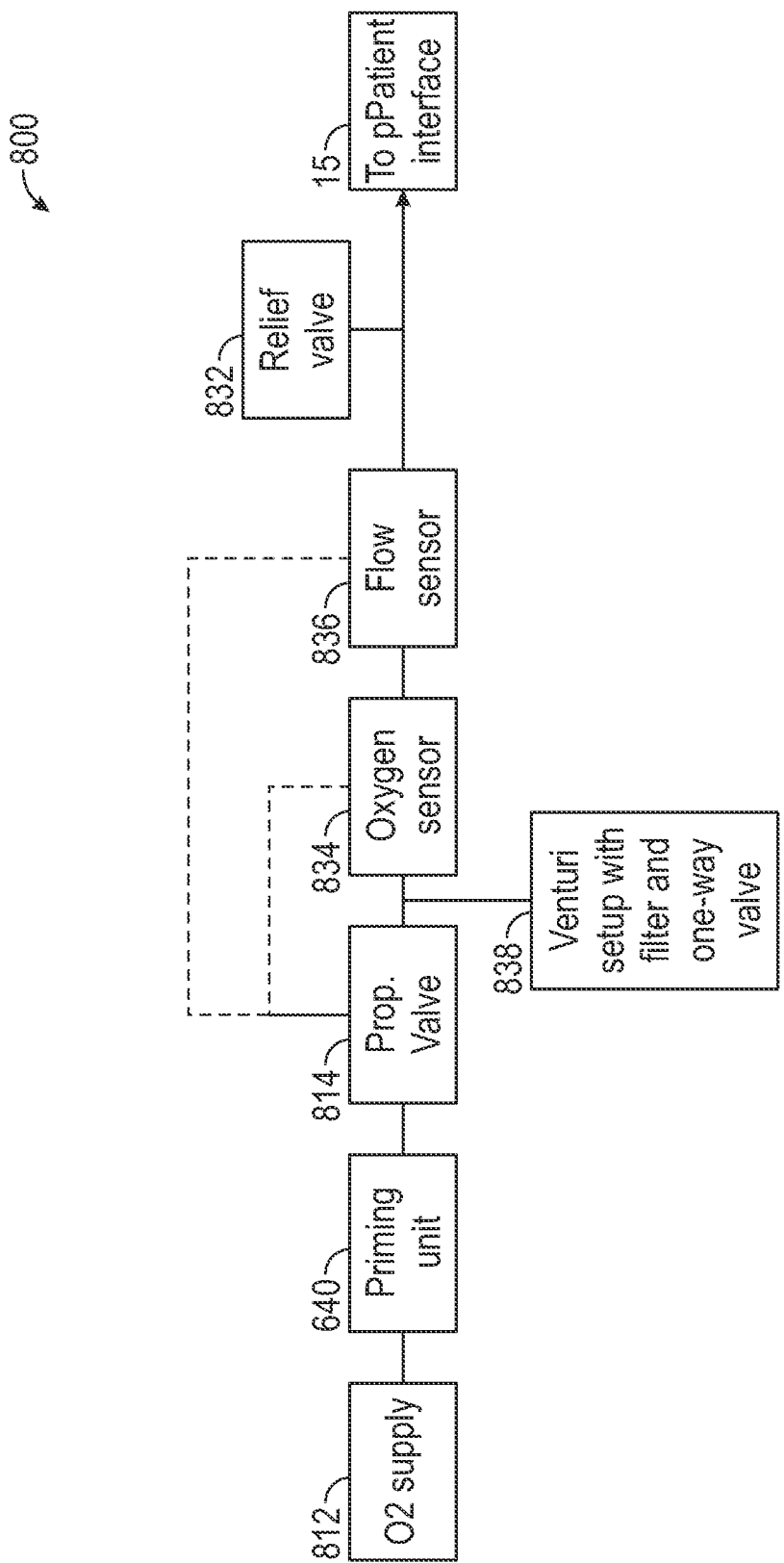
FIG. 38 schematically shows another inlet valve arrangement for another embodiment of the gas flow modulator 59.

FIG. 38 schematically shows another inlet valve arrangement 800 for an embodiment of the gas flow modulator 59.

The inlet valve arrangement 800 is an oxygen inlet line with a proportional valve 814. The oxygen inlet line may be included in the inlet manifold.

The proportional valve 814 may be controlled based on an oxygen sensor 834 and a flow sensor 836.

The inlet valve arrangement 800 also includes a venturi arrangement 838. The venturi arrangement 838 may include a filter. The venturi arrangement 838 may include a one-way valve. The venturi arrangement 838 draws in additional air as the flow rate of oxygen increases. In this manner, the venturi arrangement 838 increases the overall mass flow and reduces/controls the concentration of oxygen in an air/oxygen mixture delivered to the patient through the patient interface 15. In other words, the venturi arrangement 838 acts as a passive air flow controller.

As with the inlet valve arrangement 600 above, the oxygen inlet line of the inlet valve arrangement 800 may include a priming unit 640 as shown in FIG. 36A. The priming unit 640 may include all of, some of, or only one of the components described above and shown in FIG. 36A. A relief valve 832 may also be provided in the combined pipe 730 or mixing chamber In an alternative embodiment, a blower 3 may be included as a part of the gas flow modulator.

It should be appreciated that the gas flow modulator and the humidifier 17 could be positioned interchangeably in the flow path.

In an alternative embodiment, the gas flow modulator and humidifier 17 form a single unit.

In an alternative configuration, the humidifier is excluded and the outlet tube conveys [non-humidified] gas directly to the patient interface.

An outlet filter 240 can be provided in the flow path between the oscillator unit and the patient interface.

An inlet filter 241 may optionally be provided adjacent the inlet to prevent ingress of any contaminants, debris or particulates into the flow path and, more specifically, from reaching the patient. As noted earlier, an external/outlet filter 240 may be provided downstream of the oscillator unit adjacent to the patient interface. As such, in an alternative embodiment, the inlet filter may be excluded and the outlet filter relied on to prevent contaminants, debris or particulates from reaching the patient.

In other embodiments, multiple gas flow modulators 59 could be placed and different points in the system as previously described.

As noted earlier, the present inventors have determined that by oscillating the flow (as described herein) in the trachea in a patient who is not breathing spontaneously gas is driven down the trachea to the lungs, and then back up from the lungs to the trachea—that is, it provides a mechanism for transporting gas in and out of the lungs.

In another example, the system 10 (for example, like any of those shown in FIG. 1, 1C, 4, 6 or 7) is configured to provide a varying gas flow (with a varying waveform) with a base flow component and a plurality oscillating gas flow components, the oscillating flow components having frequencies corresponding to heart activity, chest cavity (or other body cavity) resonant frequency and a frequency to assist airway mixing. In this embodiment, the varying gas flow has a varying gas flow rate, with a base flow rate component and a oscillating flow rate component corresponding to heart activity, and oscillating flow rate component corresponding to chest cavity resonance, and an oscillating flow rate component corresponding to a frequency that is determined to assist with mixing in combination with the other oscillating flow rate frequencies. The respective frequencies of the oscillating components corresponding to the heart activity and the chest cavity resonance can be determined as described previously above. It has been determined that providing the combination/some of these oscillating flow rate frequencies provides more effective $CO_2$ removal and/or oxygenation than using a single frequency corresponding to a single physiological parameter alone.

The body cavity resonance value or the chest cavity resonance value may be based on the resonance value of an average human. The body cavity resonance value or the chest cavity resonance value may be based on the resonance value of an average male and of an average female. The body cavity resonance value or the chest cavity resonance value may be hard coded or stored in memory and, in use, can be accessed by the controller to introduce a corresponding frequency component.

In a further alternative, a cavity resonance, for example a chest cavity resonance, may be determined by a clinician or other suitable person for each patient and may be programmed and stored in memory for access by the controller to control the valve.

Figure 19:
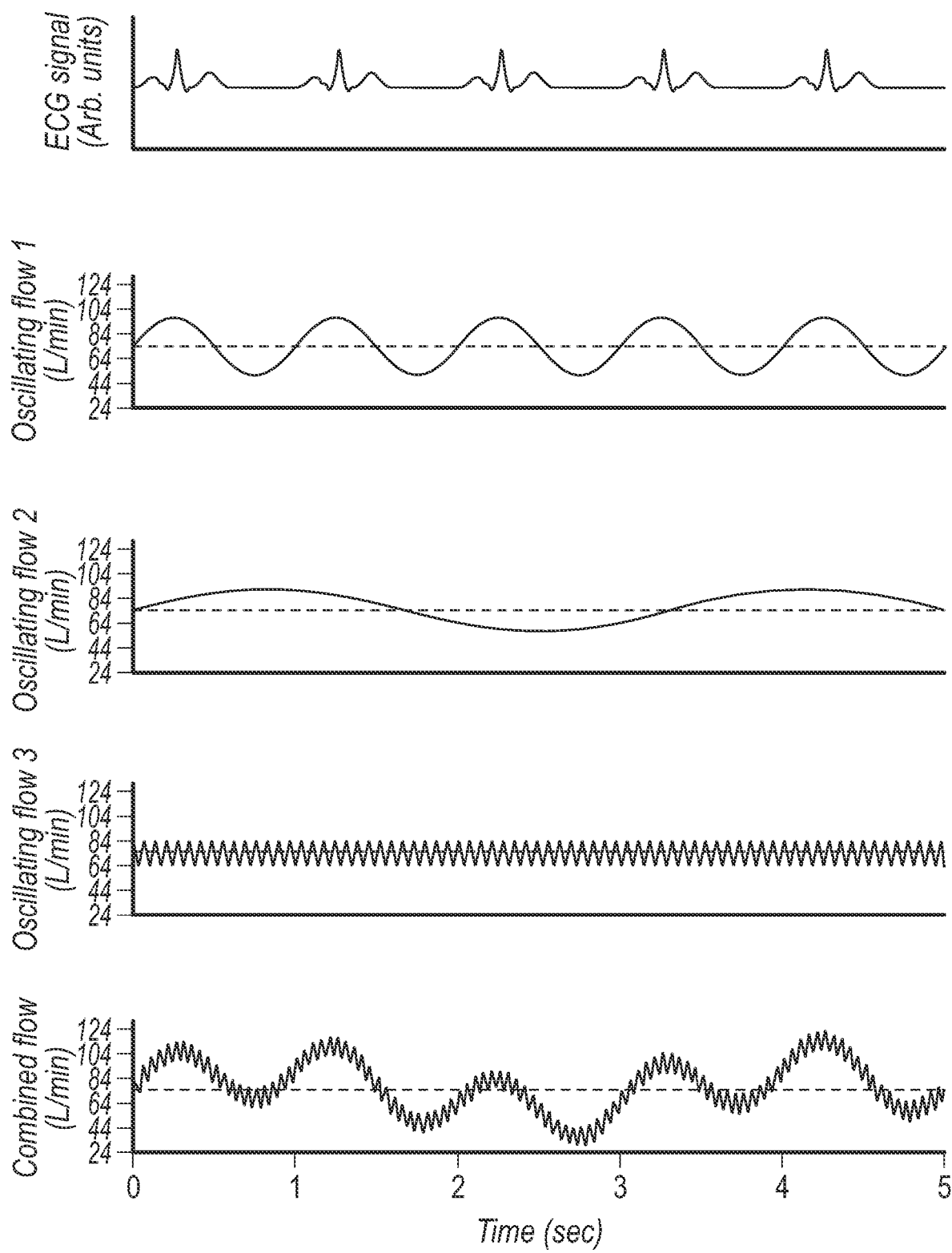
FIG. 19 shows waveform with multiple oscillating components with frequencies based on heart activity and body cavity resonance, and also a mixing frequency.

Referring to FIG. 19 the varying gas flow has a varying gas flow rate comprising:
- a base flow rate component with a flow rate of about as previously described;
- a first (heart activity) oscillating flow rate component as previously described at a frequency of about 0.1 Hz to about 3 Hz;
- an experimentally determined bulk movement oscillating flow rate component with a flow rate as previously described and at a frequency of about 0.05 Hz to about 5 Hz—this could be a body cavity (e.g. lung/chest) resonance frequency and preferably lower than the heart activity frequency.
- an experimentally determined mixing turbulence oscillating flow rate component with a flow rate as previously described at a frequency of about 3.5 Hz to about 150 Hz—preferably higher than the heart activity frequency. This causes local mix or turbulence or may cause one or more body parts to resonate at those frequencies.

These flow rate components together to define the overall varying gas flow shown as a varying waveform in FIG. 19. It should be noted that the varying gas is not generated by summing together multiple gas flows. Rather, it is generated by modulating a gas flow as previously described. But, that gas flow can be described as having multiple summed flow rate components. The components above produce an overall waveform with a period of oscillation of about 0.3 s to 15 s. Its flow rate can vary from about 5 litres/min to 250 litres/min. The overall waveform can be applied intermittently in the form of a PWM waveform The combination of frequencies works best because of all the additional movement and agitation that occurs. The desire is to promote bulk movement since apneic patients do not spontaneously breathe. The heart activity frequency enhances cardiogenic oscillation and $CO_2$ being expelled from lungs. The high frequency causes local turbulence and mixing and helps in movement of gases along airwaves. The combination helps to achieve all of these and generally, more movement of the gases within the lungs and airways of an apneic patient. The mixing frequency causes turbulence in the chest cavity and airways of the patient. The high frequency can cause local eddies or turbulent flows within the airways of the patient. The airways agitate the air within the airways and cause movement. There may be several local eddies or turbulent areas within the airways that cause mixing and movement of the gases from the lungs outward and O2 from the flow into the lungs.

2.5 Experimental Results Demonstrating Benefits of Varying Gas Flow

The following experimental discussion demonstrates this.

2.5.1 Experimental Apparatus

A benchtop experimental model was used to investigate the effects of oscillating high nasal flow (HNF) on gas exchange and carbon dioxide ($CO_2$) clearance during apnoea. The model is a suitable representation of the embodiments of the apparatus 10 described herein and is shown in FIGS. 10A, 10B.

The model consisted of an adult upper airway geometry connected to a lung reservoir with compliance similar to that of the lung-chest wall system in real physiology (approximately 45 ml/cmH2O). It included the nasal and pharyngeal cavity, an open mouth, trachea, and primary and secondary bifurcations up to the sixth generation. The lung reservoir was plumbed with various controllers and sensors to introduce/monitor percent concentration of CO2 in the lung, measure the incoming flows, and monitor the static lung pressure.

In addition, a cardiogenic pump was used to simulate the effects of the heart on gas motion in the airways. It is thought that the pulsatile nature of blood flow (caused by effects of the heart) causes miniscule squeezing of the lower airways which in turn drives a plug of gas in the upper airways and trachea. The pump consisted of a numerically controlled stepper motor-syringe system and oscillated a known volume of gas at a specific wave shape and frequency into the lung reservoir. Cardiogenic oscillations can be approximated with a trapezoidal waveform of with amplitudes (stroke volume) of 5-30 mL and frequency of 0.5-3 Hz. The cardiogenic parameters (waveform, frequency, and stroke volume) will vary between patients and within the same patient at different times due to the variability in heart rate and blood pressure. FIG. 9 shows an example of a piecewise linearly approximated cardiogenic waveform with parameters derived from one experimental realisation. The fit was based on a heart rate of 64.2 bpm, stroke volume of 22.5 mL, and rise and delay fractions of 0.7 and 0.15 respectively. FIG. 9 also includes plots of shifted sinusoidal waves which illustrate (but not to scale) the phase shifting in the varying high gas flow and that will be discussed in example 3 (note that positive values imply gas pushing into the lungs).

Figure 10A:
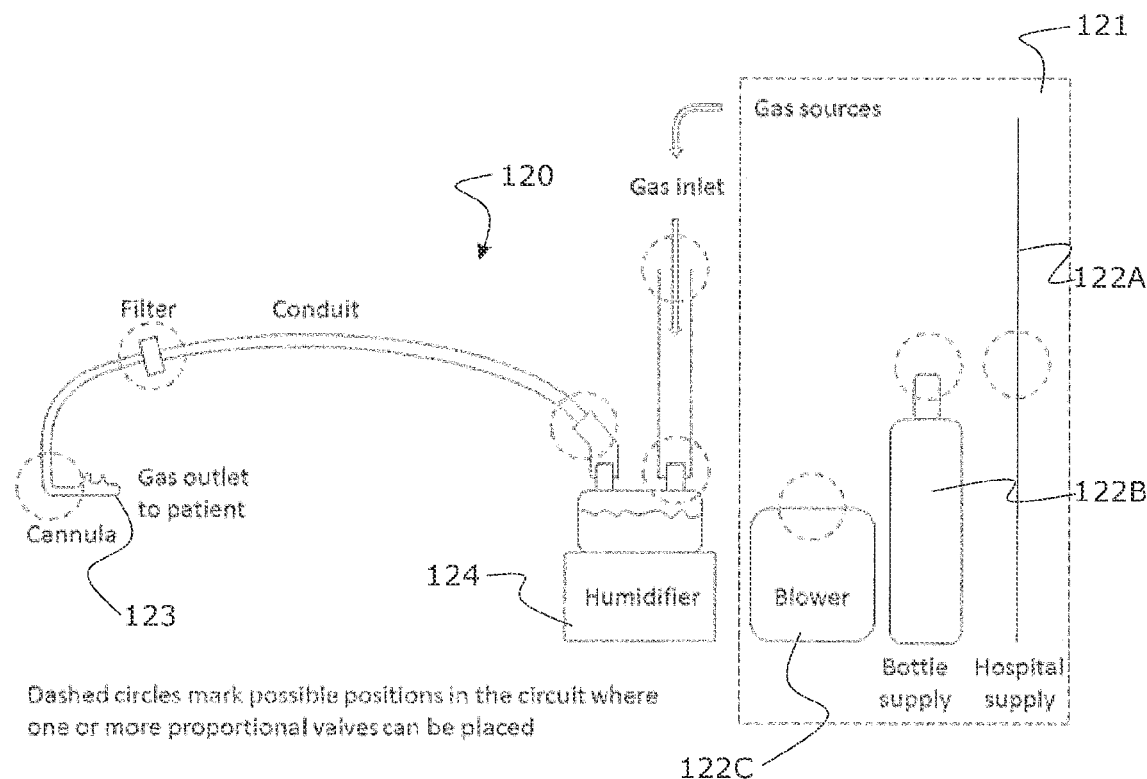
FIGS. 10A and 10B show an experimental apparatus.
Figure 10B:
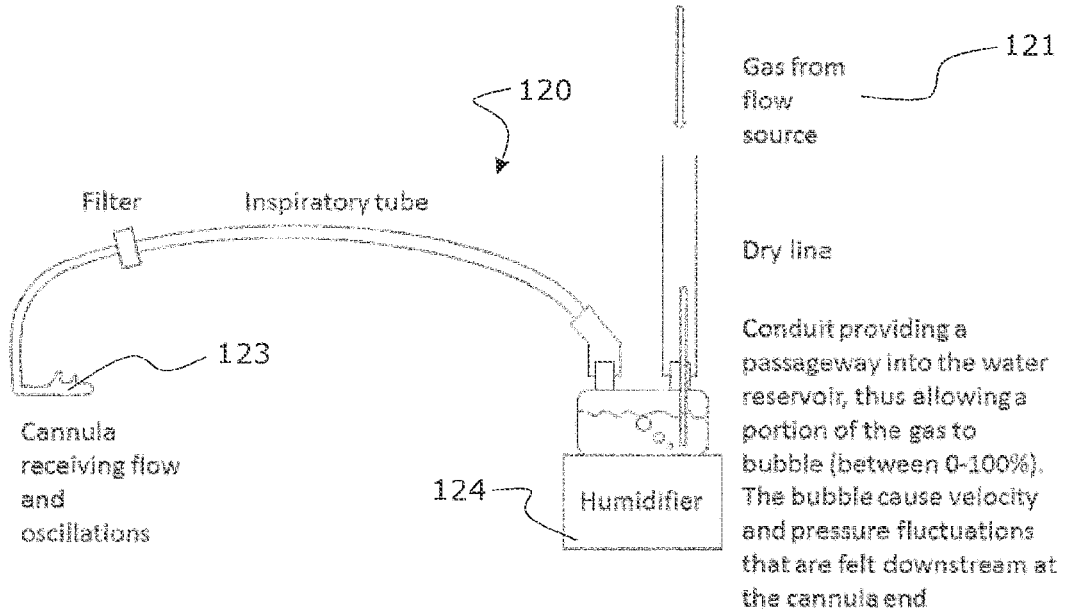
Figure 11:
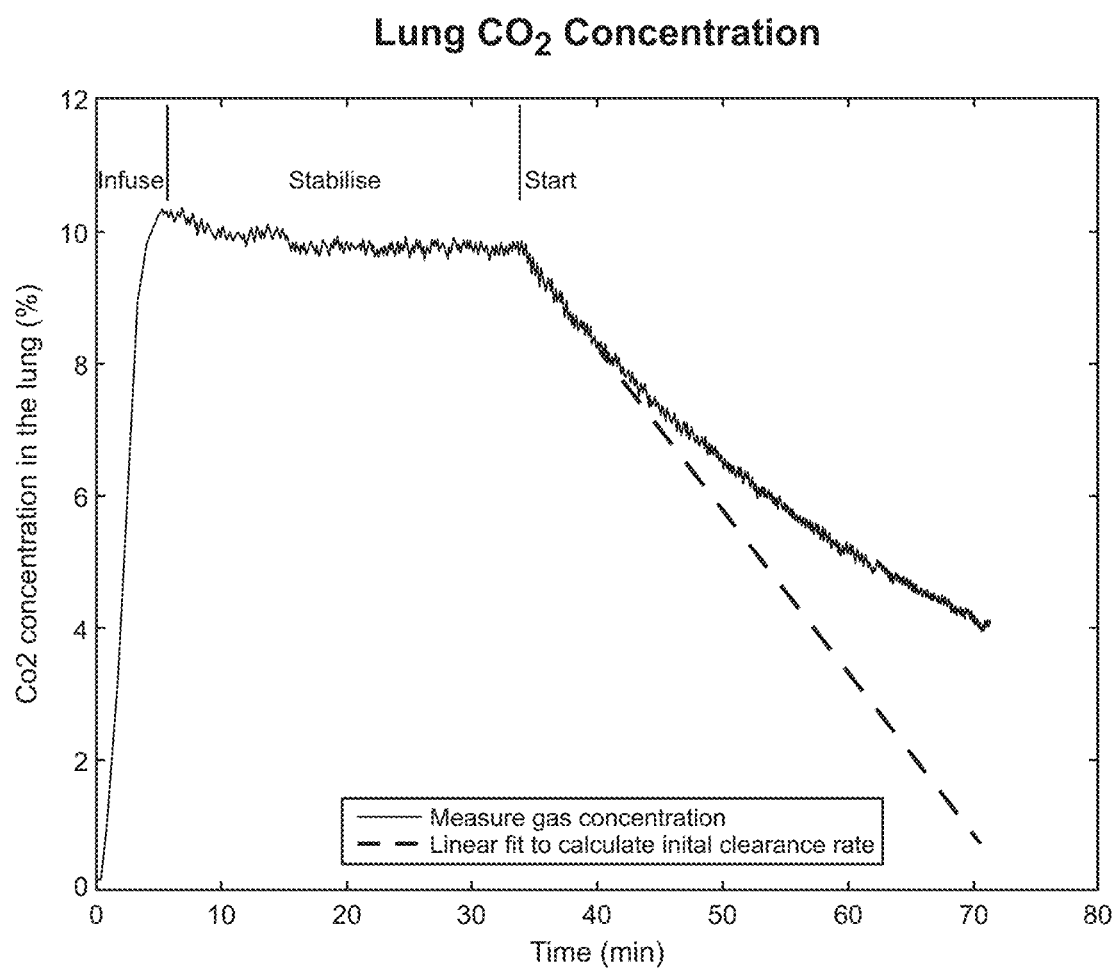
FIG. 11 shows CO2 concentration in the lung during therapy during experimental example #1.

Referring to the experimental apparatus 120 in FIG. 10A (which is a suitable model for the apparatus 10 of embodiments described herein), gas flow oscillations were delivered using a flow source 121 from a wall supply 122A, bottle supply 122B and/or blower 122C) to the nasal cavity using a high flow nasal cannula which was connected in series to a regulator and a proportional valve. The latter is an electronically controlled orifice-type valve with sufficient resolution to produce arbitrary waveforms composed of multiple frequencies. In clinical practise one or more valves could be positioned near the gas source (wall, bottle, or blower) with or without a regulator/pressure relief in series; prior or post the humidifier 124 and/or the control system; and prior or post the end of the delivery circuit but before the cannula 123 (see FIG. 10A). There are certain advantages of placing the valve in such locations. For example, valves near the gas source or inlet could shut-off or divert the flow in case of medical emergencies or when excess pressures are sensed at the patient end. Placing the valves near the humidifier/controller simplifies device integration with the rest of the system. Placing the valve in close proximity to the cannula minimises the dissipations of high frequency flow oscillations in the patient's circuit due to the compliant nature of respiratory conduits.

The method for flow oscillations is not limited to electronic proportional valves as other devices such as diaphragms, flow choppers; mechanical flutters or pressure relief valves can also be used. For example, FIG. 10B illustrates the use of an underwater pressure relief system to generate broad spectrum of oscillations that are dictated by the number, calibre, orientation, and depth of the immersed tube. The flow rate, cross section of the tube orifice and the surface tension of the liquid could also impact the nature of oscillations. This oscillation mechanism differs from the bubble CPAP as the flow fluctuations occur upstream of the patient end.

The experimental procedure consisted of applying a fixed concentration of CO2 into the lungs (at about 9.5-10%), allowing the system to stabilise, then applying the high gas flow therapy (nasal high flow therapy—NHF) and monitoring the decay of CO2 with time from the lungs reservoir. A sample of the results is shown in FIG. 1 and includes the CO2 infusion, stabilisation period and the decay of CO2 concentration in the lung after commencement of therapy. The gradient of the dotted line signifies the decay rate.

Aside from its clinical relevance, the CO2 decay rate was used in the examples below because it is a direct measure of gas exchange between the lungs and the outside environment. In these experiments, dry air was used as the incoming high flow gas mixture but it should be noted that other gases or gaseous mixtures (such as pure oxygen saturated with water vapour at 37 degrees, mixtures of O2, N2, and helium) are also possible. The initial clearance rate was calculated as the gradient of the concentration-time curve for the first five minutes of therapy and multiplied by the lung volume to obtain gas exchange data in millilitres per minute. The data in the following examples have been normalised to that without oscillations to calculate the enhancement factor.

In one example, a vibrating mesh nebuliser was connected to the upper airway model, about 5 cm above the carina and produced a mist of water (mean particle size <4 um) to allow for flow visualisation. The gas motion was simultaneously captured with a high speed camera at 900 fps and later analysed using image processing software (ImageJ, and Matlab) to estimate time of flight and bulk gas velocity.

The following examples illustrate how varying the flow rate promotes gas exchange in the lungs, the presence of a useful frequency range where CO2 clearance is enhanced, the advantages of syncing the NHF waveform with the heart signal, the advantages of combining multiple frequencies, and the advantages of varying the wave shape. Note, the examples should not be considered exhaustive of the nature of the oscillating gas flows that will be effective and clearing CO2. Rather, they demonstrate non-limiting particular examples of the benefits of oscillating gas flows. Gas flow oscillations with parameters and parameter values (e.g. frequency, phase, amplitude and the like) other than those tested will also be effective at clearing CO2.

2.5.2 Example #1

Figure 12:
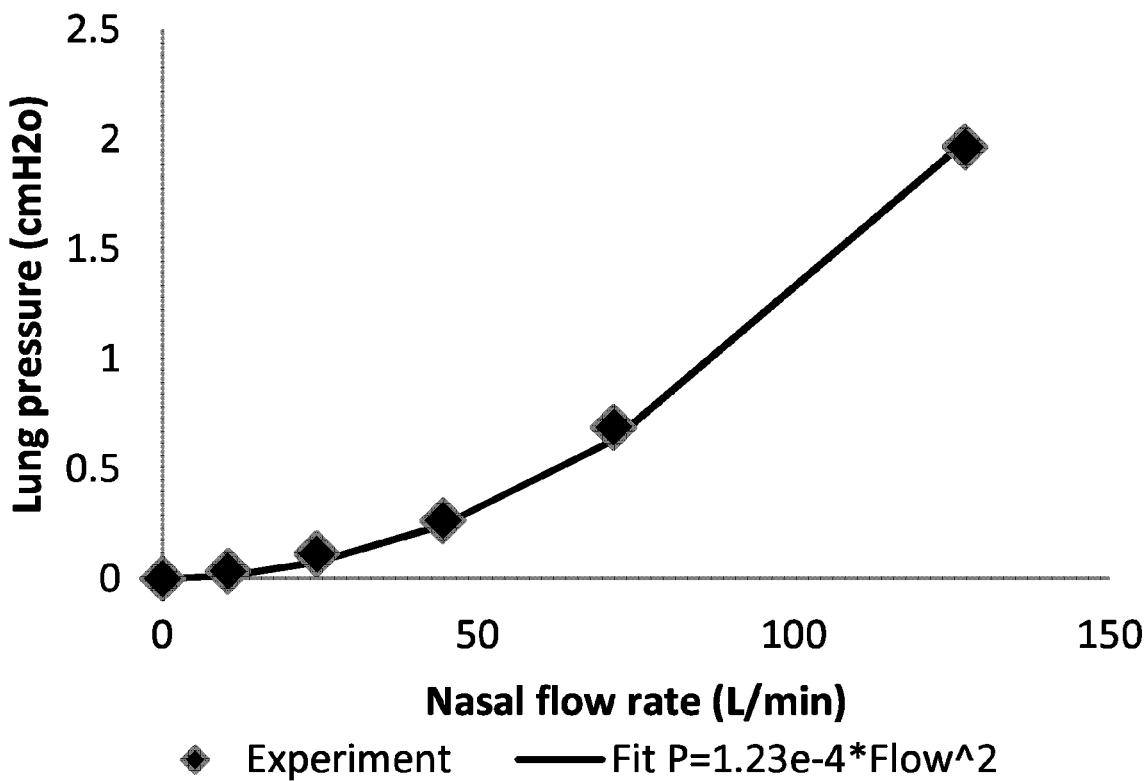
FIGS. 12 and 13A show lung pressure and flow rate during experimental example #1.
Figure 13A:
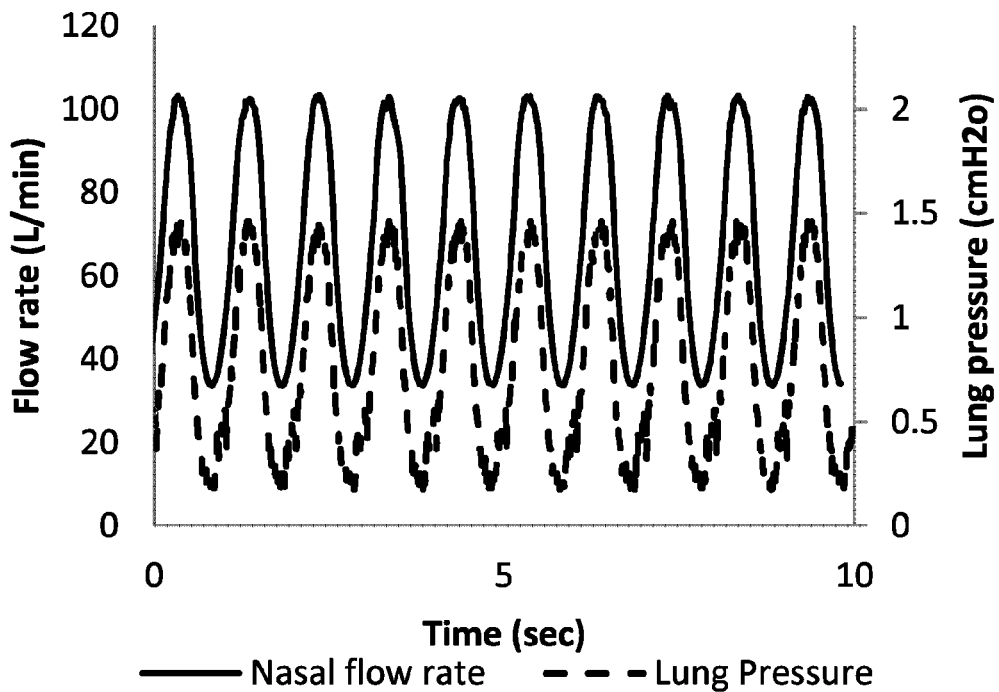

It has been previously suggested that one of the benefits of NHF, in addition to flushing parts of physiologic dead (nasal cavity down to larynx region), is the modest increase of static lung pressure. This pressure typically scales as the approximate square of flow rate, and is on the order of 1 cmH2O (compared with ~15 cmH2O during mechanical ventilation). Pressures generated with NHF are thought to be beneficial in preventing lung atelectasis in apnoea which, in turn, improves the ventilation/perfusion matching of the respiratory system and prevents desaturation. It was surprising to find that the pressure changes generated as a result of oscillating the flow in an open HNF system were sufficient enough to promote gas movement in the upper airways and into the lungs. Examples of lung pressures as a function of constant and varying NHF rates are shown in FIGS. 112 and 13A. The FIG. 12 highlights the square nature of the pressure-flow relation and suggest that oscillating high flow is more effective than oscillating low flows (for adults, those are typically at or below 15 L/min). The high flow rates used clinically on adults could reach up to 150 L/min, or more, for example. FIG. 13A demonstrates that sinusoidal flow oscillations between 35-105 L/min at a frequency of 1 Hz can effectively promote pressure changes (with phase lag dependent on airway resistance) which in turn can improve volumetric flow into/out of the lungs as consequence of lung compliance (the pressure/volume relation).

Figure 13B:
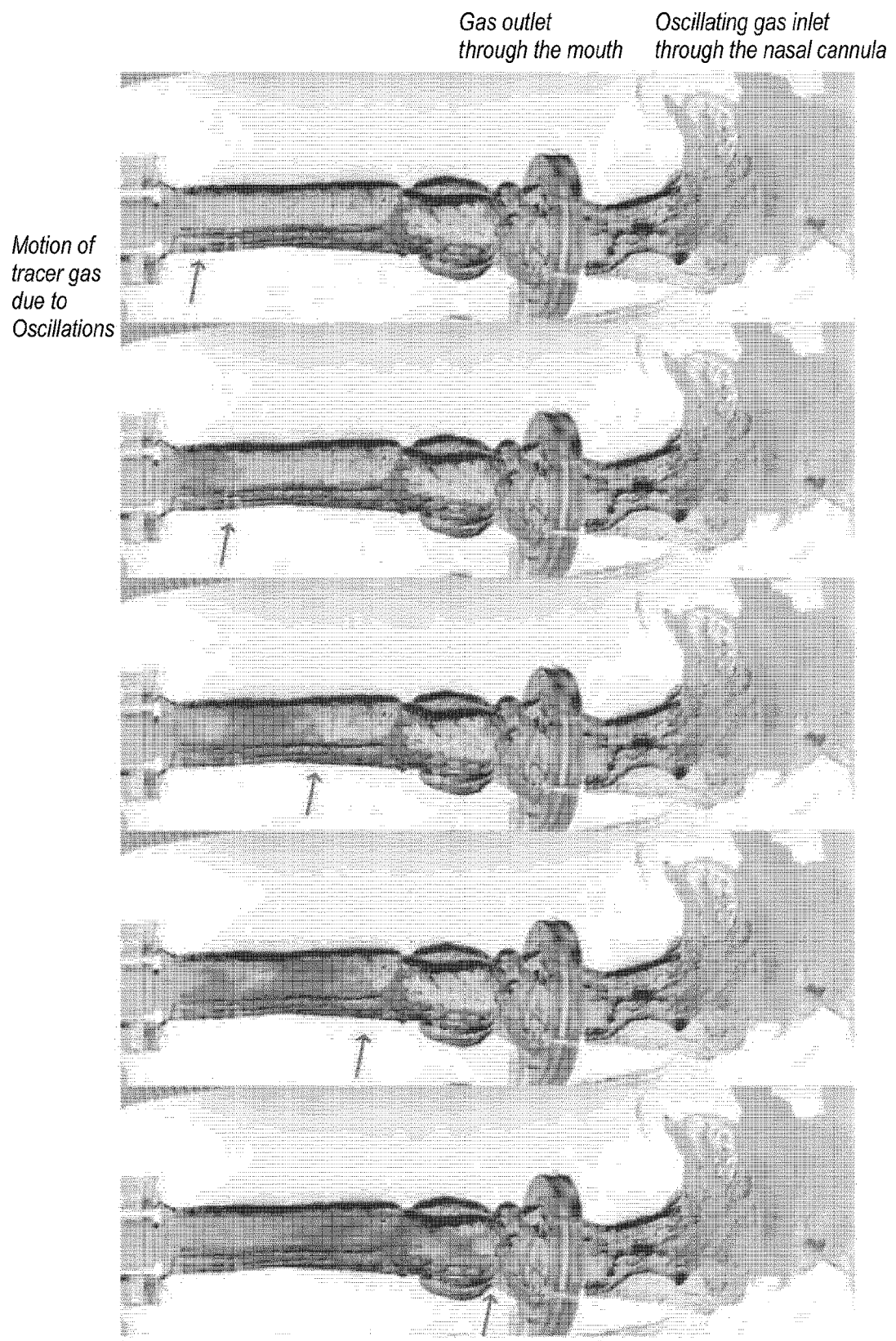
FIG. 13B shows gas flow in the airway during due to delivery of oscillating gas flow.

FIG. 13B shows a sequence of high speed images captures at about 6 ms intervals and demonstrate the motion of gas during the initial part of a sinusoidal flow oscillation between 30-100 L/min at 1 Hz. This bulk convection is fast (about 1 m/s) and is responsible for exchanging $CO_2$ from the lower airways of the lungs with the fresh incoming gas above the larynx during each oscillation. The distance a parcel of gas travels during a single flow oscillation is not only dependant on the flow rate but also on the frequency of oscillation and the shape of the waveform as those will dictate gas acceleration, time of flight and any intra- or inter-parcel mixing that may take place. The latter is thought to be beneficial in improving gas exchange as the concentration gradients along the lung airways are reduced.

2.5.3 Example #2

Nasal high flow was delivered with nasal cannula (large) and oscillated between 30 and 100 L/min at frequencies between 0-20 Hz using a sinusoidal waveform. Cardiogenic oscillations were applied at a frequency of 1 Hz at 270 degrees out of phase to the flow with a stroke volume 22.5 mL.

Furthermore, matching the phase (i.e. synchronising) of nasal high flow and cardiogenic oscillations can provide an additional improvement in $CO_2$ clearance by nearly a factor of 6. This suggests that it would be beneficial to have at least one waveform with a period matching that of the heart activity and with constant relative phase to that signal. Resting heart rates are typically between 40-100 bpm (0.67-1.67 Hz) but could be in the range of 30-180 bpm (0.5-3 Hz) under extreme physiology (e.g. under medical procedures or intense exercise).

It is worth noting that matching the NHF phase shift to that of cardiogenic oscillations is most meaningful when the two frequencies are identical, otherwise phase shift is inevitable.

2.5.4 Example #3

Figure 14:
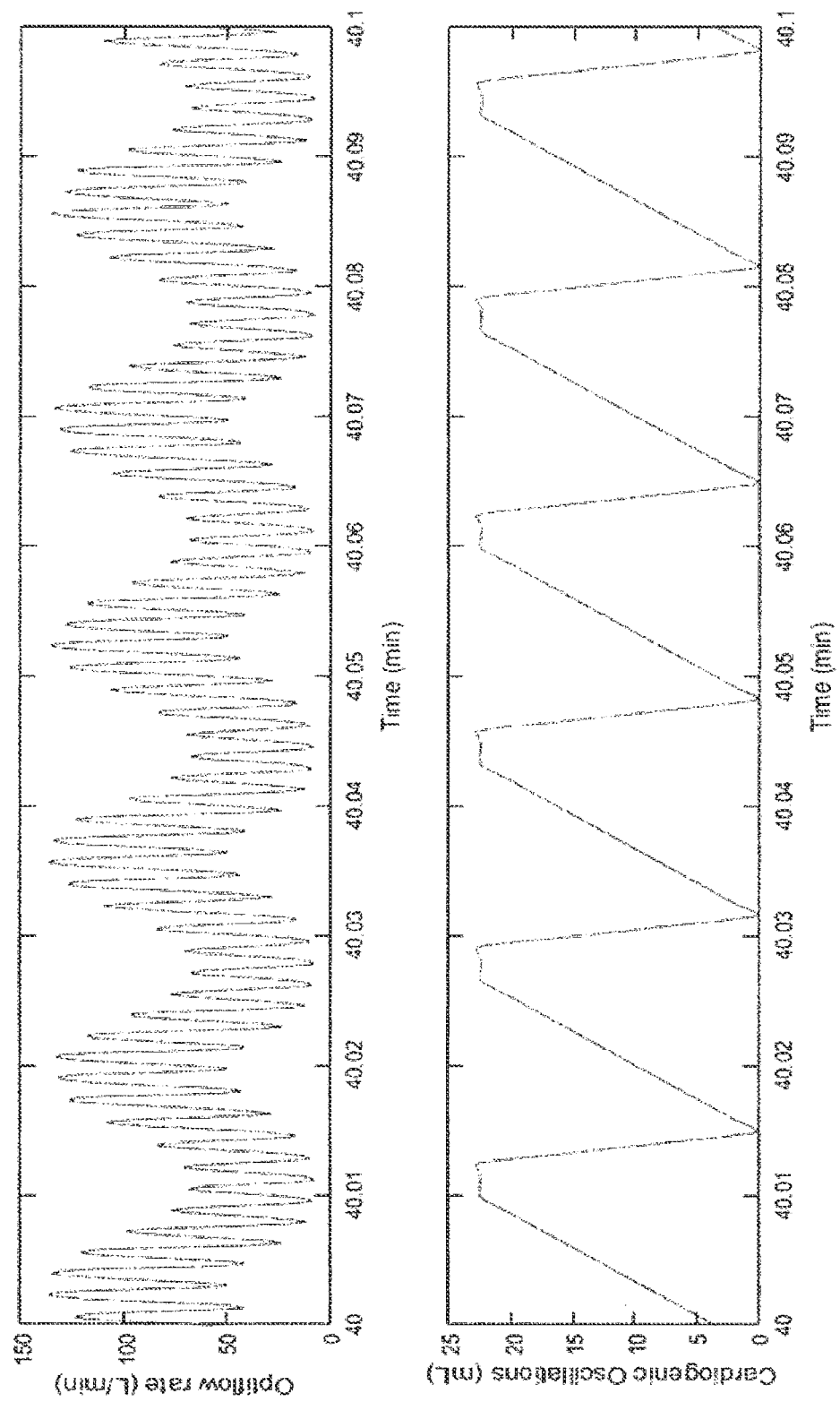
FIG. 14 shows the oscillating flow rate in relation to cardiogenic oscillations.

Nasal high flow was delivered with nasal cannula (large) and oscillated between 6 L/min (amplitude minimum) and 136 L/min (amplitude maximum) at 1 Hz and 10 Hz simultaneously (FIG. 7—top panel). The cardiogenic oscillations were applied at a frequency of 1 Hz and phase shifted between 0 and 270 degrees in 90 degree increments to the nasal high flow (see FIG. 14—bottom panel). The stroke volume was set to 22.5 mL with a frequency of 1 Hz.

Figure 15:
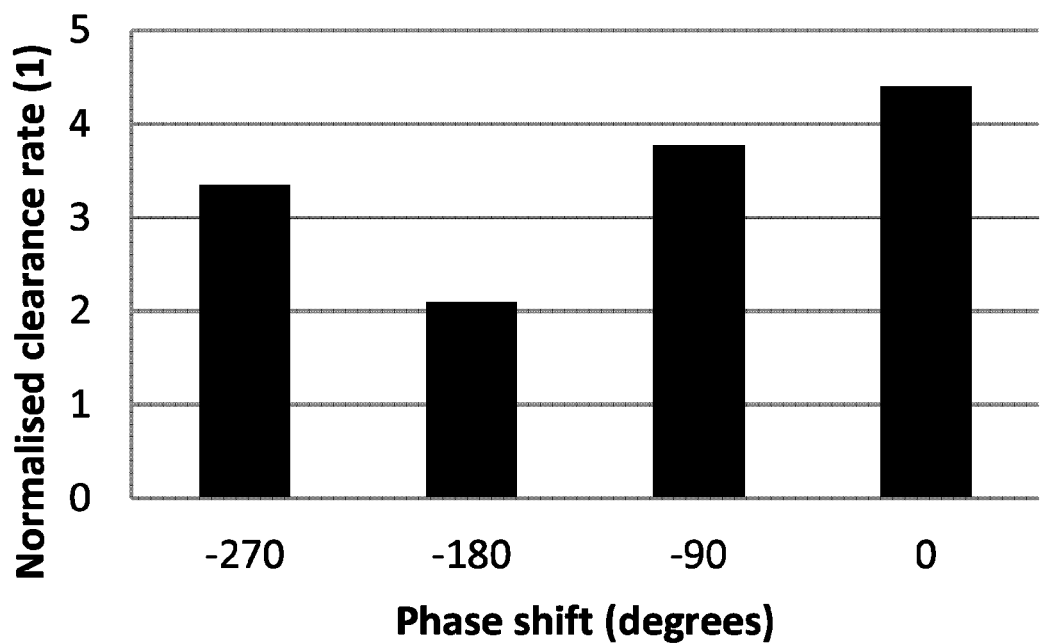
FIG. 15 shows CO2 clearance in relation to oscillatory component phase shifts.

The clearance rates indicate that syncing with the heart (a phase shift of 0) provides twice the enhancement to the contrary (a phase shift of 180 degrees) (see FIG. 15). This is because the combined effects of flow and cardiogenic volume changes in the trachea are physically added; thus, amplifying gas motion. That said, good clearance is still achieved at other phase shifts, such as or about 90 degrees, 180 degrees, 270 degrees or any other phase shift. The enhancement at any phase shift is still great than the base flow, which demonstrates that frequency matching is beneficial at any phase off-set. It is worth noting that the exact value of the phase shift is highly dependent on the shape and in some cases amplitude of the cardiogenic waveform as the addition of sinusoid and non-idealised trapezoid could be non-intuitive. In addition, the plug of gas displaced in the trachea with each cardiogenic oscillation may not take place instantaneously after every heart beat due to delays in the transmission of the pulsatile wave from the blood, through the airway tissues and into the gas where acceleration of the gas parcels would then take place. These delays in transmission would depend on the patient's physiology (e.g. heart rate, blood pressure, airway resistance etc.) and it is therefore more useful to sync with the cardiogenic pulse in the gas phase. This can be done by matching the frequency with the heart activity and either measuring, or inferring the phase shift (by calculation or $CO_2$ clearance measurements).

Note that in a clinical setting the patient's physiology may vary with time and therefore the phase shift should also be a variable. This means that syncing with the heart signal could be in-phase (or with constant relative phase), out of phase or anything in between. In the cases where the variability is too large it might be beneficial to use a measured or calculated mean phase shift value where the NHF and heart signals are matched in a time-averaged or population-averaged sense.

2.5.5 Example #4

FIG. 19 illustrates the use of multiple summed oscillating flow rate components with different frequencies. This example illustrates the benefit on gas exchange ($CO_2$ removal and/or oxygenation) by combining multiple nasal high flow flow rate frequencies to create a varying flow rate waveform with multiple summed frequencies, such as shown in that Figure.

Four NHF sinusoidal waveforms were tested and compared to a constant base flow of about 65 L/min with cardiogenic oscillations. The first NHF waveform oscillated at about 1 Hz from about 55 litres/min to about 100/min (FIG. 19—second panel), the second oscillated at about 0.1 Hz from about 50 litres/min to about 90 litres/min (FIG. 19—third panel), the third oscillated at about 20 Hz from about 60 litres/min to about 80 L/min (Figure—fourth panel), and the fourth superimposed all three waveforms (FIG. 19—fifth panel). A heart signal with arbitrary units is shown in FIG. 19—first panel).

Figure 20:
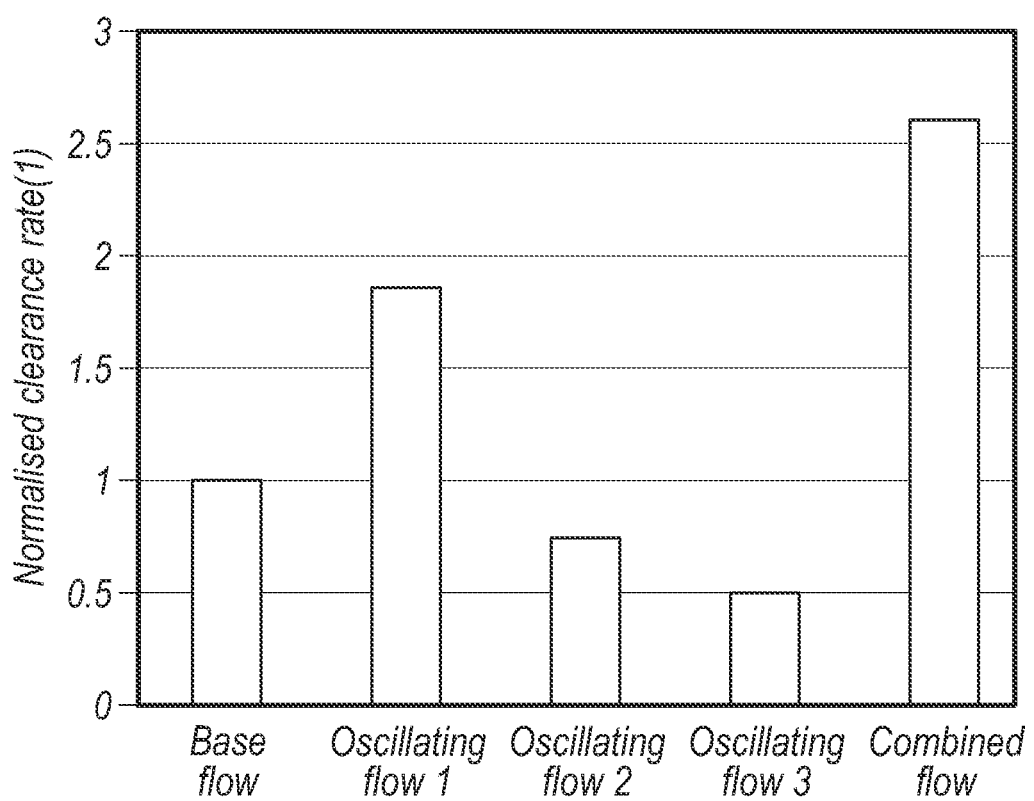
FIG. 20 shows a graph of clearance rate based on the various components.

FIG. 20 shows that the clearance rate for the combined waveform is larger than the base flow and any individual component (denoted as oscillating flows 1, 2, and 3). The results suggest that a synergistic effect exists in which gas exchange is favoured for waveforms with multiple periods. This is because the oscillation frequency influences both the bulk and local gas mixing and that reduces concentration gradients along the airway tree. High frequency components can also promote airway/tissue resonance which could amplify the clearance rates. Typical resonance frequencies of the lung-chest wall in infants and adults are around 18 and 6 Hz respectively.

The foregoing description of the invention includes preferred forms thereof. Modifications may be made thereto without departing from the scope of the invention.

The invention claimed is:

1. A method for oxygenation and/or CO2 clearance of a patient, the method comprising:
   delivering a varying gas flow with at least two oscillating components, wherein:
      a first oscillating component has a frequency based on heart activity of the patient, the frequency based on the heart activity is about 0.1 Hz to about 3 Hz, and
      a second oscillating component has a frequency to:
         promote bulk gas flow movement, or
         promote mixing.

2. The method according to claim 1, further comprising delivering the varying gas flow with a third oscillating component with a frequency to:
   promote bulk gas flow movement, or
   promote mixing.

3. The method according to claim 1, wherein the second oscillating component has the frequency to promote bulk gas movement, the frequency for the bulk gas flow movement is about 0.05 Hz to about 5 Hz.

4. The method according to claim 2, wherein the third oscillating component has the frequency to promote the mixing, the frequency to promote the mixing is about 3.5 Hz to about 150 Hz.

5. The method of claim 1, wherein the second oscillating component has the frequency to promote the bulk gas flow movement, the frequency to promote the bulk gas flow movement is lower than the frequency based on the heart activity of the patient.

6. The method of claim 1, wherein the second oscillating component has the frequency to promote the mixing, the frequency to promote the mixing is higher than the frequency based on the heart activity.

7. The method of claim 1, further comprising receiving an input from a heart activity sensor.

8. The method of claim 1, further comprising receiving an input from a flow sensor.

9. The method of claim 1, wherein the second oscillating component has the frequency to promote the bulk gas movement, the frequency to promote the bulk gas movement is based on a body cavity resonance.

10. The method of claim 9, further comprising receiving an input relating to the body cavity resonance from a body cavity sensor.

11. The method of claim 10, wherein the body cavity resonance is a resonance of a lung or a chest cavity.

12. The method of claim 1, wherein the varying gas flow has an overall waveform comprising a base component with a period of about 0.3 seconds to about 15 seconds.

13. The method of claim 1, wherein each of the at least two oscillating components is a flow rate component.

14. The method of claim 1, wherein the varying gas flow comprises a base flow rate of about 20 litres/min to about 90 litres/min.

15. The method of claim 1, further comprising controlling a valve that provides the varying gas flow.

16. The method of claim 15, wherein the valve is a gas flow modulator, wherein the gas flow modulator comprises:
   an underwater pressure release valve;
   oscillatable diaphragm;
   in-line linear actuator;
   flow chopper;
   aerodynamic or mechanical flutter valve; or
   proportional valve.

17. The method of claim 1, wherein the varying gas flow has a phase based on the heart activity.

18. The method of claim 1, further comprising delivering the varying gas flow to the patient by a patient interface.

19. The method of claim 1, further comprising delivering the varying gas flow to the patient by a non-sealing cannula.

20. The method of claim 1, wherein the frequency of the first oscillating component is based on a trachea flow and the heart activity of the patient.

* * * * *